United States Patent
Hakii et al.

(10) Patent No.: US 9,871,222 B2
(45) Date of Patent: *Jan. 16, 2018

(54) ORGANIC ELECTROLUMINESCENCE ELEMENT AND ILLUMINATION DEVICE

(71) Applicant: Konica Minolta, Inc., Tokyo (JP)

(72) Inventors: Takeshi Hakii, Sagamihara (JP); Hiroshi Ishidai, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/152,068

(22) Filed: May 11, 2016

(65) Prior Publication Data

US 2016/0254488 A1    Sep. 1, 2016

Related U.S. Application Data

(62) Division of application No. 13/984,713, filed as application No. PCT/JP2012/052584 on Feb. 6, 2012, now Pat. No. 9,368,735.

(30) Foreign Application Priority Data

Feb. 15, 2011 (JP) .................. 2011-029460

(51) Int. Cl.
    *H01L 51/00* (2006.01)
    *C07D 213/79* (2006.01)
    (Continued)

(52) U.S. Cl.
    CPC ........ *H01L 51/5253* (2013.01); *C07D 213/79* (2013.01); *C07D 221/10* (2013.01);
    (Continued)

(58) Field of Classification Search
    None
    See application file for complete search history.

(56) References Cited

U.S. PATENT DOCUMENTS 9,368,735 B2 *  6/2016  Hakii .................. C07D 213/79
2008/0315763 A1* 12/2008  Dobbertin ........... H01L 51/5088
                                                              313/512
2011/0114925 A1   5/2011  Hsu

FOREIGN PATENT DOCUMENTS

EP         2123733 A2   11/2009
JP       2000058265 A    2/2000
(Continued)

OTHER PUBLICATIONS

Extended European Search Report dated Jul. 14, 2016 from the corresponding European Application; Application No./Patent No. 12746825.4-1555 / 2677560 PCT/JP2012052584; Applicant: Konica Minolta, Inc.

*Primary Examiner* — Daniel Whalen
(74) *Attorney, Agent, or Firm* — Lucas & Mercanti, LLP

(57) ABSTRACT

An object is providing an organic electroluminescence element and an illumination device in which a driving voltage does not increase even when a high-productivity sputtering method is used to form a transparent conductive layer of the organic electroluminescence element of a top or top-and-bottom emission type, and hence which has an improved driving voltage. The organic electroluminescence element includes at least a light emitting layer and a transparent conductive layer. Between the light emitting layer and the transparent conductive layer, a transparent protective layer is disposed. The light emitting layer contains a phosphorescence emitting compound. The transparent protective layer contains a metal oxide. The metal oxide is a molybdenum (VI) oxide, a rhenium (VI) oxide or a nickel (II) oxide in an oxygen deficient state.

14 Claims, 3 Drawing Sheets

(51) Int. Cl.
| | |
|---|---|
| *H01L 51/52* | (2006.01) |
| *C07D 221/10* | (2006.01) |
| *C07D 233/58* | (2006.01) |
| *C07D 401/14* | (2006.01) |
| *C07D 405/14* | (2006.01) |
| *C07D 409/14* | (2006.01) |
| *C07D 417/14* | (2006.01) |
| *C07D 471/04* | (2006.01) |
| *C07D 519/00* | (2006.01) |
| *C09K 11/06* | (2006.01) |
| *H05B 33/10* | (2006.01) |
| *H01L 51/50* | (2006.01) |

(52) U.S. Cl.
CPC ......... *C07D 233/58* (2013.01); *C07D 401/14* (2013.01); *C07D 405/14* (2013.01); *C07D 409/14* (2013.01); *C07D 417/14* (2013.01); *C07D 471/04* (2013.01); *C07D 519/00* (2013.01); *C09K 11/06* (2013.01); *H01L 51/0072* (2013.01); *H01L 51/0073* (2013.01); *H01L 51/0085* (2013.01); *H01L 51/0087* (2013.01); *H01L 51/5012* (2013.01); *H01L 51/5072* (2013.01); *H01L 51/5092* (2013.01); *H01L 51/5228* (2013.01); *H01L 51/5234* (2013.01); *H05B 33/10* (2013.01); *C09K 2211/1007* (2013.01); *C09K 2211/1011* (2013.01); *C09K 2211/1014* (2013.01); *C09K 2211/1029* (2013.01); *C09K 2211/1033* (2013.01); *C09K 2211/1044* (2013.01); *C09K 2211/1048* (2013.01); *C09K 2211/1059* (2013.01); *C09K 2211/1088* (2013.01); *C09K 2211/1092* (2013.01); *C09K 2211/1096* (2013.01); *H01L 51/006* (2013.01); *H01L 51/0052* (2013.01); *H01L 51/0058* (2013.01); *H01L 51/0081* (2013.01); *H01L 51/5016* (2013.01); *H01L 2251/5361* (2013.01)

(56) References Cited

FOREIGN PATENT DOCUMENTS

| | | |
|---|---|---|
| JP | 2000068063 A | 3/2000 |
| JP | 2005135706 A | 5/2005 |
| JP | 2005158583 A | 6/2005 |
| JP | 2005158693 A | 6/2005 |
| JP | 2008041692 A | 2/2008 |
| JP | 4366686 B2 | 4/2009 |
| JP | 2009212222 A | 9/2009 |
| JP | 2010251675 A | 11/2010 |
| JP | 2011009517 A * | 1/2011 |
| WO | 2011013759 A1 | 2/2011 |
| WO | 2011040193 A1 | 4/2011 |

* cited by examiner

ORGANIC ELECTROLUMINESCENCE ELEMENT AND ILLUMINATION DEVICE

CROSS-REFERENCE TO RELATED APPLICATION

This application is a divisional application of U.S. application Ser. No. 13/984,713, filed Aug. 9, 2013, which in turn was a 371 of PCT/JP2012/052584, filed Feb. 6, 2012, which claims the benefit of JP Patent Application No. 2011-029460, filed Feb. 15, 2011, the contents of each application are incorporated herein by reference.

TECHNICAL FIELD

The present invention relates to an organic electroluminescence element and an illumination device applied to a display device, a lighting fixture and the like.

BACKGROUND ART

Recently, surface emitting bodies have attracted attention, the surface emitting bodies being used as backlights for various kinds of displays, display boards such as signboards and emergency lights, light sources for lighting fixtures and the like, because the surface emitting bodies have many advantages such as having high brightness, high light emission efficiency, small thickness and light weight. Among the surface emitting bodies, an organic electroluminescence element (hereinafter also called an organic EL element), which employs an organic material and emits light by electric energy from an anode and a cathode, has particularly attracted attention because the organic EL element can emit light at a low voltage of several volts to several ten volts, is of a thin-film type completely-solid state element and can save space, for example.

In order to increase the efficiency of the organic EL element, it is necessary to increase light extraction efficiency. However, the organic EL element has a short distance of several ten nm between a light emitting layer and a metal electrode. Hence, waveguide loss of surface plasmon mode light is large, and accordingly the light extraction efficiency does not increase. The element taking a top emission type structure is considered as a method for reducing the waveguide loss of the surface plasmon mode light.

One of the problems of the top emission type organic EL element is damaging the organic layers in a process of forming a transparent conductive layer, which lowers the light emission efficiency, increases a voltage and shortens life of the element, for example. In particular, the above problem is conspicuous when a sputtering method having high productivity is used as the process of forming the transparent conductive layer. Thus, it is a great challenge to balance productivity with element characteristics of the top emission type organic EL element. As a technology for balancing the productivity with the element characteristics, there has been a technology for preventing damage to the organic layers in the process of forming the transparent conductive layer by providing a layer (hereinafter called a transparent protective layer) made of a metallophthalocyanine material such as copper phthalocyanine between the transparent conductive layer and the light emitting layer (see Patent Documents 1 and 2). However, because copper phthalocyanine, which has low transmittance, is used as the material of the transparent protective layer, the light emission efficiency decreases, which is a weakness of the technology.

As another technology, it has been examined to use a layer made of a titanium oxide, a vanadium oxide, a zirconium oxide or a lanthanum oxide deposited in an oxygen deficient state (see Patent Document 3). This is a technology for preventing oxidation damage to the organic layers by trapping oxygen radical, which is generated in the sputtering process of forming the transparent conductive layer, with the transparent protective layer by utilizing the fact that the above-mentioned metal oxides in the oxygen deficient state are unstable. Hence, it is effective in preventing oxidation damage to the organic layers in the sputtering process, but has the problem that the voltage increases by oxidation of the transparent protective layer. In particular, if, in view of productivity, discharge power for sputtering is increased so that a deposition rate for the transparent protective layer becomes higher, it is necessary to make the transparent protective layer thick enough to prevent damage to the organic layers. When the transparent protective layer is thick, the problem that the voltage increases by oxidation of the transparent protective layer in the sputtering process becomes bigger.

RELATED ART DOCUMENT

Patent Document

Patent Document 1: Japanese Patent Application Laid-Open Publication No. 2000-58265
Patent Document 2: Japanese Patent Application Laid-Open Publication No. 2000-68063
Patent Document 3: Japanese Patent No. 4366686

SUMMARY OF THE INVENTION

Problems to be Solved by the Invention

The present invention is made in view of the above-described problem, and an object of the present invention is to provide an organic electroluminescence element and an illumination device in each of which a driving voltage does not increase even when a high-productivity sputtering method is used to form a transparent conductive layer of the organic electroluminescence element, namely, each of which has an improved driving voltage, the organic electroluminescence element being of a top emission type or a top-and-bottom emission type.

Means for Solving the Problems

The object can be achieved by the following configurations.

1. One of the configurations is an organic electroluminescence element including at least a light emitting layer and a transparent conductive layer, and further including a transparent protective layer disposed between the light emitting layer and the transparent conductive layer, wherein the light emitting layer contains a phosphorescence emitting compound, the transparent protective layer contains a metal oxide, the metal oxide is a molybdenum (VI) oxide, a rhenium (VI) oxide or a nickel (II) oxide, and the molybdenum (VI) oxide, the rhenium (VI) oxide and the nickel (II) oxide are in an oxygen deficient state.

2. One of the configurations is the organic electroluminescence element according to the above 1, wherein the transparent protective layer has a thickness of 60 nm to 150 nm.

3. One of the configurations is the organic electroluminescence element according to the above 1 or 2 further including an electron transport layer between the light emitting layer and the transparent protective layer.

4. One of the configurations is the organic electroluminescence element according to the above 1 or 2 further including a positive hole transport layer between the light emitting layer and the transparent protective layer.

5. One of the configurations is the organic electroluminescence element according to the above 3, wherein the electron transport layer contains a compound represented by the following general formula (1):

(Ar1)$_{n1}$-Y1    General Formula (1)

wherein, provided that the compound represented by the general formula (1) has in a molecule at least two condensed aromatic heterocycles each formed in such a manner that three or more rings are condensed, n1 represents an integer of one or more; Y1 represents a substituent when n1 is one and represents a bond or an n1-valent linking group when n1 is two or more; and Ar1 represents a group represented by the following general formula (A), and a plurality of Ar1 are identical or different when n1 is two or more:

[Chem. 1]

General Formula (A)

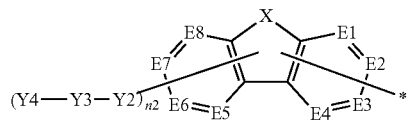

wherein X represents N(R), O, S or Si(R)(R'), E1 to E8 each represent C(R1) or N, and R, R' and R1 each represent a hydrogen atom, a substituent or a linking site with Y1; * represents a linking site with Y1; Y2 represents a bond or a divalent linking group; Y3 and Y4 each represent a group derived from a five-membered or six-membered aromatic ring, and at least one of Y3 and Y4 represents a group derived from an aromatic heterocycle containing a nitrogen atom as a ring constituent atom; and n2 represents an integer of one to four.

6. One of the configurations is the organic electroluminescence element according to the above 5, wherein the compound represented by the general formula (1) is a compound represented by the following general formula (2):

[Chem. 2]

General Formula (2)

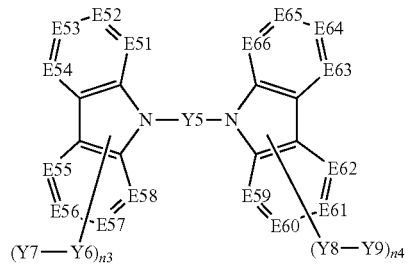

wherein Y5 represents a divalent linking group which is an arylene group, a heteroarylene group or a combination of the arylene group and the heteroarylene group; E51 to E66 each represent C(R3) or N, and R3 represents a hydrogen atom or a substituent; Y6 to Y9 each represent a group derived from an aromatic hydrocarbon ring or a group derived from an aromatic heterocycle, and at least one of Y6 and Y7 and at least one of Y8 and Y9 each represent a group derived from an aromatic heterocycle containing an N atom; and n3 and n4 each represent an integer of zero to four, provided that the sum of n3 and n4 is two or more.

7. One of the configurations is the organic electroluminescence element according to the above 6, wherein the compound represented by the general formula (2) is a compound represented by the following general formula (3):

[Chem. 3]

General Formula (3)

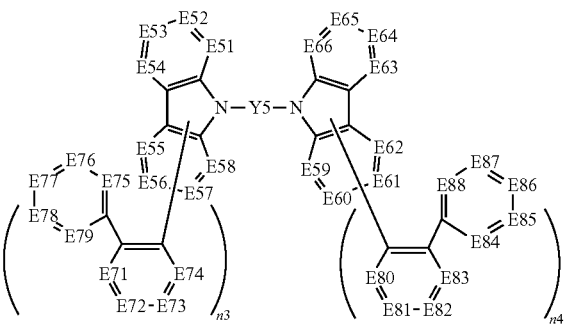

wherein Y5 represents a divalent linking group which is an arylene group, a heteroarylene group or a combination of the arylene group and the heteroarylene group; E51 to E66 and E71 to E88 each represent C(R3) or N, and R3 represents a hydrogen atom or a substituent, provided that at least one of E71 to E79 and at least one of E80 to E88 each represent N; and n3 and n4 each represent an integer of zero to four, provided that the sum of n3 and n4 is two or more.

8. One of the configurations is the organic electroluminescence element according to any one of the above 1 to 7, wherein the phosphorescence emitting compound is represented by the following general formula (4):

[Chem. 4]

General Formula (4)

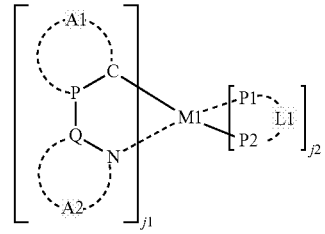

wherein P and Q each represent a carbon atom or a nitrogen atom; A1 represents an atom group which forms an aromatic hydrocarbon ring or an aromatic heterocycle with P—C; A2 represents an atom group which forms an aromatic heterocycle with Q-N; P1-L1-P2 represents a bidentate ligand, P1 and P2 each independently represent a carbon atom, a nitrogen atom or an oxygen atom, and L1 represents an atom group which forms the bidentate ligand with P1 and P2; j1 represents an integer of one to three, and j2 represents an integer of zero to two, provided that the sum of j1 and j2 is two or three; and M1 represents a transition metal element of groups 8 to 10 in the element periodic table.

9. One of the configurations is the organic electroluminescence element according to the above 8, wherein the compound represented by the general formula (4) is a compound represented by the following general formula (5):

[Chem. 5]

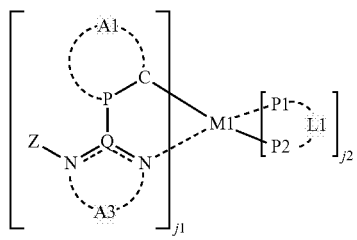

General Formula (5)

wherein Z represents a hydrocarbon ring group or a heterocyclic group; P and Q each represent a carbon atom or a nitrogen atom; A1 represents an atom group which forms an aromatic hydrocarbon ring or an aromatic heterocycle with P—C; A3 represents C(R01)=C(R02), N=C(R02), C(R01)=N or N=N, and R01 and R02 each represent a hydrogen atom or a substituent; P1-L1-P2 represents a bidentate ligand, P1 and P2 each independently represent a carbon atom, a nitrogen atom or an oxygen atom, and L1 represents an atom group which forms the bidentate ligand with P1 and P2; j1 represents an integer of one to three, and j2 represents an integer of zero to two, provided that the sum of j1 and j2 is two or three; M1 represents a transition metal element of groups 8 to 10 in the element periodic table; and a broken line represents a single bond or a double bond.

10. One of the configurations is the organic electroluminescence element according to the above 8 or 9, wherein the M1 represents iridium.

11. One of the configurations is the organic electroluminescence element according to any one of the above 1 to 10 further including an auxiliary electrode on the transparent conductive layer.

12. One of the configurations is the organic electroluminescence element according to the above 11, wherein the transparent protective layer is subjected to patterning, and the auxiliary electrode is formed above a non-patterned region of the transparent protective layer.

13. One of the configurations is the organic electroluminescence element according to any one of the above 1 to 12, wherein the organic electroluminescence element is of a top-and-bottom emission type.

14. One of the configurations is an illumination device including the organic electroluminescence element according to any one of the above 1 to 13.

Advantageous Effects of the Invention

According to the present invention, an organic electroluminescence element and an illumination device each having high productivity and an improved driving voltage can be provided.

EMBODIMENTS FOR CARRYING OUT THE INVENTION

Figure 1A:
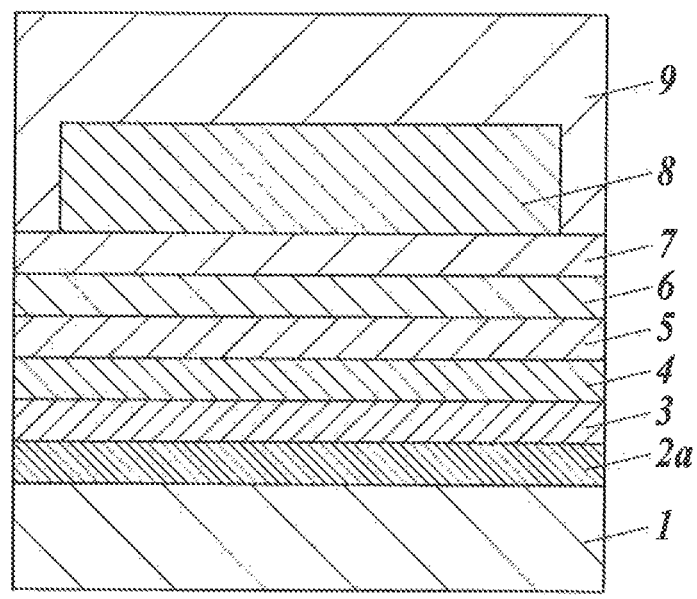
FIG. 1A shows a specific example of the layer structure of a top-and-bottom emission type organic EL element having a transparent conductive layer as a cathode of the present invention.

In the following, a preferred embodiment for carrying out the present invention is detailed. However, the present invention is not limited thereto.

In the following, an embodiment for carrying out the present invention is detailed.

An organic electroluminescence element of the present invention has a transparent protective layer made of a metal oxide as a main component between a transparent conductive layer and a light emitting layer, and the light emitting layer contains a phosphorescence emitting compound. The transparent protective layer is a layer to prevent damage to the light emitting layer in a process of forming the transparent protective layer and the following processes. Using a layer containing a phosphorescence emitting compound as the light emitting layer prevents voltage increase caused by a sputtering process of forming the transparent conductive layer, with no increase of the thickness of the transparent protective layer. Further, using a transparent protective layer containing a molybdenum (VI) oxide, a rhenium (VI) oxide or a nickel (II) oxide in the oxygen deficient state as the metal oxide further increases the effect of the present invention. This is because a molybdenum (VI) oxide, a rhenium (VI) oxide and a nickel (II) oxide each have relatively high stability in the oxygen deficient state and accordingly the transparent protective layer does not easily oxidize in the sputtering process, or because the transparent protective layer containing a molybdenum (VI) oxide, a rhenium (VI) oxide or a nickel (II) oxide can be made thicker than a transparent protective layer containing another metal oxide and accordingly damage to the light emitting layer can be further reduced.

In the following, an organic electroluminescence element including an electron injection layer of the present invention is described.

<<Organic EL Element>>

First, an embodiment of an organic EL element of the present invention, which is an example of a surface emitting body, is detailed. The contents described below are regarding a representative embodiment of the present invention, and hence the present invention is not limited to these contents unless departing from the spirit of the present invention.

First, preferred specific examples of the layer structure of the organic EL element are shown below.

(i) anode/light emitting layer/electron transport layer/electron injection layer/transparent protective layer/cathode (ii) anode/positive hole injection layer/positive hole transport layer/light emitting layer/electron transport layer/electron injection layer/transparent protective layer /cathode (iii) anode/positive hole transport layer/light emitting layer/positive hole block layer/electron transport layer/electron injection layer/transparent protective layer /cathode (iv) anode/transparent protective layer/positive hole injection layer/positive hole transport layer/light emitting layer/ electron transport layer/electron injection layer/ cathode (v) anode/transparent protective layer/positive hole transport layer/light emitting layer/positive hole block layer/ electron transport layer/electron injection layer/ cathode With respect to the organic EL element of the present invention, an electrode formed after a transparent protective layer is formed is a transparent conductive layer, and a counter electrode can be transparent or nontransparent depending on application. The organic EL element of the present invention preferably has a top emission type structure or a top-and-bottom emission type structure.

FIG. 1A shows an example of the top-and-bottom emission structure in which a transparent conductive layer 9 is a cathode, the structure corresponding to the structure of the above (ii), wherein an anode 2a is on a substrate 1 side.

Figure 1B:
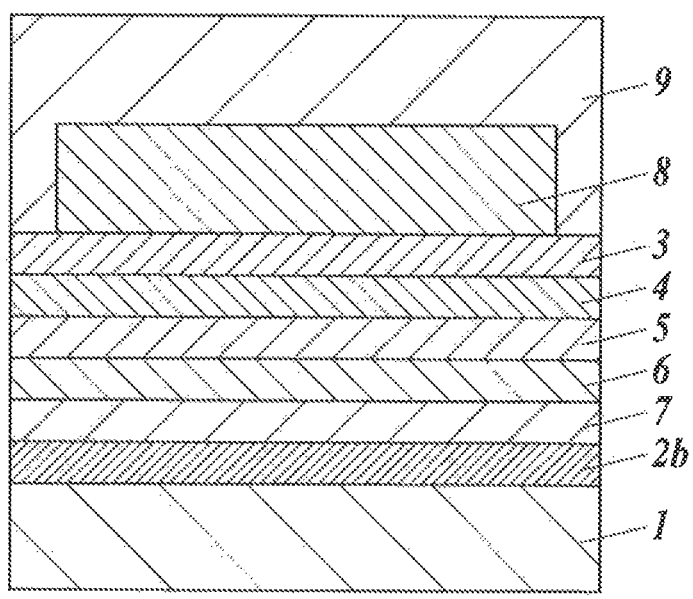
FIG. 1B shows a specific example of the layer structure of a top emission type organic EL element having a transparent conductive layer as an anode of the present invention.

FIG. 1B shows an example of the top emission type structure in which the transparent conductive layer 9 is an anode, the structure corresponding to the structure of the above (iv), wherein a cathode 2b is on the substrate 1 side.

The transparent protective layer of the present invention is formed between the transparent conductive layer, which is formed by sputtering or the like, and organic layers including the light emitting layer.

The light emitting layer preferably contains at least two types of light emitting materials the luminescent colors of which are different from each other. The light emitting layer may be a single light emitting layer or a light emitting layer unit composed of a plurality of light emitting layers. A positive hole injection layer and an electron block layer are of the positive hole transport layer.

<<Transparent Protective Layer>>

The transparent protective layer of the present invention is a substantially transparent layer which prevents process damage to the light emitting layer in processes following a process for the transparent protective layer. The "substantially transparent" in the present invention means that visible light transmittance is 50% or more.

An organic EL element of the present invention has a transparent protective layer between a transparent conductive layer and a light emitting layer. Having a transparent protective layer between a transparent conductive layer and a light emitting layer prevents deterioration of the light emitting layer in a process for the transparent protective layer and the following processes.

The transparent protective layer of the present invention has a metal oxide as a main component, and the metal oxide of the present invention is a molybdenum (VI) oxide, a rhenium (VI) oxide or a nickel (II) oxide.

The metal oxide of the present invention is in the oxygen deficient state. The oxygen deficient state is a state of being a non-stoichiometric composition of an oxygen deficient type. For example, a molybdenum (VI) oxide in the oxygen deficient state means that a molybdenum oxide has a molybdenum oxide having a valence of less than six.

As a method for forming the transparent protective layer of the present invention, an evaporation method is preferable.

The thickness of the transparent protective layer of the present invention is preferably 60 nm or more and 150 nm or less in order to sufficiently prevent oxidation damage to the organic layers. If the thickness thereof is too small, the light emitting layer deteriorates in the process for forming the transparent conductive layer. On the other hand, if the thickness is too large, the light extraction efficiency decreases.

The transparent protective layer of the present invention prevents oxidation damage, which is caused when the electrode is formed, to the organic layers. The molybdenum (VI) oxide, the rhenium (VI) oxide or the nickel (II) oxide contained in the transparent protective layer is in the oxygen deficient state, and even when the thickness of the transparent protective layer is more than 60 nm, the driving voltage does not increase much. The molybdenum (VI) oxide, the rhenium (VI) oxide and the nickel (II) oxide are commercially available from regent manufacturers or the like and hence can be easily obtained.

As a method for forming the transparent protective layer of the present invention, the evaporation method is preferable. For example, by using a material used as an evaporation material such as a molybdenum (VI) oxide, the transparent protective layer is formed without introduction of oxygen into a system (into an evaporation device). The evaporation without introduction of oxygen does not form a stoichiometrically sufficient composition and accordingly can produce the transparent protective layer made of a metal oxide in the oxygen deficient state.

Except for no introduction of oxygen into the system, the film forming condition such as a heating temperature or a deposition rate can be appropriately changed depending on the evaporation material. The composition of the formed metal oxide film can be confirmed by ESCA (Electron Spectroscopy for Chemical Analysis)

The transparent protective layer of the present invention can be subjected to patterning as needed. Patterning the transparent protective layer makes the transparent conductive layer electrically contact an electron injection layer or a positive hole transport layer. Consequently, electrons or positive holes transported from the transparent conductive layer are transported to the electron injection layer or the positive hole transport layer not via the transparent protective layer, so that light emission can be carried out at a lower voltage. When the transparent protective layer of the present invention is subjected to patterning, it is preferable that patterning be carried out with respect to each space of 500 μm to 5,000 μm. The shape of its pattern is not particularly limited, but, for example, may be line-shaped or lattice-shaped. Examples of a method for patterning the transparent protective layer of the present invention include a shadow mask method, a laser thermal transfer method, a laser evaporation method, a laser ablation method, an ink-jet method and a printing method. As a method for patterning the transparent protective layer of the present invention, the shadow mask method with evaporation is preferable.

<<Auxiliary Electrode>>

The organic EL element of the present invention can be provided with an auxiliary electrode on the transparent conductive layer to lower resistance. As a material to form the auxiliary electrode, metal having low resistance such as aurum, platinum, argent, copper or aluminum is preferable. Examples of a method for forming the auxiliary electrode include the evaporation method, the sputtering method, the printing method, the ink-jet method and an aerosol jet method. It is preferable that the line width of the auxiliary electrode of the present invention be 50 μm or less in view of an aperture ratio of the transparent conductive layer, and the thickness of the auxiliary electrode is 1 μm or more in view of conductivity. In the case where the transparent protective layer is subjected to patterning, it is preferable that the auxiliary electrode of the present invention be formed above a non-patterned region of the transparent protective layer. The non-patterned region of the transparent protective layer in the present invention is a region where the transparent protective layer is not present.

<<Transparent Conductive Layer: Electrode>>

For the transparent conductive layer of the present invention, an optically-transparent conductive material such as indium tin oxide (ITO), $SnO_2$ or ZnO is used by preference. Alternatively, a material which can produce an amorphous optically-transparent conductive film such as IDIXO ($In_2O_3$—ZnO) may be used. As a method for forming the transparent conductive layer of the present invention, the sputtering method is preferable in view of productivity. The transparent conductive layer of the present invention may have a pattern formed in a desired shape by a photolithography method as needed. If not so high pattern accuracy is needed (about 100 μm or more), the pattern may be formed via a mask in a desired shape at the time of evaporation or sputtering of the above-mentioned electrode substance. It is preferable that sheet resistance of the transparent conductive layer of the present invention be several hundred Ω/□ or less. Further, although it depends on the material, the thickness thereof is selected usually from a range from 10 to 1000 nm, preferably from a range from 50 to 200 nm.

[Light Emitting Layer]

The light emitting layer of the present invention contains a phosphorescence emitting compound as a light emitting material.

The light emitting layer of the present invention is a layer which emits light through recombination of electrons and positive holes injected from an electrode, an electron transport layer and a positive hole transport layer. A portion to emit light may be either the inside of the light emitting layer or an interface between the light emitting layer and its adjacent layer.

The structure of the light emitting layer is not particularly limited as long as the light emitting material contained therein satisfies a light emission requirement. Further, the light emitting layer may be a plurality of light emitting layers having the same emission spectrum and/or emission maximum wavelength. In this case, it is preferable that non-luminescent intermediate layers are present in respective spaces between the light emitting layers.

The total thickness of the light emitting layers is preferably within a range from 1 to 100 nm and, in view of obtaining a lower driving voltage, far preferably within a range from 1 to 30 nm. The total thickness of the light emitting layers is, if the non-luminescent intermediate layers be present between the light emitting layers, the thickness including the thickness of the intermediate layers.

It is preferable to adjust the thickness of each light emitting layer to be within a range from 1 to 50 nm and far preferable to adjust the thickness thereof to be within a range from 1 to 20 nm. A relationship between the thickness of a blue light emitting layer, the thickness of a green light emitting layer and the thickness of a red light emitting layer is not particularly limited.

The light emitting layers can be formed through deposition of a light emitting material and a host compound, which are described below, by a well-known thin film forming method such as a vacuum evaporation method, a spin coating method, a casting method, an LB method or the ink-jet method.

In each light emitting layer, multiple light emitting materials may be combined. Alternatively, a phosphorescence emitting material and a fluorescence emitting material may be combined in a single light emitting layer.

It is preferable that the light emitting layer contain a host compound and a light emitting material (also called a light emitting dopant compound) and emit light through the light emitting material.

<Host Compound>

The host compound contained in the light emitting layer of the organic EL element is a compound having, in phosphorescence emission at room temperature (25° C.), a phosphorescence quantum yield, preferably of less than 0.1 and far preferably of less than 0.01. Further, of the compounds contained in the light emitting layer, a volume ratio of the host compound in the layer being 50% or more is preferable.

As the host compound, one type of well-known host compounds may be used, or multiple types thereof may be used together. Using multiple types of host compounds can adjust transfer of charges and hence can increase the efficiency of the organic EL element. Using multiple types of light emitting materials described below can mix different colors of light to be emitted and hence can produce any luminous color.

As the host compound, a well-known low molecular weight compound, a high molecular compound having a repeating unit or a low molecular weight compound provided with a polymerizable group such as a vinyl group or an epoxy group (an evaporation polymerizable emission host) may be used.

As the well-known host compound, a compound which has a positive hole transport capability and an electron transport capability, prevents red shift and has a high Tg (glass transition temperature) is preferable. The glass transition temperature Tg here is a value found by using DSC (Differential Scanning Colorimetry) according to JIS-K-7121.

Specific examples of the well-known host compound are described in the following documents; for example, Japanese Patent Application Laid-Open Publication Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084 and 2002-308837.

<Light Emitting Material>

Next, the light emitting material is described.

As the light emitting material, a phosphorescence emitting material (also called a phosphorescent compound, a phosphorescence emitting compound or the like) can be used.

The phosphorescence emitting material is a compound in which light emission from an excited triplet state is observed, and, to be more specific, a compound which emits phosphorescence at room temperature (25° C.) and exhibits at 25° C. a phosphorescence quantum yield of 0.01 or more, preferably of 0.1 or more.

The phosphorescence quantum yield can be measured by a method described on page 398 of Bunko II of Dai 4 Han Jikken Kagaku Koza 7 (Spectroscopy II of Lecture of Experimental Chemistry vol. 7, 4th edition) (1992, published by Maruzen Co., Ltd.). The phosphorescence quantum yield in a solution can be measured by using various solvents. With respect to the phosphorescence emitting material used in the present invention, it is only necessary to achieve the above-mentioned phosphorescence quantum yield (0.01 or more) with one of appropriate solvents.

Two kinds of principles regarding light emission of the phosphorescence emitting material are cited. One is an energy transfer type, wherein carriers recombine on a host compound which transfers the carriers so as to produce an excited state of the host compound, this energy is transferred to a phosphorescence emitting material, and hence light emission from the phosphorescence emitting material is carried out. The other is a carrier trap type, wherein a phosphorescence emitting material serves as a carrier trap, carriers recombine on the phosphorescence emitting material, and hence light emission from the phosphorescence emitting material is carried out. In either case, the excited state energy of the phosphorescence emitting material is required to be lower than that of the host compound.

The phosphorescence emitting material can be suitably selected from the well-known phosphorescence emitting compounds used for light emitting layers of organic EL elements, preferably a complex compound containing metal of Groups 8 to 10 in the element periodic table; far preferably an iridium compound, an osmium compound, a platinum compound (a platinum complex compound) or a rare-earth complex; and most preferably an iridium compound.

In the present invention, at least one light emitting layer may contain two or more types of light emitting materials, and a rate of concentration of the light emitting materials may vary in a direction of the thickness of the light emitting layer.

The phosphorescence emitting compound of the present invention is preferably a compound represented by General Formula (4).

<<Compound Represented by General Formula (4)>>

The phosphorescence emitting compound of the organic EL element of the present invention is preferably a compound represented by General Formula (4).

The compound represented by General Formula (4) is described below. It is preferable that the phosphorescence emitting compound (also called a phosphorescence emitting metal complex) represented by General Formula (4) be contained in the light emitting layer of the organic EL element of the present invention as a light emitting dopant, but may be contained in a constituent layer (constituent layers of the organic EL element of the present invention are detailed later) other than the light emitting layer.

Examples of an aromatic hydrocarbon ring which is formed by A1 with P—C in General Formula (4) include a benzene ring, a biphenyl ring, a naphthalene ring, an azulene ring, an anthracene ring, a phenanthrene ring, a pyrene ring, a chrysene ring, a naphthacene ring, a triphenylene ring, an o-terphenyl ring, an m-terphenyl ring, a p-terphenyl ring, an acenaphthene ring, a coronene ring, a fluorene ring, a fluoranthrene ring, a naphthacene ring, a pentacene ring, a perylene ring, a pentaphene ring, a picene ring, a pyrene ring, a pyranthrene ring and an anthranthrene ring.

These rings may each have a substituent represented by Y1 in General Formula (1) too.

Examples of an aromatic heterocycle which is formed by A1 with P—C in General Formula (4) include a furan ring, a thiophene ring, an oxazole ring, a pyrrole ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, a thiazole ring, an indole ring, a benzimidazole ring, a benzothiazole ring, a benzoxazole ring, a quinoxaline ring, a quinazoline ring, a phthalazine ring, a carbazole ring and an azacarbazole ring.

The azacarbazole ring indicates a ring formed in such a manner that at least one of carbon atoms of a benzene ring constituting a carbazole ring is substituted by a nitrogen atom.

These rings may each have a substituent represented by Y1 in General Formula (1) too.

Examples of an aromatic heterocycle which is formed by A2 with Q-N in General Formula (4) include an oxazole ring, an oxadiazole ring, an oxatriazole ring, an isoxazole ring, a tetrazole ring, a thiadiazole ring, a thiatriazole ring, an isothiazole ring, a pyrrole ring, a pyridine ring, a pyridazine ring, a pyrimidine ring, a pyrazine ring, a triazine ring, an imidazole ring, a pyrazole ring and a triazole ring.

These rings may each have a substituent represented by Y1 in General Formula (1) too.

Examples of a bidentate ligand represented by P1-L1-P2 in General Formula (4) include phenylpyridine, phenylpyrazole, phenylimidazole, phenyltriazole, phenyltetrazole, pyrazabole, acetylacetone and picolinic acid.

In General Formula (4), j1 represents an integer of one to three, and j2 represents an integer of zero to two, provided that the sum of j1 and j2 is two or three. In particular, j2 being zero is preferable.

In General Formula (4), M1 represents a transition metal element (simply called a transition metal) of Groups 8 to 10 in the element periodic table. In particular, M1 being iridium is preferable.

It is far preferable that the phosphorescence emitting compound of the present invention be a compound represented by General Formula (5).

<<Compound Represented by General Formula (5)>>

Of the compounds represented by General Formula (4) of the present invention, a compound represented by General Formula (5) is far preferable.

Examples of a hydrocarbon ring group represented by Z in General Formula (5) include a non-aromatic hydrocarbon ring group and an aromatic hydrocarbon ring group. Examples of the non-aromatic hydrocarbon ring group include a cyclopropyl group, a cyclopentyl group and a cyclohexyl group. These groups may be each a non-substituted group or may each have a substituent described later.

Examples of the aromatic hydrocarbon ring group (also called an aromatic hydrocarbon group, an aryl group or the like) include a phenyl group, a p-chlorophenyl group, a mesityl group, a tolyl group, a xylyl group, a naphthyl group, a anthryl group, an azulenyl group, an acenaphthenyl group, a fluorenyl group, a phenanthryl group, an indenyl group, a pyrenyl group and a biphenyl group.

These groups may be each a non-substituted group or may each have a substituent represented by Y1 in General Formula (1).

Examples of a heterocyclic group represented by Z in General Formula (5) include a non-aromatic heterocyclic group and an aromatic heterocyclic group. Examples of the non-aromatic heterocyclic group include an epoxy ring, an aziridine ring, a thiirane ring, an oxetane ring, an azetidine ring, a thietane ring, a tetrahydrofuran ring, a dioxorane ring, a pyrrolidine ring, a pyrazolidine ring, an imidazolidine ring, an oxazolidine ring, a tetrahydrothiophene ring, a sulforane ring, a thiazolidine ring, an ε-caprolactone ring, an ε-caprolactam ring, a piperidine ring, a hexahydropyridazine ring, a hexahydropyrimidine ring, a piperazine ring, a morpholine ring, a tetrahydropyrane ring, a 1,3-dioxane ring, a 1,4-dioxane ring, a trioxane ring, a tetrahydrothiopyrane ring, a thiomorpholine ring, a thiomorpholine-1,1-dioxide ring, a pyranose ring and a diazabicyclo[2,2,2]-octane ring.

These groups may be each a non-substituted group or may each have a substituent represented by Y1 in General Formula (1).

Examples of the aromatic heterocyclic group include a pyridyl group, a pyrimidinyl group, a furyl group, a pyrrolyl group, an imidazolyl group, a benzimidazolyl group, a pyrrazolyl group, a pyradinyl group, a triazolyl group (for example, a 1,2,4-triazole-1-yl group or a 1,2,3-triazole-1-yl group), an oxazolyl group, a benzoxazolyl group, a thiazolyl group, an isooxazolyl group, an isothiazolyl group, a furazanyl group, a thienyl group, a quinolyl group, a benzofuryl group, a dibenzofuryl group, a benzothienyl group, a dibenzothienyl group, an indolyl group, a carbazolyl group, a carbolinyl group, a diazacarbazolyl group (indicating a ring formed in such a manner that one of carbon atoms constituting a carboline ring of a carbolinyl group is substituted by a nitrogen atom), a quinoxalinyl group, a pyridazinyl group, a triazinyl group, a quinazolinyl group and a phthalazinyl group.

These groups may be each a non-substituted group or may each have a substituent represented by Y1 in General Formula (1).

The group represented by Z is preferably an aromatic hydrocarbon ring group or an aromatic heterocyclic group.

Examples of an aromatic hydrocarbon ring which is formed by A1 with P—C in General Formula (5) include a benzene ring, a biphenyl ring, a naphthalene ring, an azulene ring, an anthracene ring, a phenanthrene ring, a pyrene ring, a chrysene ring, a naphthacene ring, a triphenylene ring, an o-terphenyl ring, an m-terphenyl ring, a p-terphenyl ring, an acenaphthene ring, a coronene ring, a fluorene ring, a fluoranthrene ring, a naphthacene ring, a pentacene ring, a perylene ring, a pentaphene ring, a picene ring, a pyrene ring, a pyranthrene ring and an anthranthrene ring.

These rings may each have a substituent represented by Y1 in General Formula (1) too.

Examples of an aromatic heterocycle which is formed by A1 with P—C in General Formula (5) include a furan ring, a thiophene ring, an oxazole ring, a pyrrole ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, a thiazole ring, an indole ring, a benzimidazole ring, a benzothiazole ring, a benzoxazole ring, a quinoxaline ring, a quinazoline ring, a phthalazine ring, a carbazole ring, a carboline ring and an azacarbazole ring.

The azacarbazole ring indicates a ring formed in such a manner that at least one of carbon atoms of a benzene ring constituting a carbazole ring is substituted by a nitrogen atom.

These rings may each have a substituent represented by Y1 in General Formula (1) too.

A substituent represented by each of R01 and R02 in —C(R01)=C(R02)-, —N=C(R02)- and —C(R01)=N— which are represented by A3 in General Formula (5) is synonymous with the substituent represented by Y1 in General Formula (1).

Examples of a bidentate ligand represented by P1-L1-P2 in General Formula (5) include phenylpyridine, phenylpyrazole, phenylimidazole, phenyltriazole, phenyltetrazole, pyrazabole, acetylacetone and picolinic acid.

j1 represents an integer of one to three, and j2 represents an integer of zero to two, provided that the sum of j1 and j2 is two or three. In particular, j2 being zero is preferable.

A transition metal element (simply called a transition metal) of Groups 8 to 10 in the element periodic table represented by M1 in General Formula (5) is synonymous with the transition metal element represented by M1 in General Formula (4).

Specific examples of the phosphorescence emitting compound of the present invention are shown below. However, the present invention is not limited thereto.

[Chem. 6]

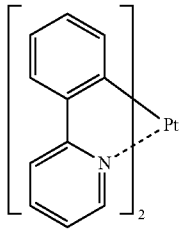
Pt-1

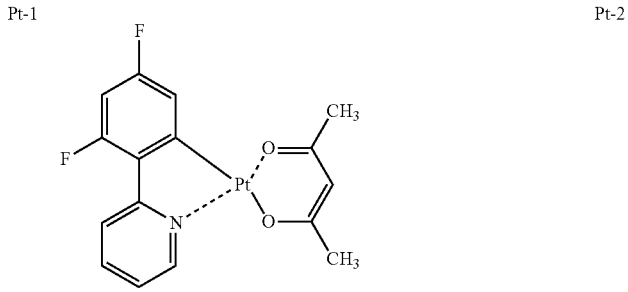
Pt-2

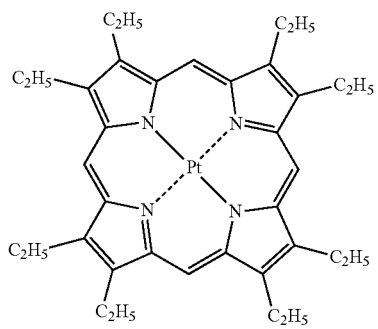
Pt-3

A-1
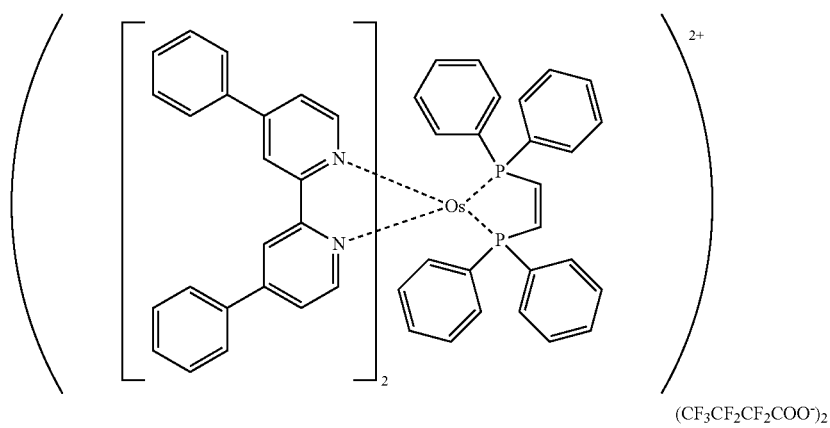
[Chem. 7]
Ir-1 Ir-2
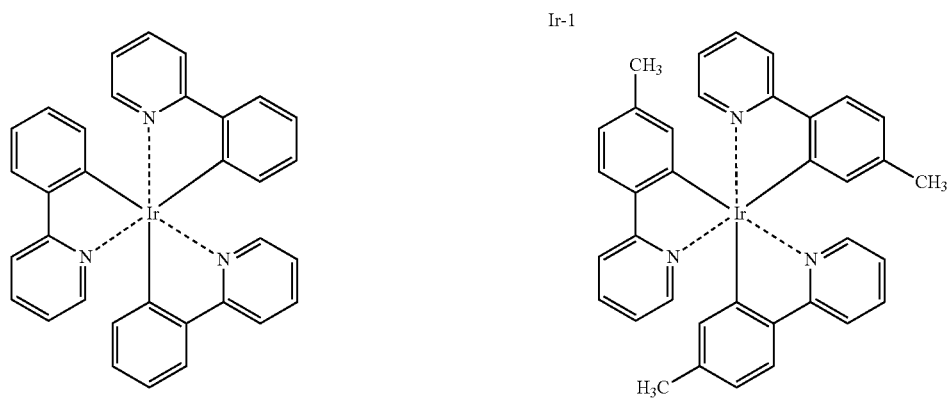
Ir-3 Ir-4
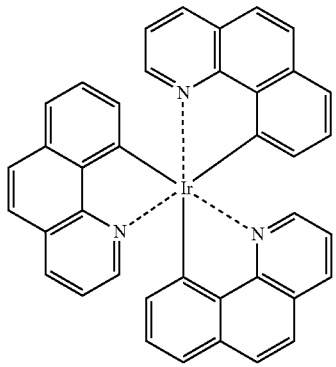 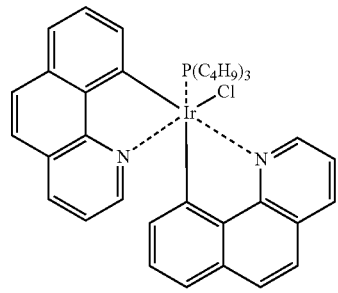
Ir-5 Ir-6
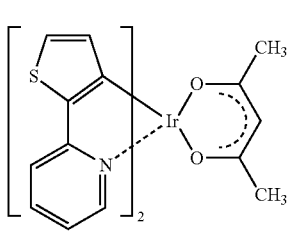 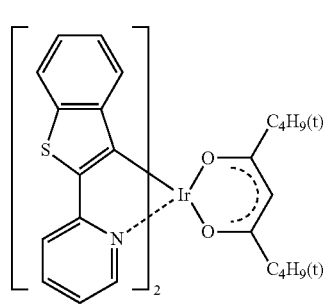

[Chem. 8]
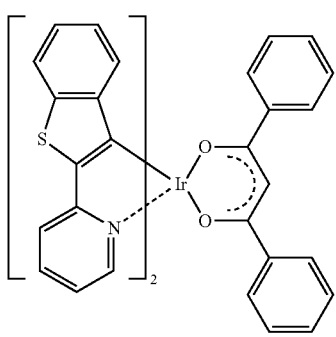
Ir-7
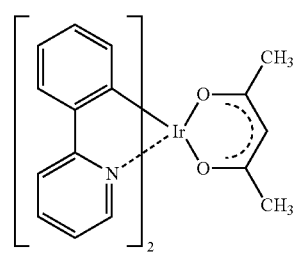
Ir-8
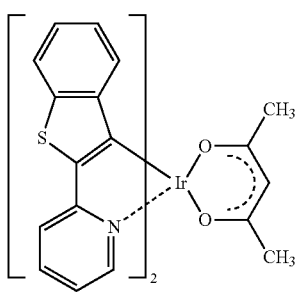
Ir-9
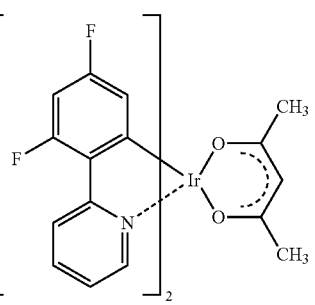
Ir-10
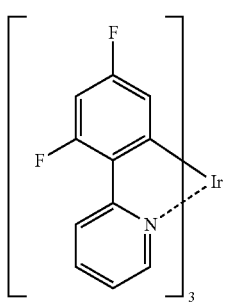
Ir-11
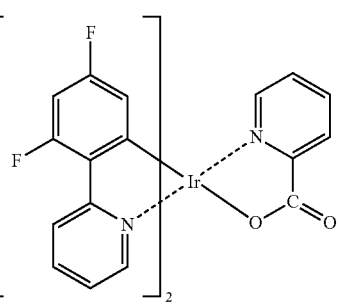
Ir-12
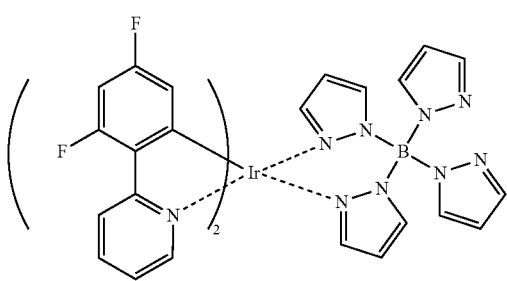
Ir-13
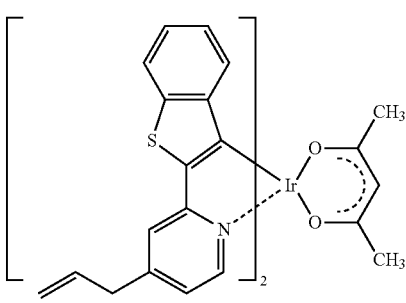
Ir-14
[Chem. 9]
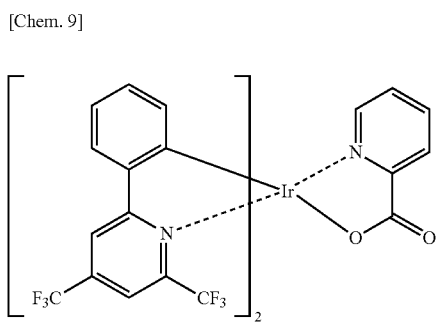
Ir-15
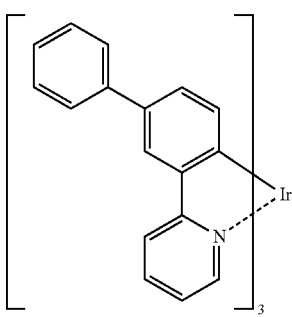
Ir-16

-continued
Ir-17
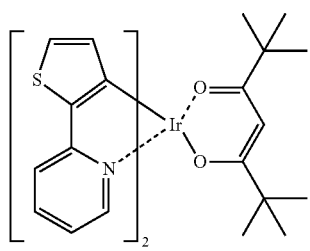
Ir-18
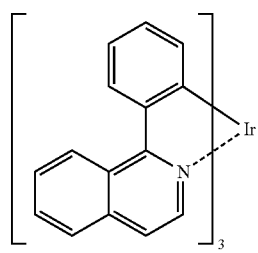
Ir-19
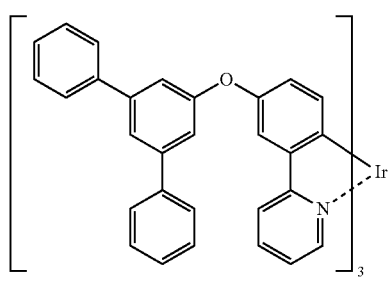
Ir-20
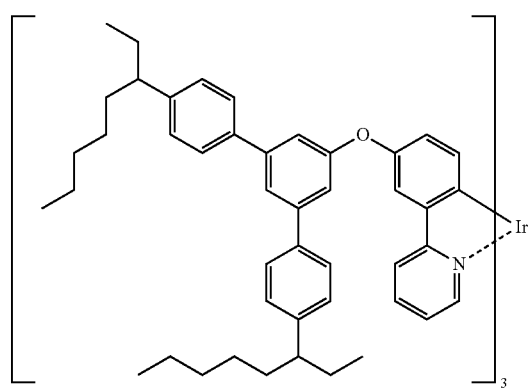
Ir-21
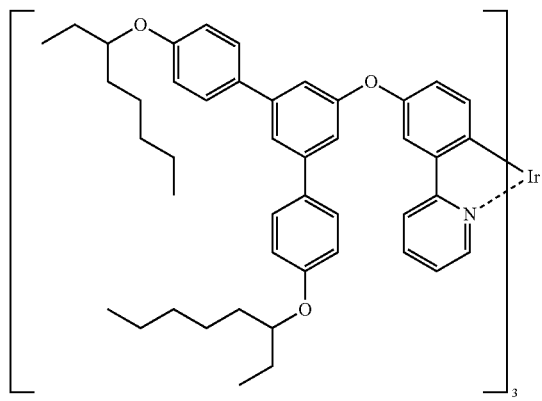
[Chem. 10]
Ir-22
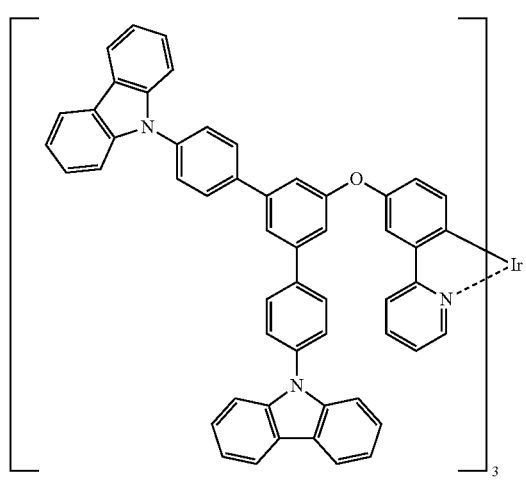
Ir-23
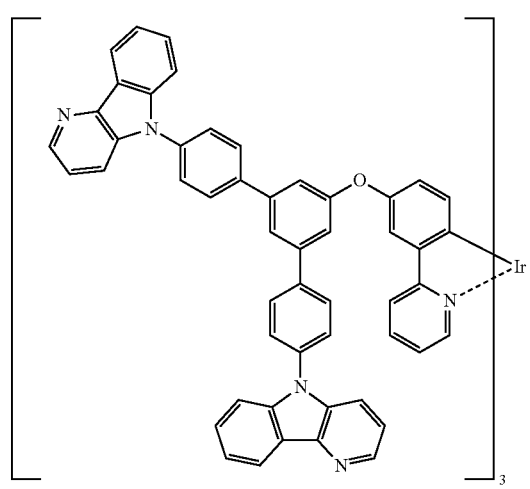

-continued
Ir-24 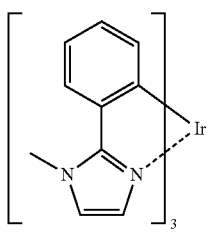
Ir-25 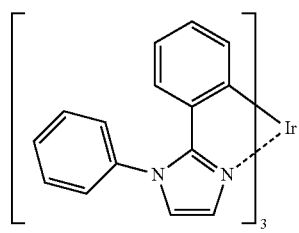
Ir-26 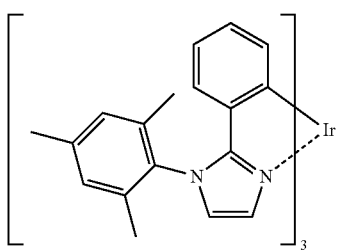
[Chem. 11]
Ir-27 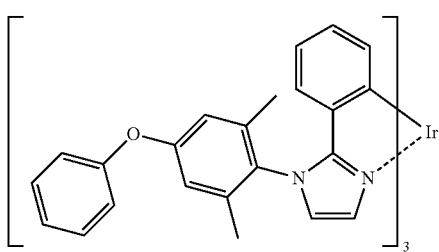
Ir-28 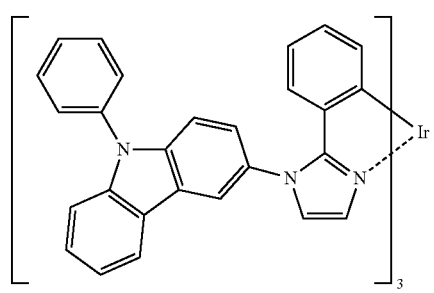
Ir-29 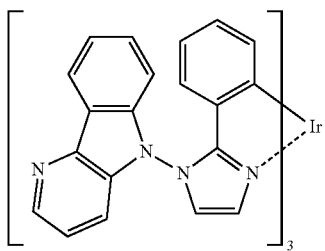
Ir-30 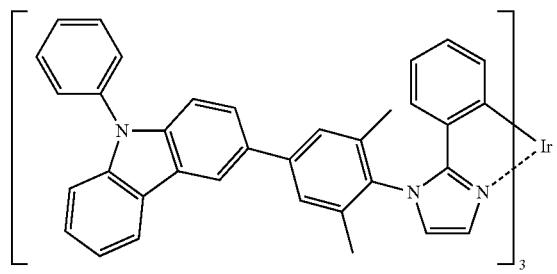
Ir-31 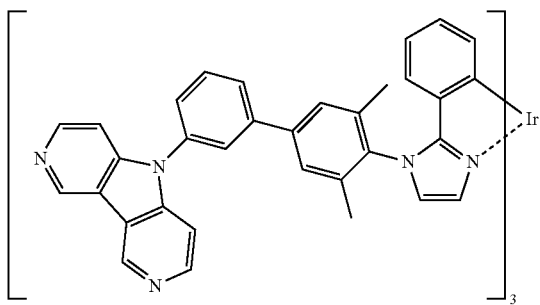

-continued
Ir-32
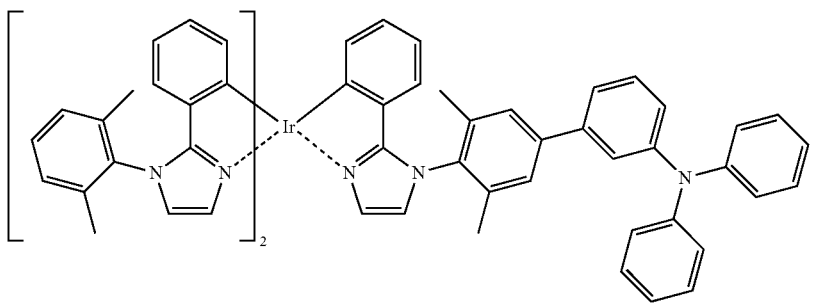
Ir-33
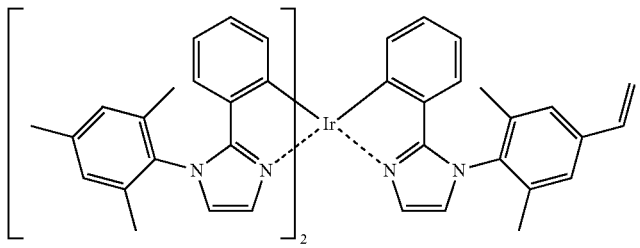
[Chem. 12]
Ir-34
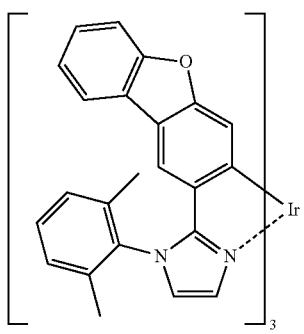
Ir-35
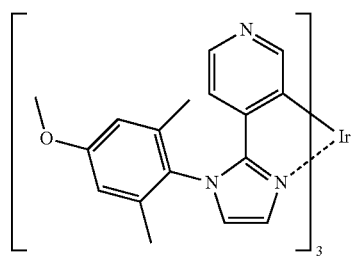
Ir-36
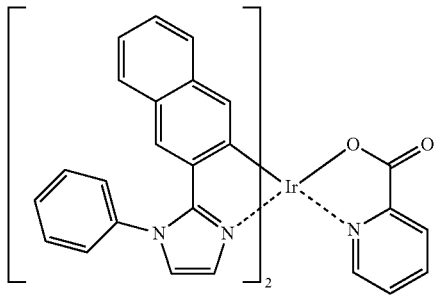
Ir-37
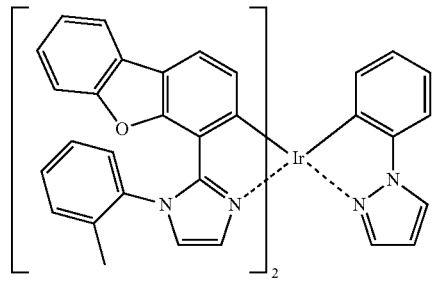
Ir-38
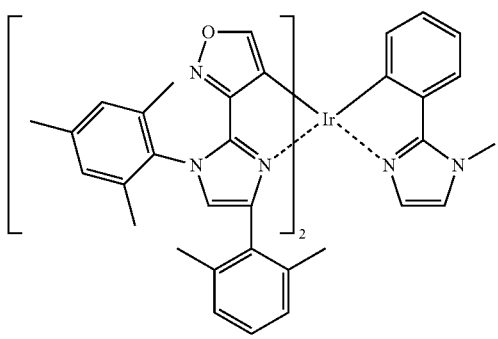
Ir-39
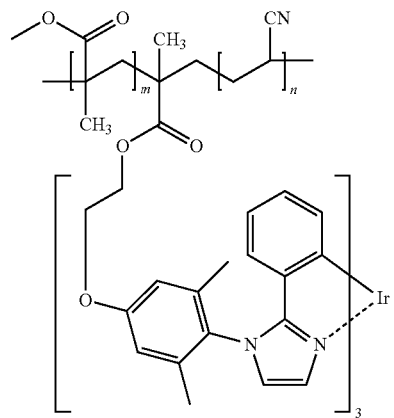

[Chem. 13]

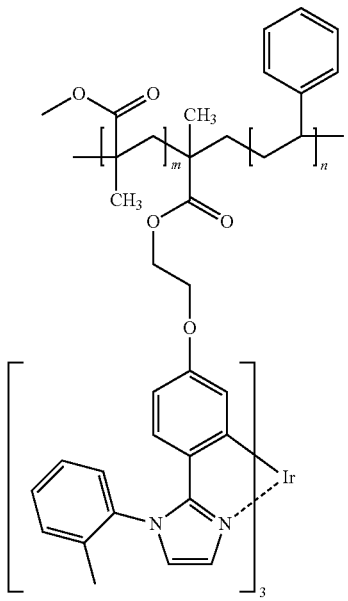

Ir-40

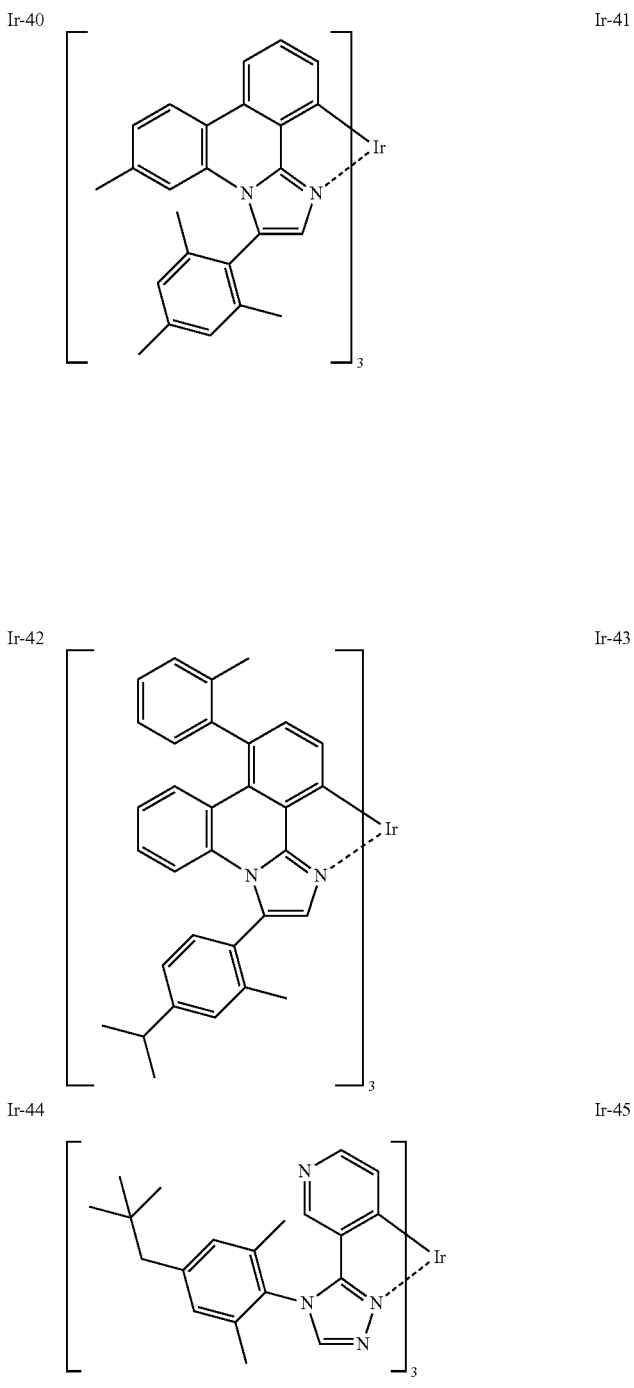

Ir-41, Ir-42, Ir-43, Ir-44, Ir-45

The above-mentioned phosphorescence emitting compounds (also called phosphorescence emitting metal complexes or the like) can be synthesized by employing methods described in documents such as Organic Letter, vol. 3, No. 16, pp. 2579-2581 (2001); Inorganic Chemistry, vol. 30, No. 8, pp. 1685-1687 (1991); J. Am. Chem. Soc., vol. 123, p. 4304 (2001); Inorganic Chemistry, vol. 40, No. 7, pp. 1704-1711 (2001); Inorganic Chemistry, vol. 41, No. 12, pp. 3055-3066 (2002); New Journal of Chemistry, vol. 26, p. 1171 (2002); and European Journal of Organic Chemistry, vol. 4, pp. 695-709 (2004); and reference documents described in these documents.

[Intermediate Layer]

The case where the non-luminescent intermediate layers (also called non-doped regions or the like) are provided in respective spaces between the light emitting layers is described.

The non-luminescent intermediate layer is a layer provided between the light emitting layers when a plurality of light emitting layers is provided. The thickness of the non-luminescent intermediate layer is preferably within a range from 1 to 20 nm and, in view of preventing interactions between its adjacent light emitting layers such as energy transfer and not giving a large load to current-voltage characteristics of the element, far preferably within a range from 3 to 10 nm.

A material used for the non-luminescent intermediate layer may be the same as or different from host compounds of the light emitting layers, preferably the same as the host material of at least one of two light emitting layers which are adjacent to the intermediate layer.

Thus, the non-luminescent intermediate layer may contain a compound (for example, a host compound) shared between the non-luminescent layer and the light emitting layers. The layers each containing a shared host material (here, using a shared host material indicates a case of using materials having the same physico-chemical property, examples of which include the phosphorescence emission energy and the glass transition temperature, or a case of using host compounds having the same molecular structure, for example) lowers an injection barrier between the light emitting layers and the non-luminescent layer and hence can produce an effect of easily keeping injection balance of positive holes and electrons even when changing a voltage (current). Further, the non-doped region using the host material having the physico-chemical property or molecular structure which is the same as that of the host compound contained in each of the light emitting layers can also solve an existing big problem in producing an organic EL element, namely, complexity in producing the element.

The host material is preferably a material having a carrier transport capability in order to transport carriers. As a physical property indicating the carrier transport capability, carrier mobility is used. However, the carrier mobility of an organic material depends on field intensity in general. Because a material having high field intensity dependence easily puts the injection/transport of positive holes and electrons out of balance, it is preferable that, as the intermediate layer material and the host material, a material having low field intensity dependence be used for the mobility.

Meanwhile, in order to optimally adjust injection balance of positive holes and electrons, it is also preferable that the non-luminescent intermediate layer function as a later-described block layer, namely, a positive hole block layer or an electron block layer.

[Injection Layer: Electron Injection Layer and Positive Hole Injection Layer]

The injection layer is provided as needed. Examples of the injection layer include an electron injection layer and a positive hole injection layer. As described above, the injection layers may be present: between an anode and a light emitting layer or a positive hole transfer layer; and between a cathode and the light emitting layer or an electron transport layer.

The injection layer is a layer disposed between an electrode and an organic layer to decrease a driving voltage and to improve brightness of light emitted, which is detailed in Part 2, Chapter 2 "Denkyoku Zairyo (Electrode Material)" (pp. 123-166) of "Yuki EL Soshi To Sono Kogyoka Saizensen (Organic EL Element and Front of Industrialization thereof) (Nov. 30, 1998, published by N. T. S Co., Ltd.)", and examples thereof include a positive hole injection layer and an electron injection layer.

The positive hole injection layer is also detailed in documents such as Japanese Patent Application Laid-Open Publication Nos. 9-45479, 9-260062 and 8-288069, and specific examples thereof include a phthalocyanine layer comprising such as copper phthalocyanine, an oxide layer comprising such as vanadium oxide, an amorphous carbon layer and a polymer layer employing conductive polymer such as polyaniline (emeraldine) or polythiophene.

The electron injection layer is also detailed in documents such as Japanese Patent Application Laid-Open Publication Nos. 6-325871, 9-17574 and 10-74586, and specific examples thereof include: a metal layer containing, for example, strontium or aluminum; an alkali metal halide layer containing, for example, potassium fluoride; an alkali earth metal compound layer containing, for example, magnesium fluoride; and an oxide layer containing, for example, molybdenum oxide. It is preferable that the electron injection layer of the present invention have a laminated structure of a metal layer and an alkali metal halide layer or a laminated structure of an oxide layer, a metal layer and an alkali metal halide layer, and metal oxide may be doped with alkali metal. The amount of alkali metal with which metal oxide is doped is preferably within a range from 1 to 10 mass %. In addition, it is preferable that the electron injection layer be a very thin film, and the thickness thereof be within a range from 1 nm to 10 μm although it depends on the material thereof.

[Block Layer: Positive Hole Block Layer and Electron Block Layer]

The block layer is provided as needed in addition to the basic constituent layers of thin organic compound films described above. Examples thereof include a positive hole block layer described in documents such as Japanese Patent Application Laid-Open Publication Nos. 11-204258 and 11-204359 and p. 273 of "Yuki EL Soshi To Sono Kogyoka Saizensen (Organic EL Element and Front of Industrialization thereof) (Nov. 30, 1998, published by N. T. S Co., Ltd.)".

The positive hole block layer has a function of an electron transport layer in a broad sense by being made of a positive hole block material having a function to transport electrons with a very little capability to transport positive holes and can increase recombination probability of electrons and positive holes by blocking positive holes while transporting electrons. Further, as needed, the constitution of an electron transport layer described later can be applied to the positive hole block layer of the present invention. It is preferable that the positive hole block layer be disposed adjacent to the light emitting layer.

On the other hand, the electron block layer has a function of a positive hole transport layer in a broad sense by being made of a material having a function to transport positive holes with a very little capability to transport electrons and can increase the recombination probability of electrons and positive holes by blocking electrons while transporting positive holes. Further, as needed, the constitution of a positive hole transport layer described later can be applied to the electron block layer. The thickness of the positive hole block layer of the present invention is preferably within a range from 3 to 100 nm and far preferably within a range from 5 to 30 nm.

[Positive Hole Transport Layer]

The positive hole transport layer is made of a positive hole transport material having a function to transport positive holes, and, in a broad sense, a positive hole injection layer and an electron block layer are of the positive hole transport layer. One positive hole transport layer or a plurality of positive hole transport layers can be provided.

The positive hole transport material is a material having a capability to inject or transport positive holes or a barrier property against electrons and is either organic or inorganic. Examples thereof include a triazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline type copolymer and a conductive oligomer such as a thiophene oligomer.

As the positive hole transport material, those described above can be used. However, it is preferable to use a porphyrin compound, an aromatic tertiary amine compound or a styrylamine compound and far preferable to use an aromatic tertiary amine compound.

Typical examples of the aromatic tertiary amine compound and the styrylamine compound include: N,N,N',N'-tetraphenyl-4,4'-diaminophenyl;

N,N'-diphenyl-N,N'-bis(3-methylphenyl)-[1,1'-biphenyl]-4, 4'-diamine (TDP); 2,2-bis(4-di-p-tolylaminophenyl)propane; 1,1-bis(4-di-p-tolylaminophenyl)cyclohexane;

N,N,N',N'-tetra-p-tolyl-4,4'-diaminobiphenyl; 1,1-bis(4-di-p-tolylaminophenyl)-4-phenylcyclohexane;

bis(4-dimethylamino-2-methyl)phenylmethane;
bis(4-di-p-tolylaminophenyl)phenylmethane;
N,N'-diphenyl-N,N'-di(4-methoxyphenyl)-4,4'-diaminobiphenyl; N,N,N',N'-tetraphenyl-4,4'-diaminodiphenylether; 4,4'-bis(diphenylamino)quadriphenyl;
N,N,N-tri(p-tolyl)amine;
4-(di-p-tolylamino)-4'-[4-(di-p-tolylamino)styryl]stilbene;
4-N, N-diphenylamino-(2-diphenylvinyl)benzene;
3-methoxy-4'-N,N-diphenylaminostilbene; N-phenylcarbazole; those having two condensed aromatic rings in a molecule described in U.S. Pat. No. 5,061,569, such as 4,4'-bis[N-(1-naphthyl)-N-phenylamino]biphenyl (NDP); and 4,4',4''-tris[N-(3-methylphenyl)-N-phenylamino]triphenylamine (MTDATA) in which three triphenylamine units are bonded in a star burst form described in Japanese Patent Application Laid-Open Publication No. 4-308688.

Polymer materials in each of which any of these materials is introduced into a polymer chain or constitutes a main chain of a polymer can also be used. Further, inorganic compounds such as a p type-Si and a p type-SiC can also be used as the positive hole injection material and the positive hole transport material Further, it is also possible to use so-called p type positive hole transport materials described in documents such as Japanese Patent Application Laid-Open Publication No. 11-251067 and Applied Physics Letters 80 (2002), p. 139 by J. Huang et. al. In the present invention, it is preferable to use these materials in view of producing a light emitting element having high efficiency.

The positive hole transport layer can be formed by making the above-mentioned positive hole transport material a thin film by a well-known method such as the vacuum evaporation method, the spin coating method, the casting method, the printing method including the ink-jet method or the LB method. The thickness of the positive hole transport layer is not particularly limited, but it is generally within a range about from 5 nm to 5 μm, preferably within a range from 5 nm to 200 nm. This positive hole transport layer may have a single layer structure composed of one type or two or more types of the above-mentioned materials.

Further, a positive hole transport layer having high p property doped with impurities can be employed as the positive hole transport layer. Examples thereof include those described in documents such as Japanese Patent Application Laid-Open Publication Nos. 4-297076, 2000-196140 and 2001-102175 and J. Appl. Phys., 95, 5773 (2004).

Employing a positive hole transport layer having high p property is preferable in view of producing an element which consumes lower electric power.

[Electron Transport Layer]

The electron transport layer is made of a material having a function to transport electrons, and, in a broad sense, an electron injection layer and a positive hole block layer are of the electron transport layer. One electron transport layer or a plurality of electron transport layers can be provided.

In general, an electron transport material (which is also a positive hole block material) used for, in the case of one electron transport layer being provided, the electron transport layer, and in the case of a plurality of electron transport layers being provided, an electron transport layer adjacent to a cathode side of a light emitting layer, has a function to transfer electrons injected from the cathode to the light emitting layer.

It is preferable that the electron transport layer of the present invention contain a compound represented by General Formula (1).

<<Compound Represented by General Formula (1)>>

The compound represented by General Formula (1) of the present invention is described.

Examples of a substituent represented by Y1 in General Formula (1) include: an alkyl group (for example, a methyl group, an ethyl group, a propyl group, an isopropyl group, a tert-butyl group, a pentyl group, a hexyl group, an octyl group, a dodecyl group, a tridecyl group, a tetradecyl group and a pentadecyl group); a cycloalkyl group (for example, a cyclopentyl group and a cyclohexyl group); an alkenyl group (for example, a vinyl group and an allyl group); an alkynyl group (for example, an ethynyl group and a propargyl group); an aromatic hydrocarbon group (also called an aromatic carbon ring group, an aryl group or the like, for example; a phenyl group, a p-chlorophenyl group, a mesityl group, a tolyl group, a xylyl group, a naphthyl group, an anthryl group, an azulenyl group, an acenaphthenyl group, a fluorenyl group, a phenanthryl group, an indenyl group, a pyrenyl group and a biphenyryl group); an aromatic heterocyclic group (for example, a furyl group, a thienyl group, a pyridyl group, a pyridazinyl group, a pyrimidinyl group, a pyrazinyl group, a triazinyl group, an imidazolyl group, a pyrazolyl group, a thiazolyl group, a quinazolinyl group, a carbazolyl group, a carbolinyl group, a diazacarbazolyl group (which is a group formed in such a manner that one of carbon atoms constituting a carboline ring of a carbolinyl group is substituted by a nitrogen atom) and a phtharazinyl group); a heterocyclic group (for example, a pyrrolidyl group, an imidazolidyl group, a morpholyl group, and an oxazolidyl group); an alkoxy group (for example, a methoxy group, an ethoxy group, a propyloxy group, a pentyloxy group, an hexyloxy group, an octyloxy group and a dodecyloxy group); a cycloalkoxy group (for example, a cyclopentyloxy group and a cyclohexyloxy group); an aryloxy group (for example, a phenoxy group and a naphthyloxy group); an alkylthio group (for example, a methylthio group, an ethylthio group, a propylthio group, a pentylthio group, a hexylthio group, an octylthio group and a dodecylthio group); a cycloalkylthio group (for example, a cyclopentylthio group and a cyclohexylthio group); an arylthio group (for example, a phenylthio group and a naphthylthio group); an alkoxycarbonyl group (for example, a methyloxycarbonyl group, an ethyloxycarbonyl group, a butyloxycarbonyl group, an octyloxycarbonyl group and a dodecyloxycarbonyl group); an aryloxycarbonyl group (for example, a phenyloxycarbonyl group and a naphthyloxycarbonyl group); a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group and a 2-pyridylaminosulfonyl group); an acyl group (for example, an acetyl group, an ethylcarbonyl group, a propylcarbonyl group, a pentylcarbonyl group, cyclohexylcarbonyl group, an octylcarbonyl group, a 2-ethylhexylcarbonyl group, a dodecylcarbonyl group, a phenylcarbonyl group, a naphthylcarbonyl group and a pyridylcarbonyl group); an acyloxy group (for example, an acetyloxy group, an ethylcarbonyloxy group, a butylcarbonyloxy group, an octylcarbonyloxy group, a dodecylcarbonyloxy group and a phenylcarbonyloxy group); an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group and a naphthylcarbonylamino group); a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl gropup, a phenylaminocarbonyl group, a naphthylaminocarbonyl group and a 2-pyridylaminocarbonyl group); an ureido group (for example, a methylureido group, an ethylureido group, a pentylureido group, a cyclohexylureido group, an octylureido group, a dodecylureido group, a phenylureido group, a naphthylureido group and a 2-pyridylaminoureido group); a sulfinyl group (for example, a methylsulfinyl group, an ethylsulfinyl group, a butylsulfinyl group, a cyclohexylsulfinyl group, a 2-ethylhexylsulfinyl group, a dodecylsulfinyl group, a phenylsulfinyl group, a naphthylsulfinyl group and a 2-pyridylsulfinyl group); an alkylsulfonyl group (for example, a methylsulfonyl group, an ethylsulfonyl group, a butylsulfonyl group, a cyclohexylsulfonyl group, a 2-ethylhexylsulfonyl group and a dodecylsulfonyl group); an arylsulfonyl group or a heteroarylsulfonyl group (for example, a phenylsulfonyl group, a naphthylsulfonyl group and a 2-pyridylsulfonyl group); an amino group (for example, an amino group, an ethylamino group, a dimethylamino group, a butylamino group, a cyclopentylamino group, a 2-ethylhexylamino, a dodecylamino group, an anilino group, a naphthylamino group, a 2-pyridylamino group, a piperidyl group (also called a piperidinyl group) and a 2,2,6,6-tetramethyl piperidinyl group); a halogen atom (for example, a fluorine atom, a chlorine atom and a bromine atom); a fluorohydrocarbon group (for example, a fluoromethyl group, a trifluoromethyl group, a pentafluoroethyl group and a pentafluorophenyl group); a cyano group; a nitro group; a hydroxyl group; a mercapto group; a silyl group (for example, a trimethylsilyl group, a triisopropylsilyl group, a triphenylsilyl group and a phenyldiethylsilyl group); a phosphate group (for example, dihexylphosphoryl group); a phosphite group (for example, diphenylphosphinyl group); and a phosphono group.

These substituents may be further substituted by the above-mentioned substituents. Also, two or more of these substituents may combine to form a ring.

Specific examples of an n1-valent linking group represented by Y1 in General Formula (1) include a divalent linking group, a trivalent linking group and a tetravalent linking group.

Examples of the divalent linking group represented by Y1 in General Formula (1) include: an alkylene group (for example, an ethylene group, a trimethylene group, a tetramethylene group, a propylene group, an ethylethylene group, a pentamethylene group, a hexamethylene group, a 2,2,4-trimethylhexamethylene group, a heptamethylene group, an octamethylene group, nonamethylene group, a decamethylene group, an undecamethylene group, a dodecamethylene group, a cyclohexylene group (for example, a 1,6-cyclohexanediyl group) and a cyclopenthylene group (for example, a 1,5-cyclopentanediyl group)); an alkenylene group (for example, a vinylene group, a propenylene group, a butenylene group, a pentenylene group, a 1-methylvinylene group, a 1-methylpropenylene group, a 2-methylpropenylene group, a 1-methylpentenylene group, a 3-methylpentenylene group, a 1-ethylvinylene group, a 1-ethylpropenylene group, a 1-ethylbutenylene group and a 3-ethylbutenylene group); an alkynylene group (for example, an ethynylene group, a 1-propynylene group, a 1-butynylene group, a 1-pentynylene group, a 1-hexynylene group, a 2-butynylene group, a 2-pentynylene group, a 1-methylethynylene group, a 3-methyl-1-propynylene group and a 3-methyl-1-butynylene group); an arylene group (for example, an o-phenylene group, a p-phenylene group, a naphthalenediyl group, an anthracenediyl group, a naphthacenediyl group, a pyrenediyl group, a naphthylnaphthalenediyl group, a biphenyldiyl group (for example, a [1,1'-biphenyl]-4,4'-diyl group, a 3,3'-biphenyldiyl group and a 3,6-biphenyldiyl group), a terphenyldiyl group, a quaterphenyldiyl group, a quinquephenyldiyl group, a sexiphenyldiyl group, a septiphenyldiyl group, an octiphenyldiyl group, a nobiphenyldiyl group and a deciphenyldiyl group); a heteroarylene group (for example, a divalent group derived from a group consisting of a carbazole group, a carboline ring, a diazacarbazole ring (also called a monoazacarboline group, indicating a ring formed in such a manner that one of carbon atoms constituting a carboline ring is substituted by a nitrogen atom), a triazole ring, a pyrrole ring, a pyridine ring, a pyrazine ring, a quinoxaline ring, a thiophene ring, an oxadiazole ring, a dibenzofuran ring, a dibenzothiophene ring and an indole ring), a chalcogen atom such as oxygen or sulfur and a group derived from a condensed aromatic heterocycle formed in such a manner that three or more rings are condensed (the condensed aromatic heterocycle formed in such a manner that three or more rings are condensed preferably contains a hetero atom selected from N, O and S as an element constituting a condensed ring; for example, an acridine ring, a benzoquinoline ring, a carbazole ring, a phenazine ring, a phenanthridine ring, a phenanthroline ring, a carboline ring, a cycladine ring, a quindoline ring, a thebenidine ring, a quinindoline ring, a triphenodithiazine ring, a triphenodioxazine ring, a phenanthrazine ring, an anthrazine ring, a perimizine ring, a diazacarbazole ring (indicating a ring formed in such a manner that one of carbon atoms constituting a carboline ring is substituted by a nitrogen atom), a phenanthroline ring, a dibenzofuran ring, a dibenzothiophene ring, a naphthofuran ring, a naphthothiophene ring, a benzodifuran ring, a benzodithiophene ring, a naphthodifuran ring, a naphthodithiophene ring, an anthrafuran ring, an anthradifuran ring, an anthrathiophene ring, an anthradithiophene ring, a thianthrene ring, a phenoxathiin ring and a thiophanthrene ring (naphthothiophene ring)).

Examples of the trivalent linking group represented by Y1 in General Formula (1) include an ethanetriyl group, a propanetriyl group, a butanetriyl group, a pentanetriyl group, a hexanetriyl group, a heptanetriyl group, an octanetriyl group, a nonanetriyl group, a decanetriyl group, an undecanetriyl group, a dodecanetriyl group, a cyclohexanetriyl group, a cyclopentanetriyl group, a benzenetriyl group, a naphthalenetriyl group, a pyridinetriyl group and a carbazoletriyl group.

The tetravalent linking group represented by Y1 in General Formula (1) is a group which has an additional linking group to any of the above-mentioned trivalent linking groups. Examples of the tetravalent linking group include a propandiylidene group, a 1,3-propandiyl-2-ylidene group, a butanediylidene group, a pentanediylidene group, a hexanediylidene group, a heptanediylidene group, an octanediylidene group, a nonanediylidene group, a decanediylidene group, an undecanediylidene group, a dodecanediylidene group, a cyclohexanediylidene group, a cyclopentanediylidene group, a benzenetetrayl group, a naphthalenetetrayl group, a pyridinetetrayl group and a carbazoletetrayl group.

The above-mentioned divalent, trivalent and tetravalent linking groups may each have a substituent represented by Y1 in General Formula (1) too.

In the compound represented by General Formula (1), it is preferable that Y1 represent a group which is derived from the condensed aromatic heterocycle formed in such a manner that three or more rings are condensed, and the condensed aromatic heterocycle formed in such a manner that three or more rings are condensed be a dibenzofuran ring or a dibenzothiophene ring. Further, n1 being 2 or more is preferable.

Further, the compound represented by General Formula (1) has in a molecule at least two condensed aromatic heterocyclic groups each formed in such a manner that three or more rings are condensed.

When Y1 represents an n1-valent linking group, Y1 is preferably non-conjugated in order to keep the triplet excitation energy of the compound represented by General Formula (1) high and is constituted of aromatic rings (an aromatic hydrocarbon ring+an aromatic heterocycle) in order to improve Tg (also called glass transition point or glass transition temperature).

Here, the "non-conjugated" indicates that a linking group cannot be expressed with alternation of single and double bonds, or that a conjugation of aromatic rings which constitute a linking group is sterically broken.

(Group Represented by General Formula (A))

General Formula (A) represents Ar1 in General Formula (1).

Substituents represented by R, R' or R1 in N(R) or Si(R)(R') represented by X and in C(R1) represented by each of E1 to E8 in General Formula (A) are each synonymous with the substituent represented by Y1 in General Formula (1).

A divalent linking group represented by Y2 in General Formula (A) is synonymous with the divalent linking group represented by Y1 in General Formula (1).

Examples of a five-membered or six-membered aromatic ring which is used to form a group derived from a five-membered or six-membered aromatic ring represented by each of Y3 and Y4 in General Formula (A) include a benzene ring, an oxazole ring, a thiophene ring, a furan ring, a pyrrole ring, a pyridine ring, a pyridazine ring, a pyrimidine ring, a pyrazine ring, a diazine ring, a triazine ring, an imidazole ring, an isoxazole ring, a pyrazole ring and a triazole ring.

At least one of the groups derived from five-membered or six-membered aromatic rings respectively represented by Y3 and Y4 is a group derived from an aromatic heterocycle containing a nitrogen atom as a ring constituent atom. Examples of the aromatic heterocycle containing a nitrogen atom as a ring constituent atom include an oxazole ring, a pyrrole ring, a pyridine ring, a pyridazine ring, a pyrimidine ring, a pyrazine ring, the diazine ring, a triazine ring, an imidazole ring, an isoxazole ring, a pyrazole ring and a triazole ring.

(Preferred Group Represented by Y3)

In General Formula (A), the group represented by Y3 is preferably a group derived from the above-mentioned six-membered aromatic ring and far preferably a group derived from a benzene ring.

(Preferred Group Represented by Y4)

In General Formula (A), the group represented by Y4 is preferably a group derived from the above-mentioned six-membered aromatic ring and far preferably a group derived from the aromatic heterocycle containing a nitrogen atom as a ring constituent atom, in particular, a group derived from a pyridine ring.

(Preferred Group Represented by General Formula (A))

The group represented by General Formula (A) is preferably a group represented by one of General Formulae (A-1), (A-2), (A-3) and (A-4).

[Chem. 14]

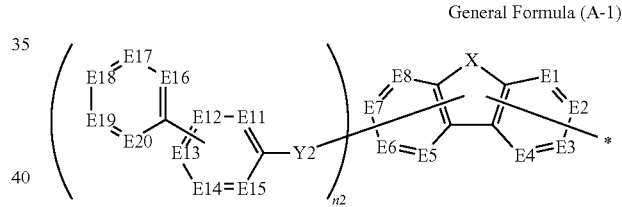

General Formula (A-1)

In the formula, X represents N(R), O, S or Si(R)(R'), E1 to E8 each represent C(R1) or N, and R, R' and R1 each represent a hydrogen atom, a substituent or a linking site with Y1; Y2 represents a bond or a divalent linking group; E11 to E20 each represent C(R2) or N, and R2 represents a hydrogen atom, a substituent or a linking site, provided that at least one of E11 to E20 represents N, and at least one of E11 and E12 represents C(R2) and R2 represents a linking site; n2 represents an integer of one to four; and * represents a linking site with Y1 in General Formula (1).

[Chem. 15]

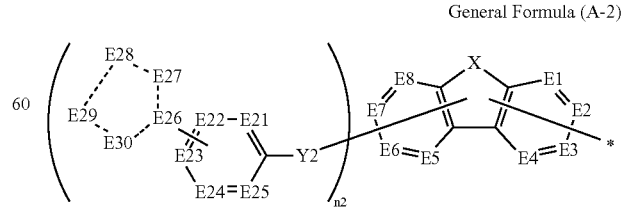

General Formula (A-2)

In the formula, X represents N(R), O, S or Si(R)(R'), E1 to E8 each represent C(R1) or N, and R, R' and R1 each represent a hydrogen atom, a substituent or a linking site with Y1; Y2 represents a bond or a divalent linking group; E21 to E25 each represent C(R2) or N, E26 to E30 each represent C(R2), N, O, S or Si(R3)(R4), R2 represents a hydrogen atom, a substituent or a linking site, and R3 and R4 each represent a hydrogen atom or a substituent, provided that at least one of E21 to E30 represents N, and at least one of E21 and E22 represents C(R2) and R2 represents a linking site; n2 represents an integer of one to four; * represents a linking site with Y1 in General Formula (1); and a broken line represents a single bond or a double bond.

[Chem. 16]

General Formula (A-3)

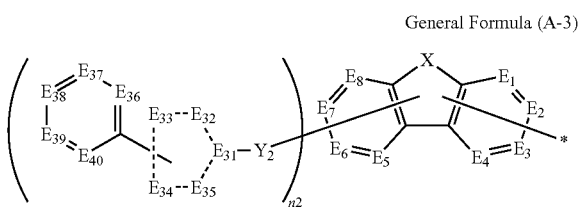

In the formula, X represents N(R), O, S or Si(R)(R'), $E_1$ to $E_8$ each represent C(R1) or N, and R, R' and R1 each represent a hydrogen atom, a substituent or a linking site with Y1; $Y_2$ represents a bond or a divalent linking group; $E_{31}$ to $E_{35}$ each represent C(R2), N, O, S or Si(R3)(R4), $E_{36}$ to $E_{40}$ each represent C(R2) or N, R2 represents a hydrogen atom, a substituent or a linking site, and R3 and R4 each represent a hydrogen atom or a substituent, provided that least one of $E_{31}$ to $E_{40}$ represents N, and at least one of $E_{32}$ and $E_{33}$ represents —C(R2)= and R2 represents a linking site; n2 represents an integer of one to four; * represents a linking site with Y1 in General Formula (1); and a broken line represents a single bond or a double bond.

[Chem. 17]

General Formula (A-4)

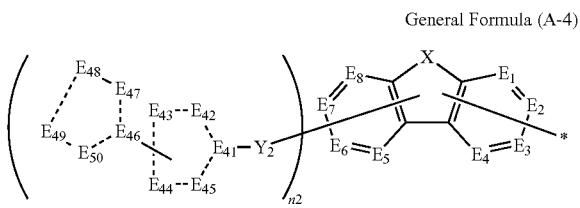

In the formula, X represents N(R), O, S or Si(R)(R'), $E_1$ to $E_8$ each represent C(R1) or N, and R, R' and R1 each represent a hydrogen atom, a substituent or a linking site with Y1; Y2 represents a bond or a divalent linking group; $E_{41}$ to $E_{50}$ each represent C(R2), N, O, S or Si(R3)(R4), R2 represents a hydrogen atom, a substituent or a linking site, and R3 and R4 each represent a hydrogen atom or a substituent, provided that at least one of $E_{41}$ to $E_{50}$ represents N, and at least one of $E_{42}$ and $E_{43}$ represents C(R2) and R2 represents a linking site; n2 represents an integer of one to four; * represents a linking site with Y1 in General Formula (1); and a broken line represents a single bond or a double bond.

The group represented by any one of General Formulae (A-1) to (A-4) is described below.

A substituent represented by each of R, R' and R1 in N(R) and Si(R)(R') represented by X and in C(R1) represented by each of E1 to E8 of the group represented by any one of General Formulae (A-1) to (A-4) is synonymous with the substituent represented by Y1 in General Formula (1).

A divalent linking group represented by Y2 of the group represented by any one of General Formulae (A-1) to (A-4) is synonymous with the divalent linking group represented by Y1 in General Formula (1).

A substituent represented by R2 in C(R2) represented by each of E11 to E20 in General Formula (A-1), each of E21 to E30 in General Formula (A-2), each of $E_{31}$ to $E_{40}$ in General Formula (A-3) or each of $E_{41}$ to $E_{50}$ in General Formula (A-4) is synonymous with the substituent represented by Y1 in General Formula (1).

It is preferable that the electron transport layer of the present invention contain a compound represented by General Formula (2).

<<Compound Represented by General Formula (2)>>

In the present invention, of the compounds represented by General Formula (1), the compound represented by General Formula (2) is preferable. The compound represented by General Formula (2) is described below.

An arylene group and a heteroarylene group represented by Y5 in General Formula (2) are synonymous with the arylene group and the heteroarylene group mentioned as examples of the divalent linking group represented by Y1 in General Formula (1), respectively.

It is preferable that a divalent linking group which is an arylene group, a heteroarylene group or a combination thereof represented by Y5 contain, of the heteroarylene groups, a group which is derived from a condensed aromatic heterocycle formed in such a manner that three or more rings are condensed, and the group derived from the condensed aromatic heterocycle formed in such a manner that three or more rings are condensed be a group derived from a dibenzofuran ring or a group derived from a dibenzothiophene ring.

A substituent represented by R3 in C(R3) represented by each of E51 to E56 in General Formula (2) is synonymous with the substituent represented by Y1 in General Formula (1).

In General Formula (2), it is preferable that as groups represented by E51 to E66, six or more among E51 to E58 and six or more among E59 to E66 each represent C(R3).

Examples of an aromatic hydrocarbon ring which is used to form a group derived from an aromatic hydrocarbon ring represented by each of Y6 to Y9 in General Formula (2) include a benzene ring, a biphenyl ring, a naphthalene ring, an azulene ring, an anthracene ring, a phenanthrene ring, a pyrene ring, a chrysene ring, a naphthacene ring, a triphenylene ring, an o-terphenyl ring, an m-terphenyl ring, a p-terphenyl ring, an acenaphthene ring, a coronene ring, a fluorene ring, a fluoranthrene ring, a naphthacene ring, a pentacene ring, a perylene ring, a pentaphene ring, a picene ring, a pyrene ring, a pyranthrene ring and an anthranthrene ring.

The aromatic hydrocarbon ring may have a substituent represented by Y1 in General Formula (1) too.

Examples of an aromatic heterocycle which is used to form a group derived from an aromatic heterocycle represented by each of Y6 to Y9 include a furan ring, a thiophene ring, an oxazole ring, a pyrrole ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, a thiazole ring, an indole ring, an indazole ring, a benzimidazole ring, a benzothiazole ring, a benzoxazole ring, a quinoxaline ring, a quinazoline ring, a cinnoline ring, a quinoline ring, an isoquinoline ring, a phthalazine ring naphthylidine ring, a carbazole ring, a carboline ring and a diazacarbazole ring (indicating a ring formed in such a manner that one of carbon atoms constituting a carboline ring is substituted by a nitrogen atom).

The aromatic heterocycle may have a substituent represented by Y1 in General Formula (1) too.

Examples of an aromatic heterocycle containing an N atom which is used to form a group derived from an aromatic heterocycle containing an N atom represented by each of at least one of Y6 and Y7 and at least one of Y8 and Y9 in General Formula (2) include an oxazole ring, a pyrrole ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, a thiazole ring, an indole ring, an indazole ring, a benzimidazole ring, a benzothiazole ring, a benzoxazole ring, a quinoxaline ring, a quinazoline ring, a cinnoline ring, a quinoline ring, an isoquinoline ring, a phthalazine ring, a naphthylidine ring, a carbazole ring, a carboline ring and a diazacarbazole ring (indicating a ring formed in such a manner that one of carbon atoms constituting a carboline ring is substituted by a nitrogen atom).

In General Formula (2), it is preferable that the groups represented by Y7 and Y9 be each a group derived from a pyridine ring.

In General Formula (2), it is preferable that the groups represented by Y6 and Y8 be each a group derived from a benzene ring.

It is far preferable that the electron transport layer of the present invention contain a compound represented by General Formula (3).

<<Compound Represented by General Formula (3)>>

The compound represented by General Formula (3) is described below.

An arylene group and a heteroarylene group represented by Y5 in General Formula (3) are synonymous with the arylene group and the heteroarylene group mentioned as examples of the divalent linking group represented by Y1 in General Formula (1), respectively.

It is preferable that a divalent linking group which is an arylene group, a heteroarylene group or a combination thereof represented by Y5 contain, of the heteroarylene groups, a group which is derived from a condensed aromatic heterocycle formed in such a manner that three or more rings are condensed, and the group derived from the condensed aromatic heterocycle formed in such a manner that three or more rings are condensed be a group derived from a dibenzofuran ring or a group derived from a dibenzothiophene ring.

Substituents represented by R3 in —C(R3)= represented by each of E51 to E66 and each of E71 to E78 in General Formula (3) are each synonymous with the substituent represented by Y1 in General Formula (1).

In General Formula (3), it is preferable that six or more among E51 to E58 and six or more among E59 to E66 each represent C(R3).

In General Formula (3), it is preferable that at least one of E75 to E79 and at least one of E84 to E88 each represent —N=.

In General Formula (3), it is preferable that one of E75 to E79 and one of E84 to E88 each represent N.

In General Formula (3), it is preferable that E71 to E74 and E80 to E83 each represent C(R3).

Further, in the compound represented by General Formula (2) or General Formula (3), it is preferable that E53 represent C(R3) and R3 thereof represent a liking site, and far preferable that E61 represent C(R3) and R3 thereof represent a liking site too.

Further, it is preferable that E75 and E84 each represent N, and far preferable that E71 to E74 and E80 to E83 each represent C(R3).

Specific examples of the compound represented by General Formula (1), (2) or (3) of the present invention are shown below. However, the present invention is not limited thereto.

[Chem. 18]

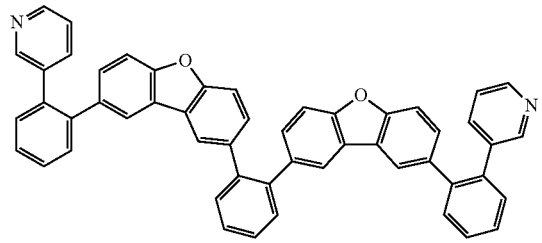

1

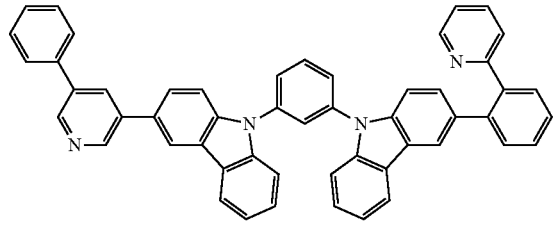

2

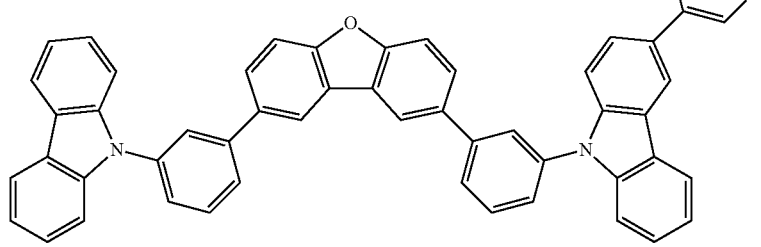

3

-continued
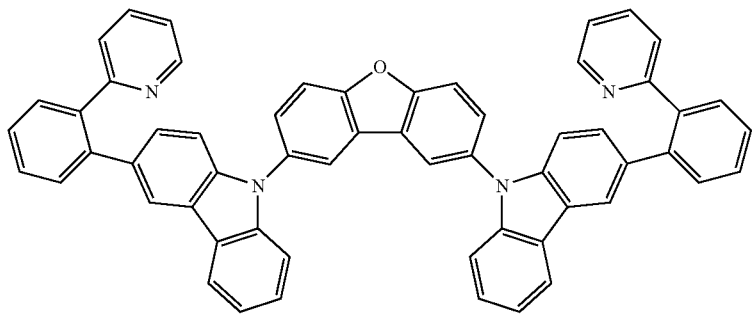
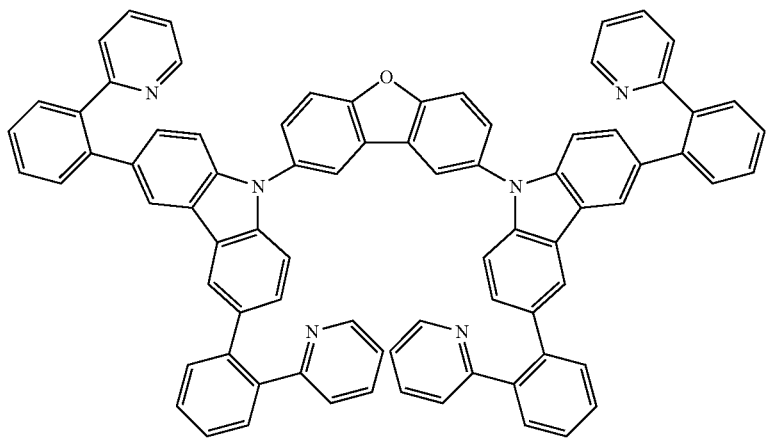
[Chem. 19]
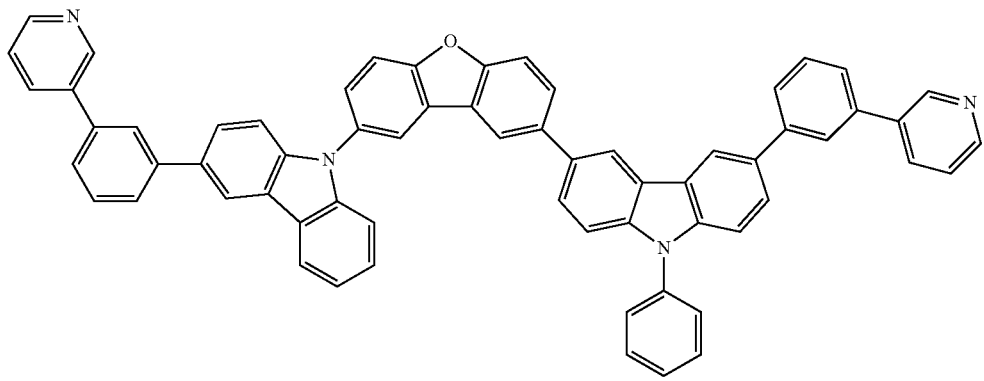
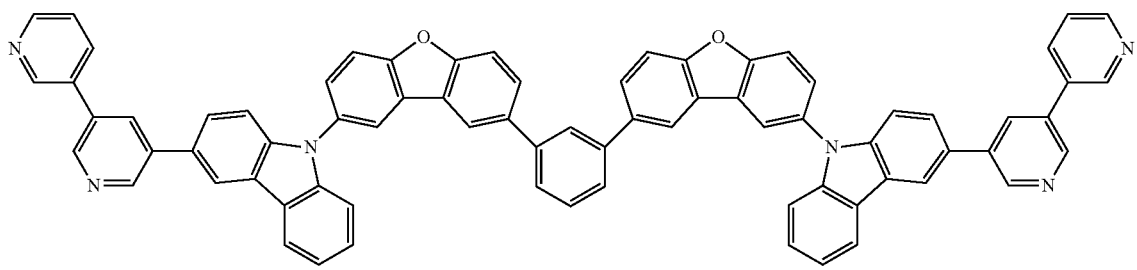

-continued
8
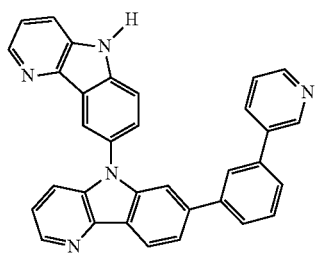
9
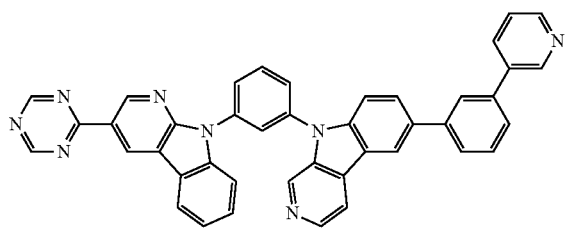
[Chem. 20]
10
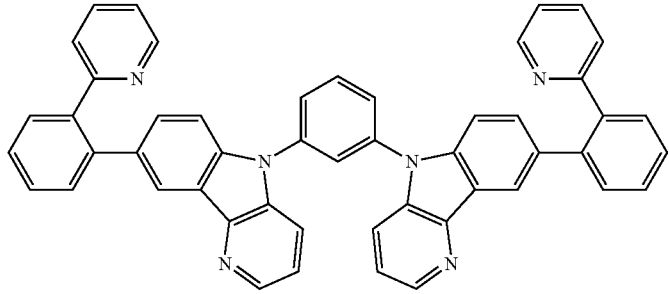
11
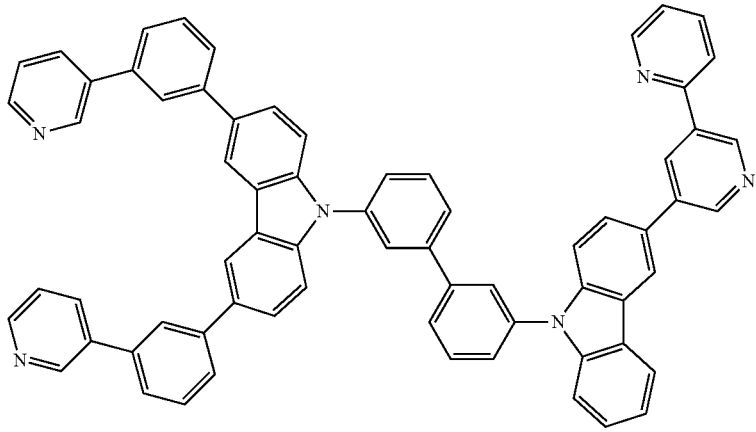
12
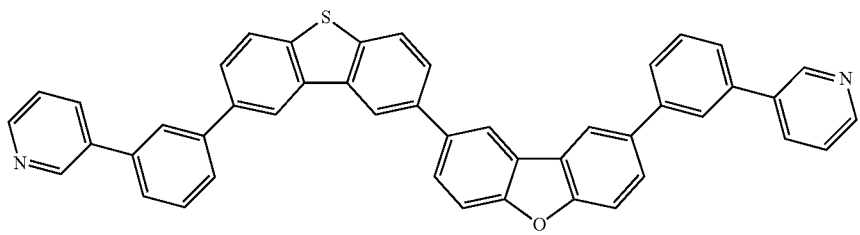
13
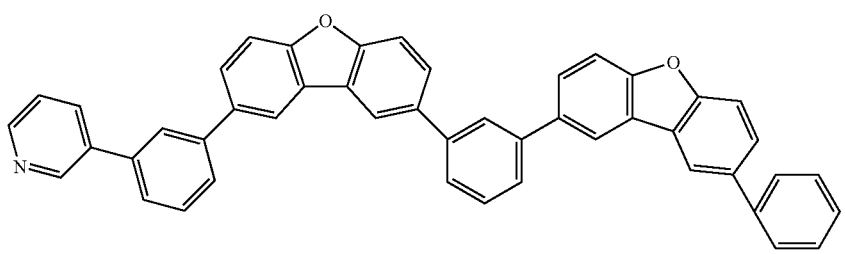

14
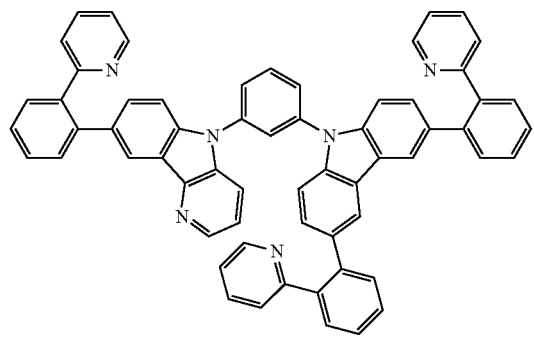
15
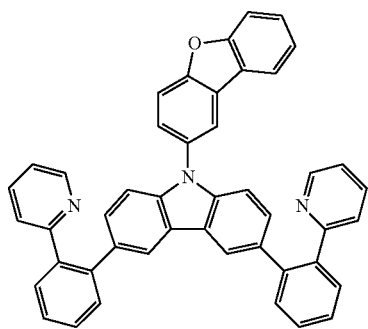
[Chem. 21]
16
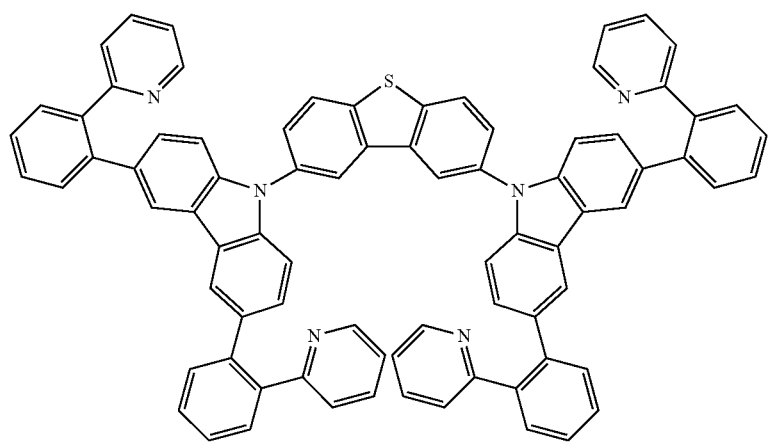
17
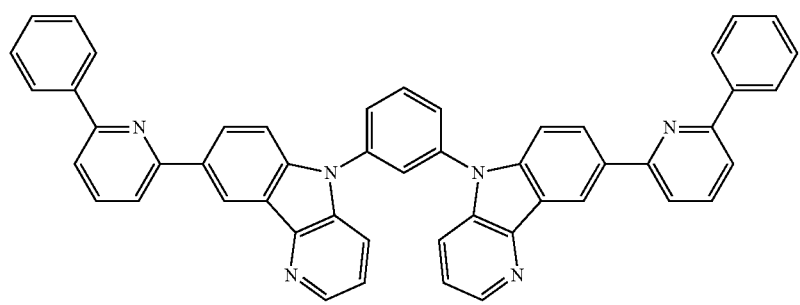

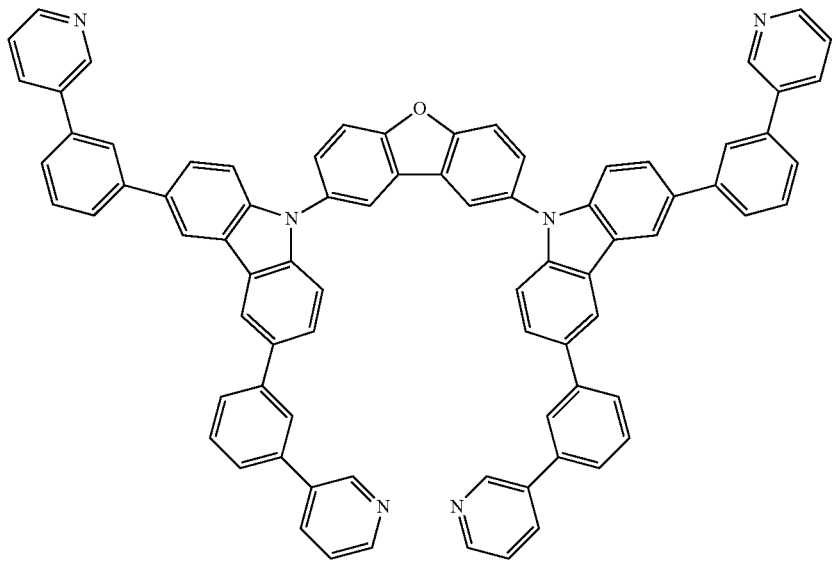
18
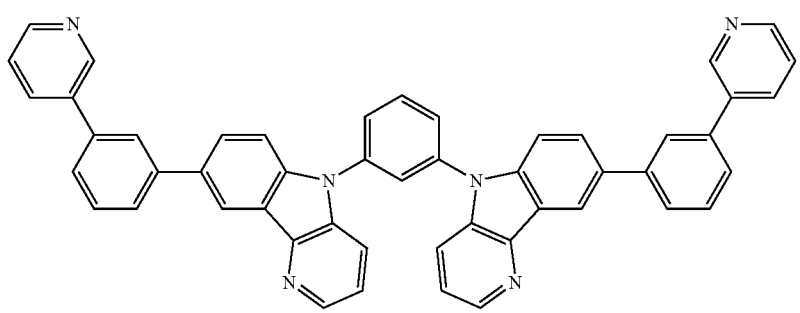
19
[Chem. 22]
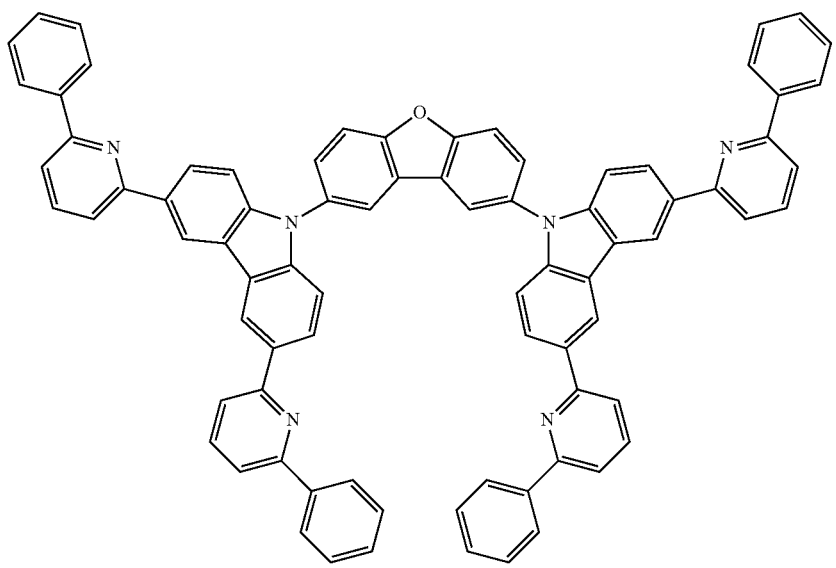
20

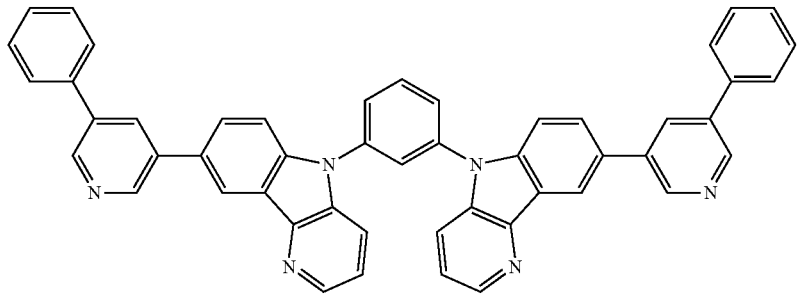
21
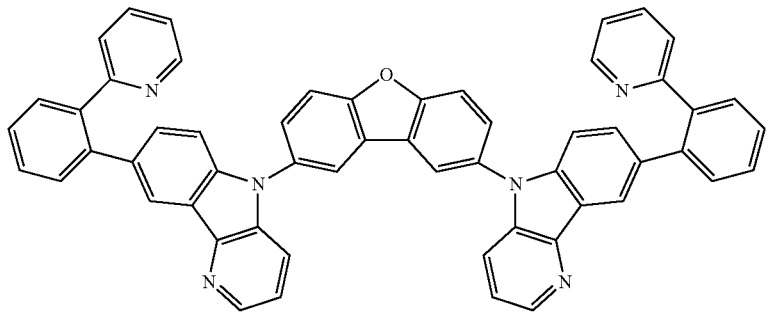
22
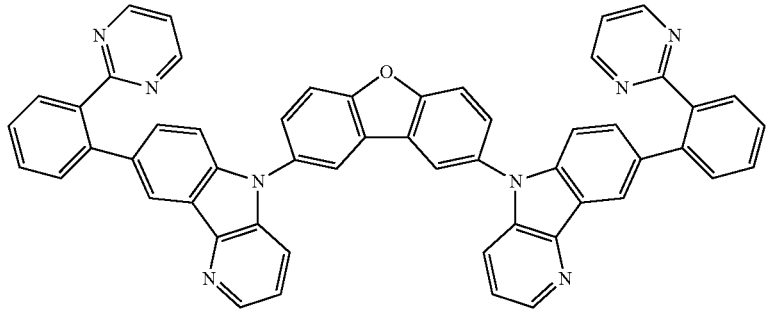
23
[Chem. 23]
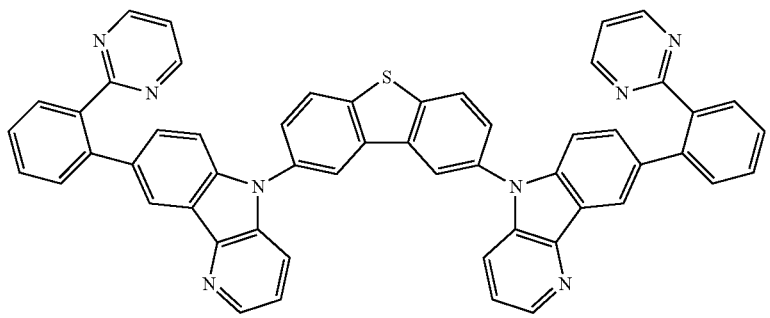
24
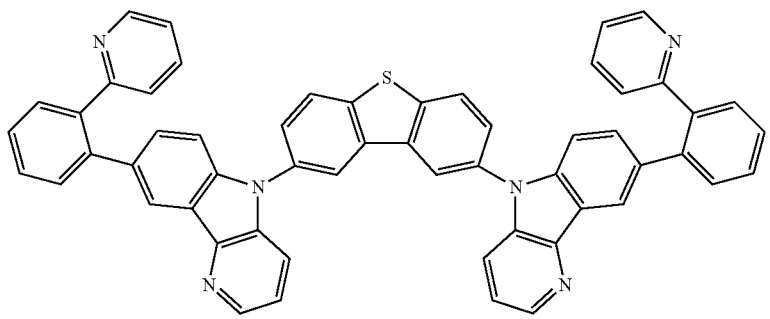
25

26
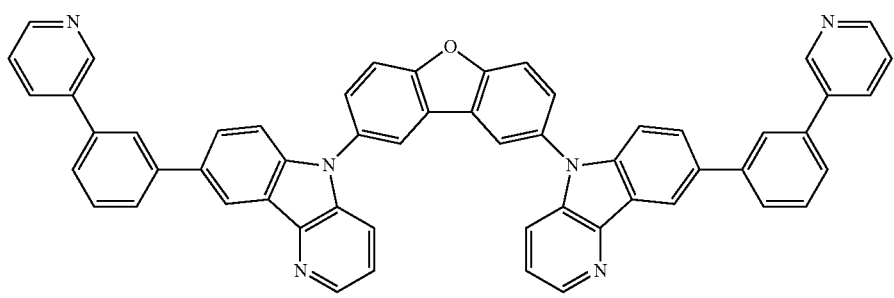
27
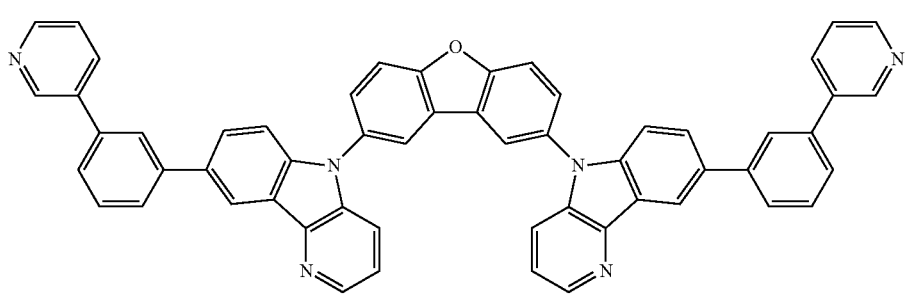
28
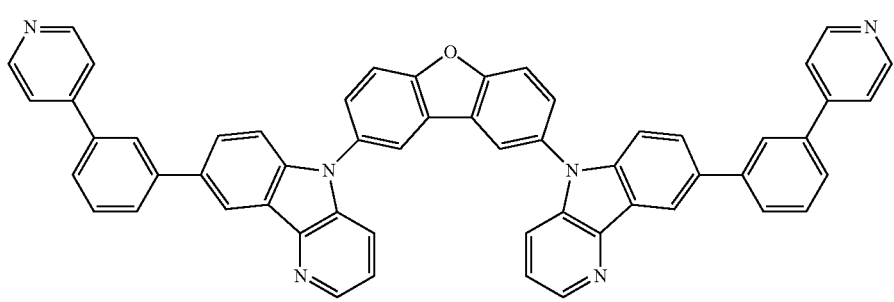
29
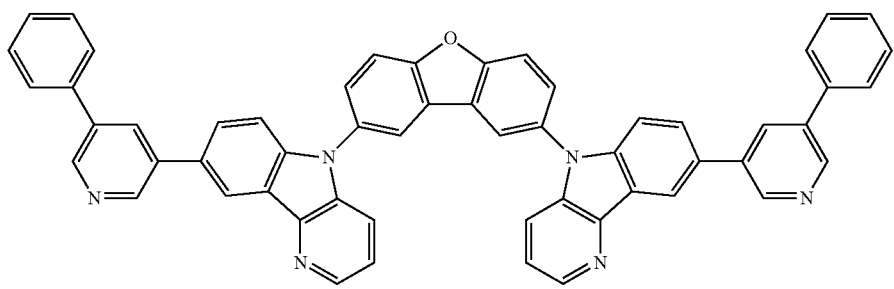
[Chem. 24]
30
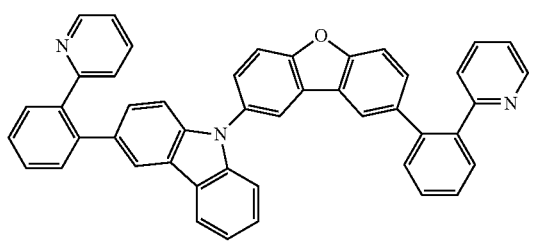
31
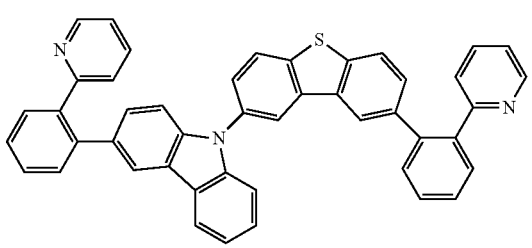

-continued
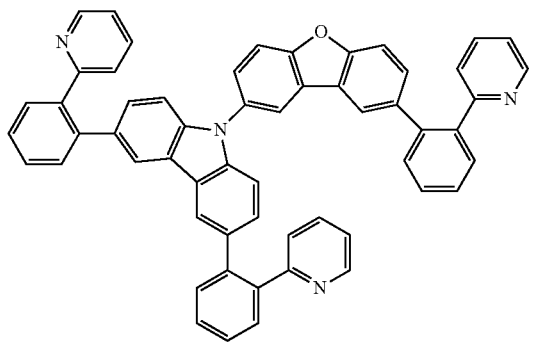
32
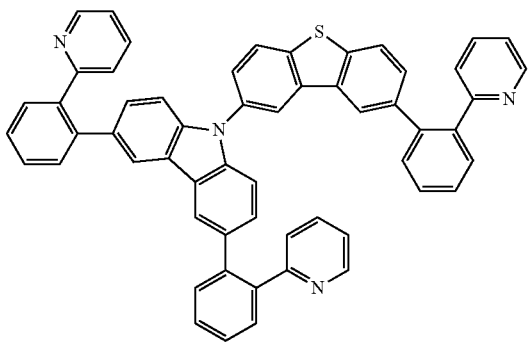
33
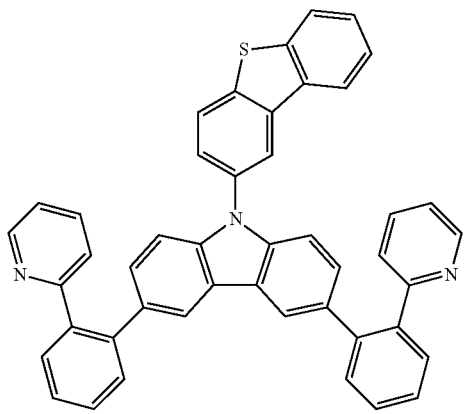
34
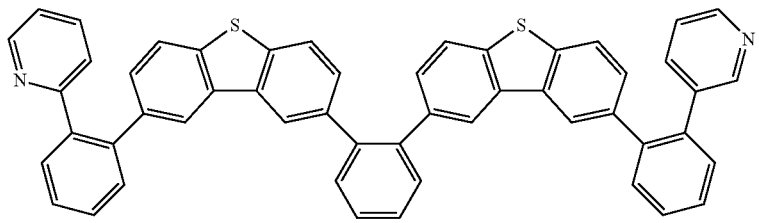
35
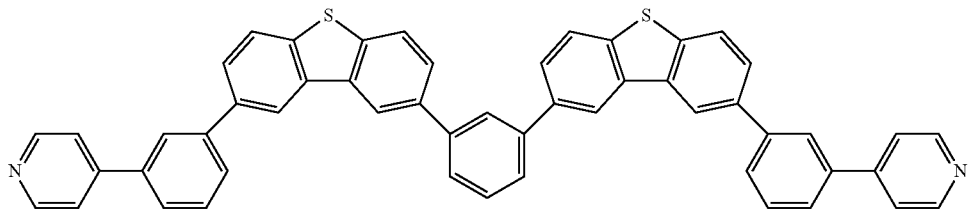
36
[Chem. 25]
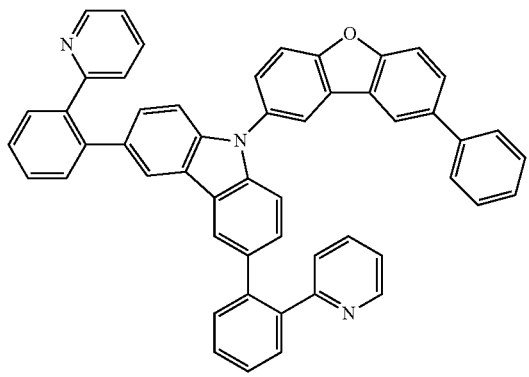
37
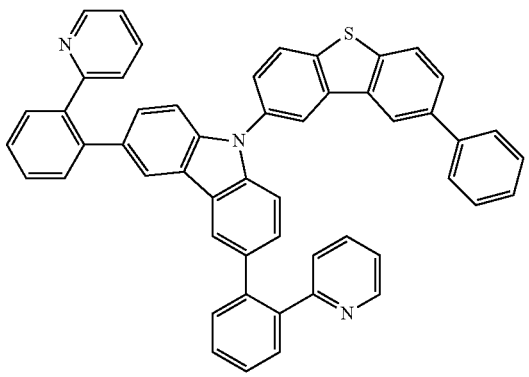
38

-continued
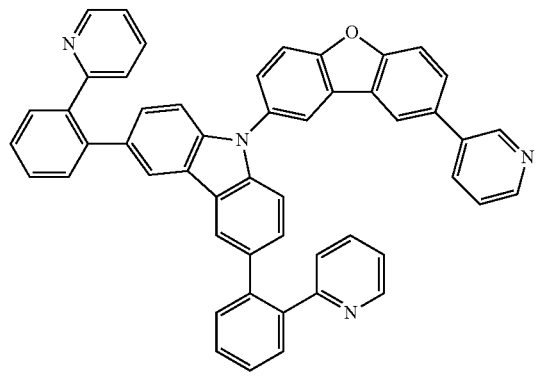
39
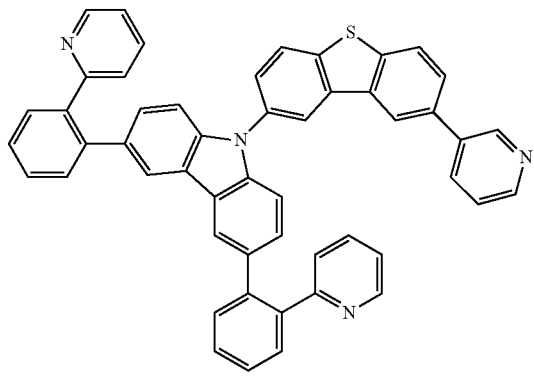
40
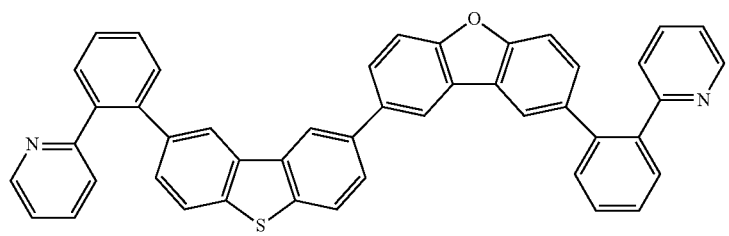
41
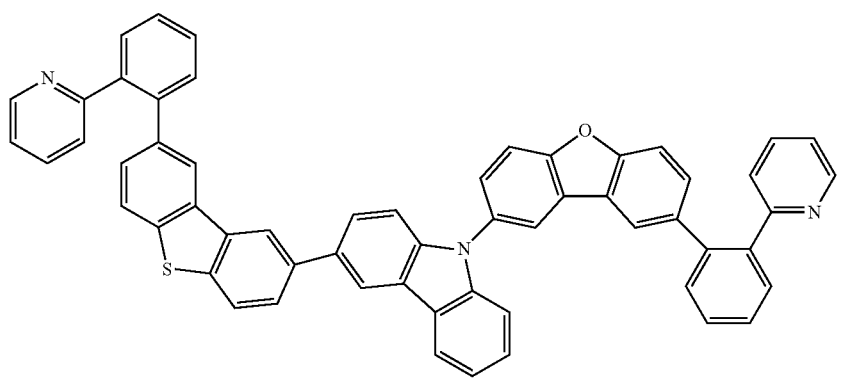
42
[Chem. 26]
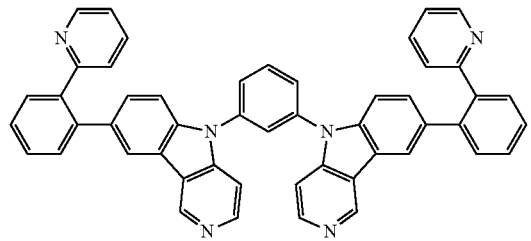
43
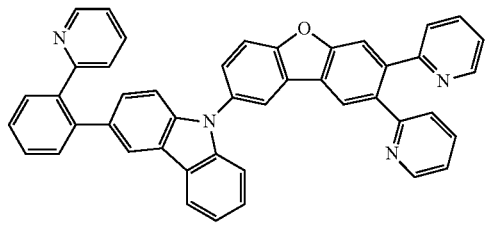
44
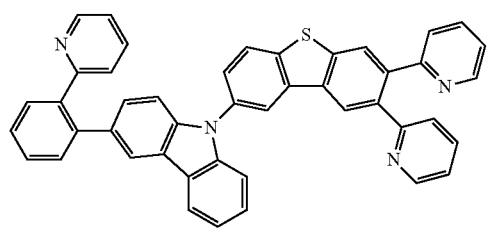
45
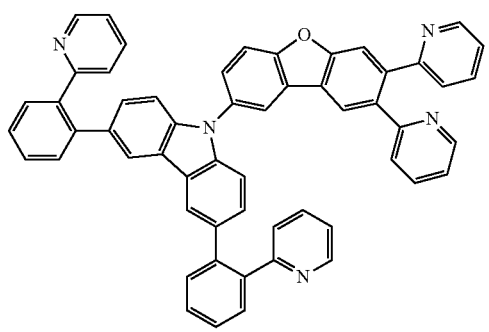
46

47
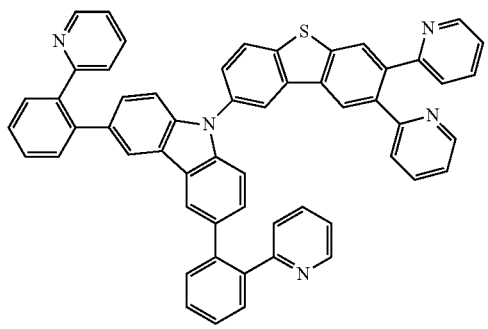
[Chem. 27]
48
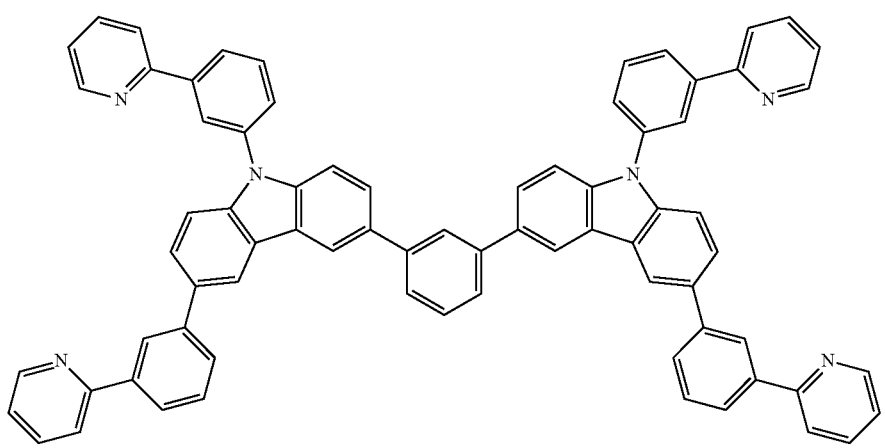
49
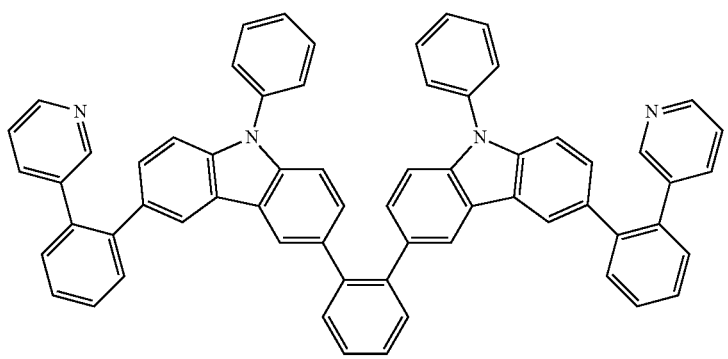
50
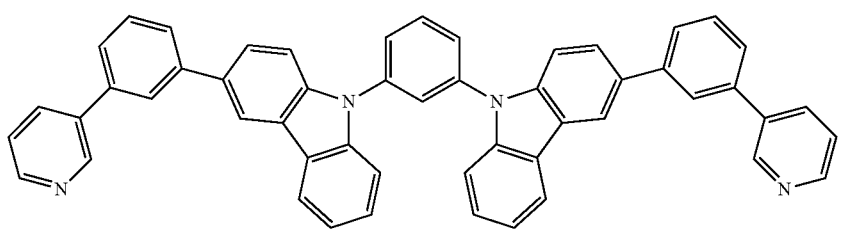

-continued
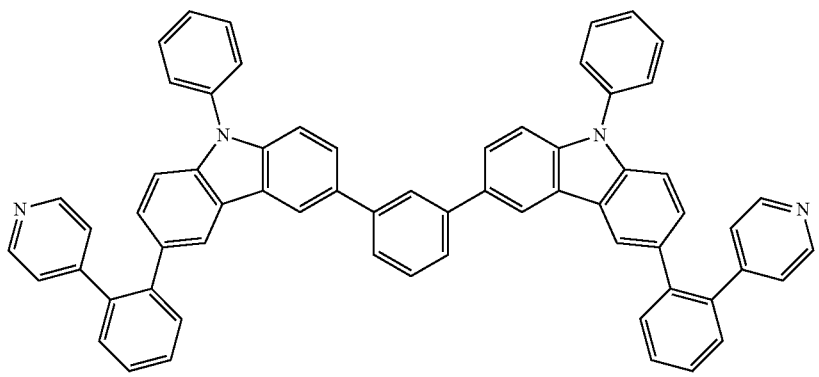
51
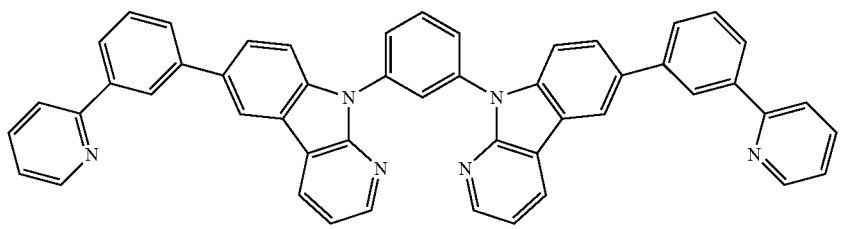
52
[Chem. 28]
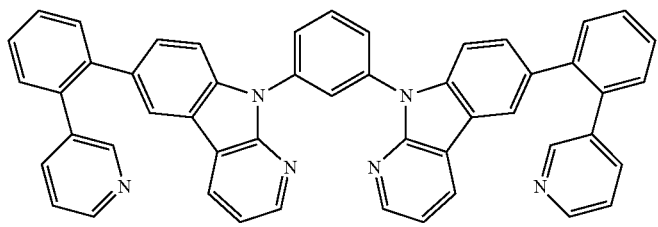
53
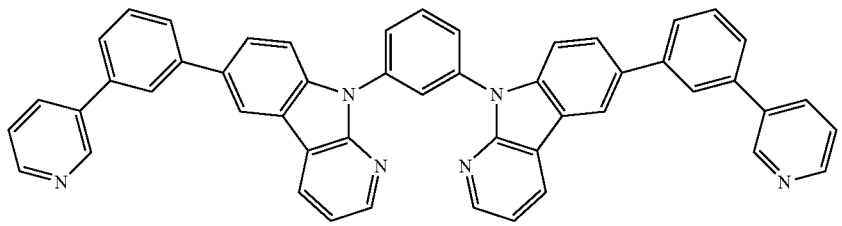
54
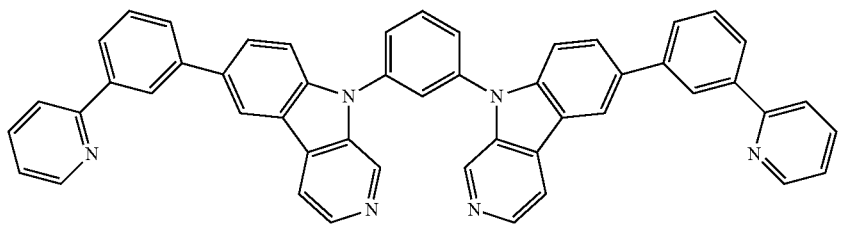
55
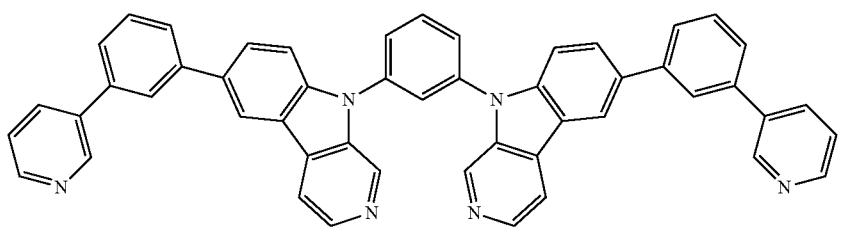
56

-continued
57
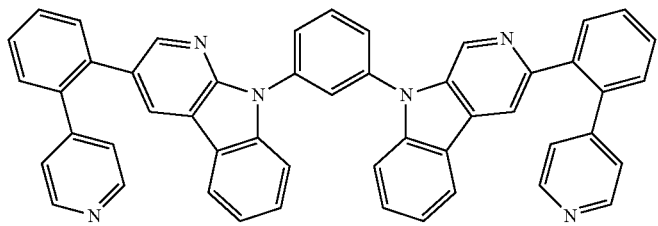
58
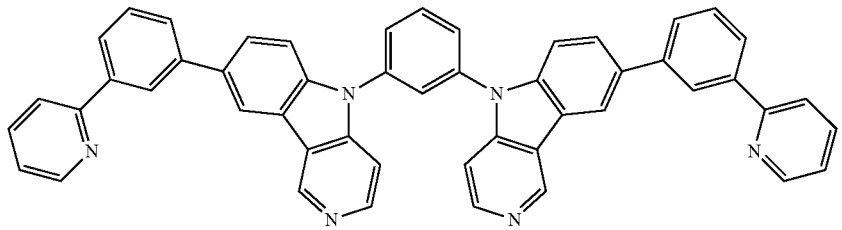
[Chem. 29]
59
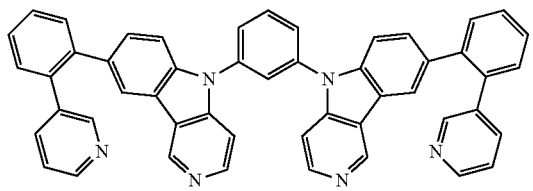
60
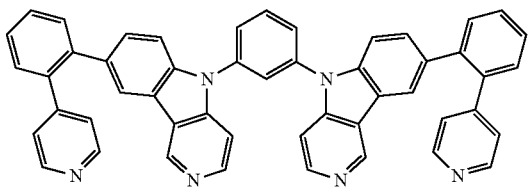
61
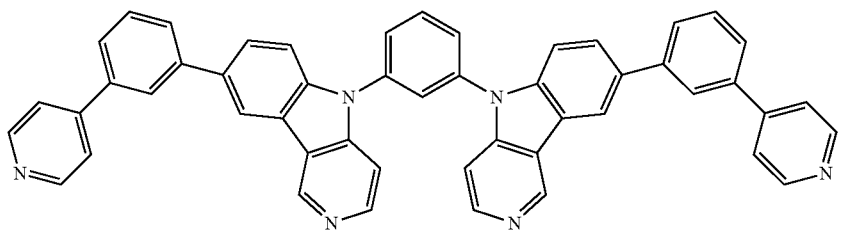
62
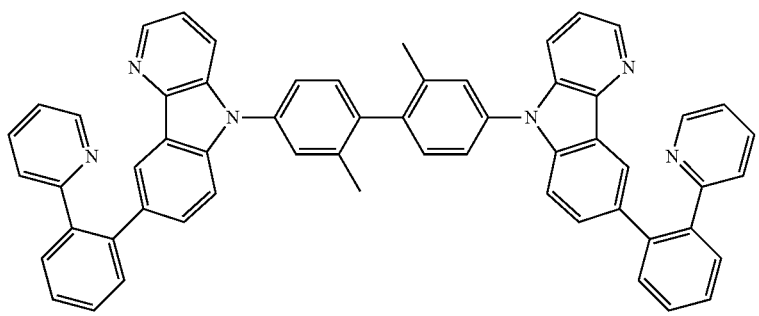
63
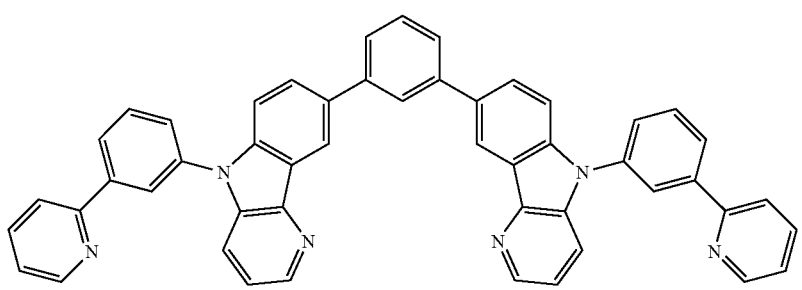

-continued
64
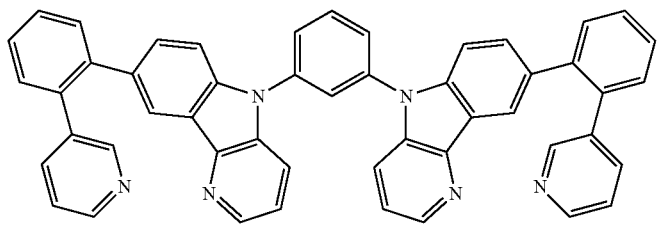
[Chem. 30]
65
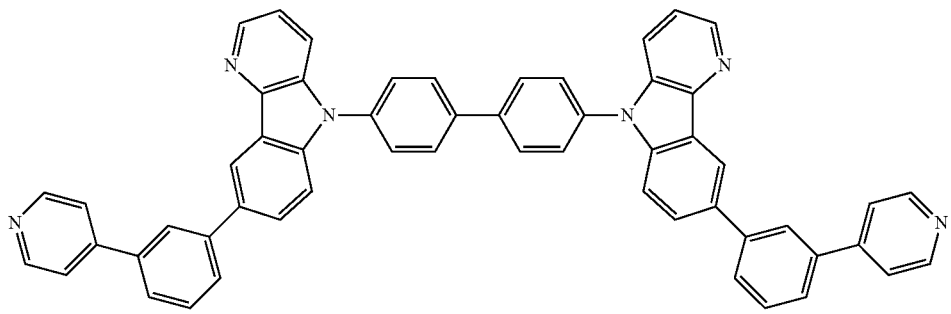
66
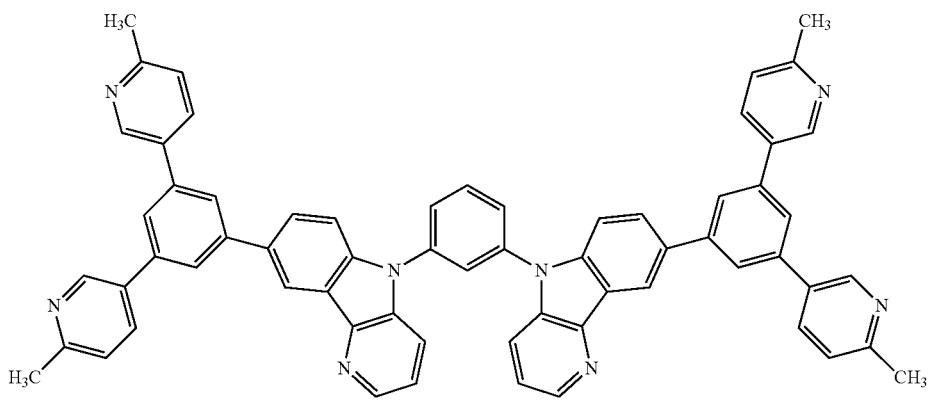
67
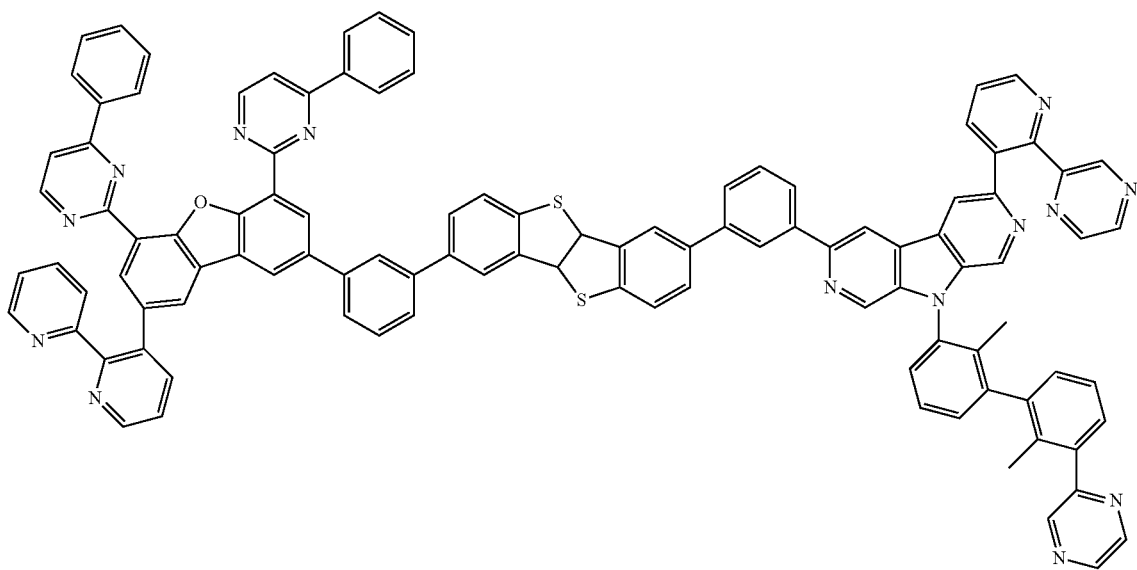

[Chem. 31]
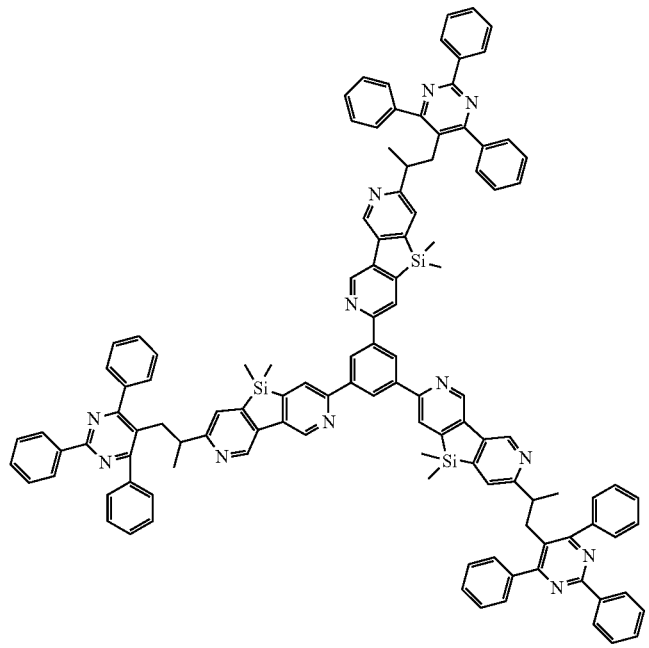
68
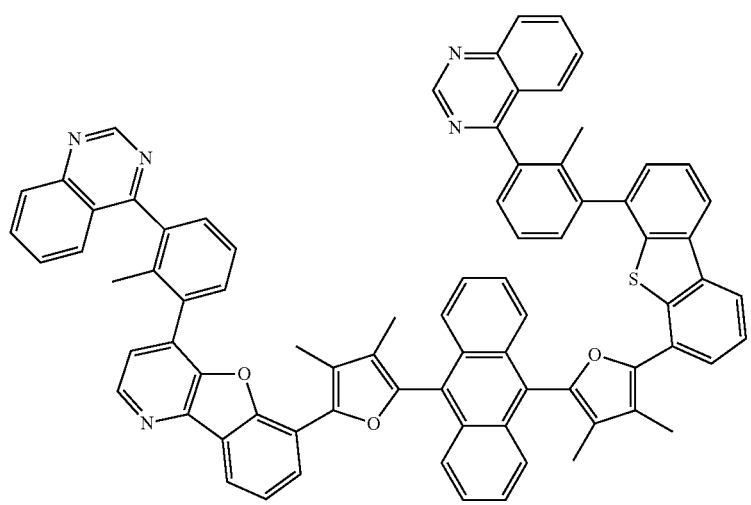
69
[Chem. 32]
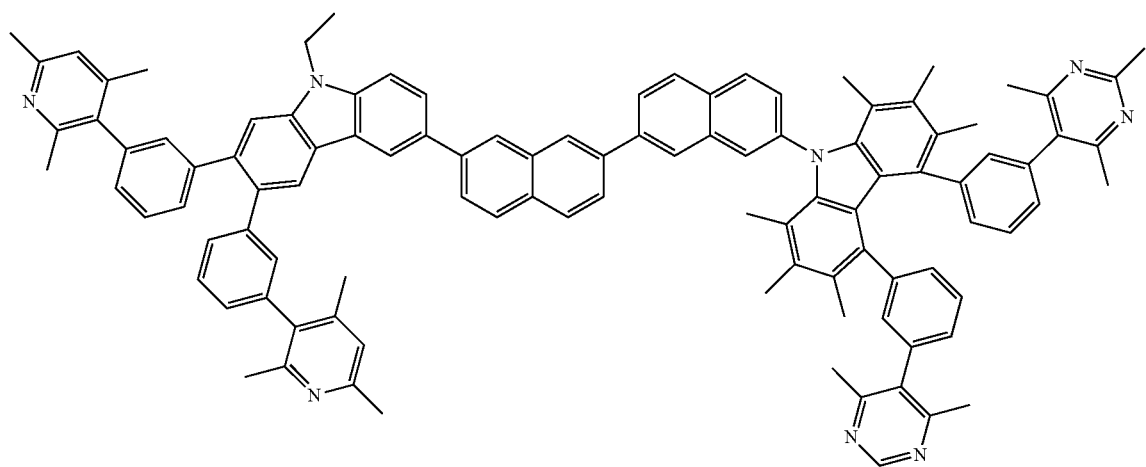
70

-continued
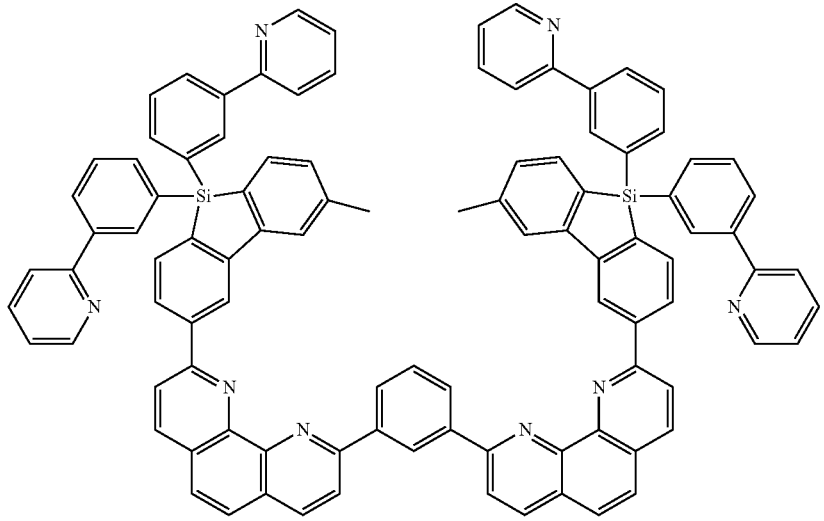
71
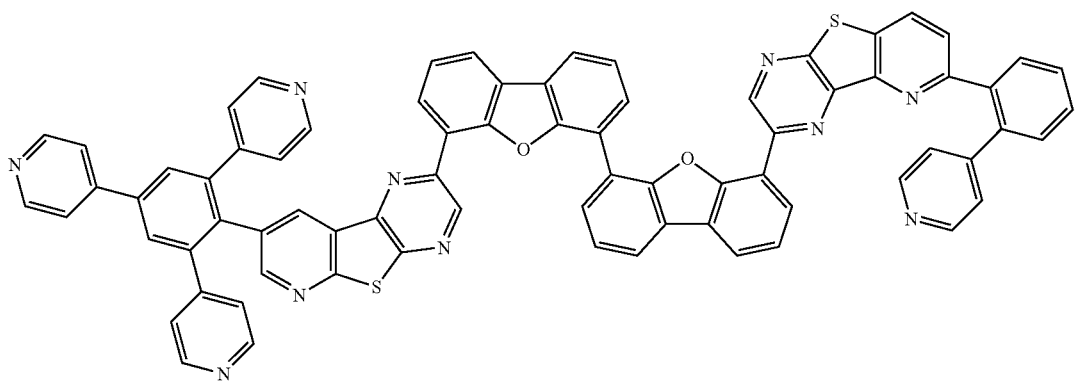
72
[Chem. 33]
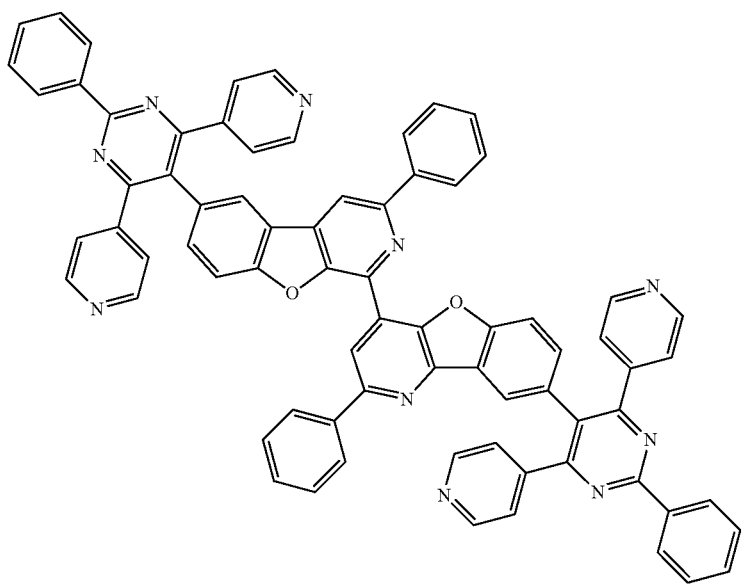
73

74
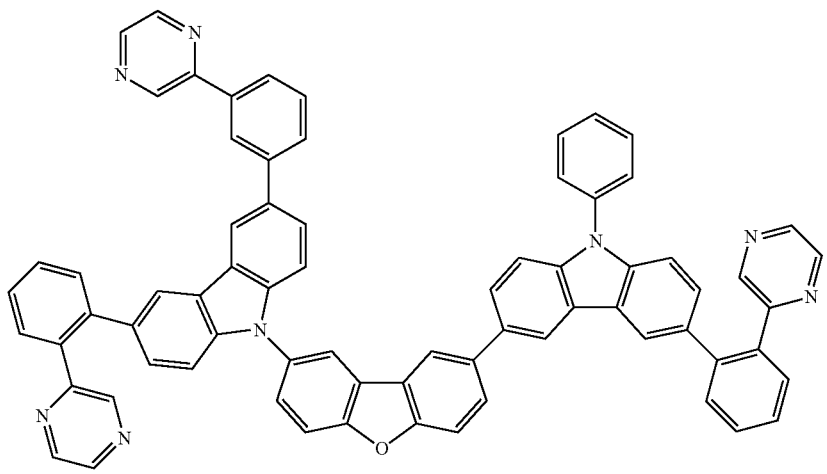
75
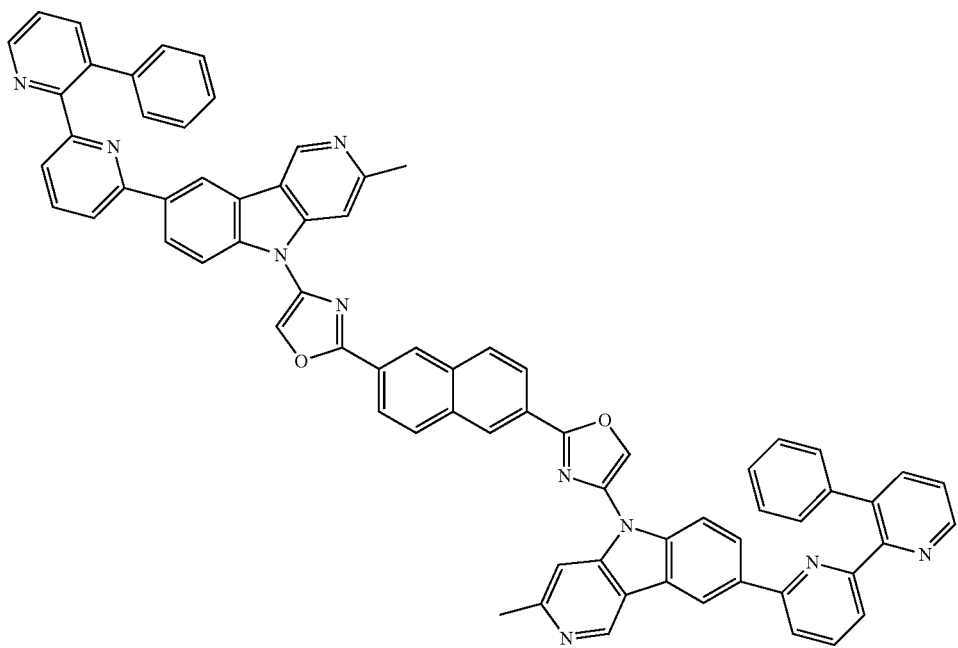

[Chem. 34]
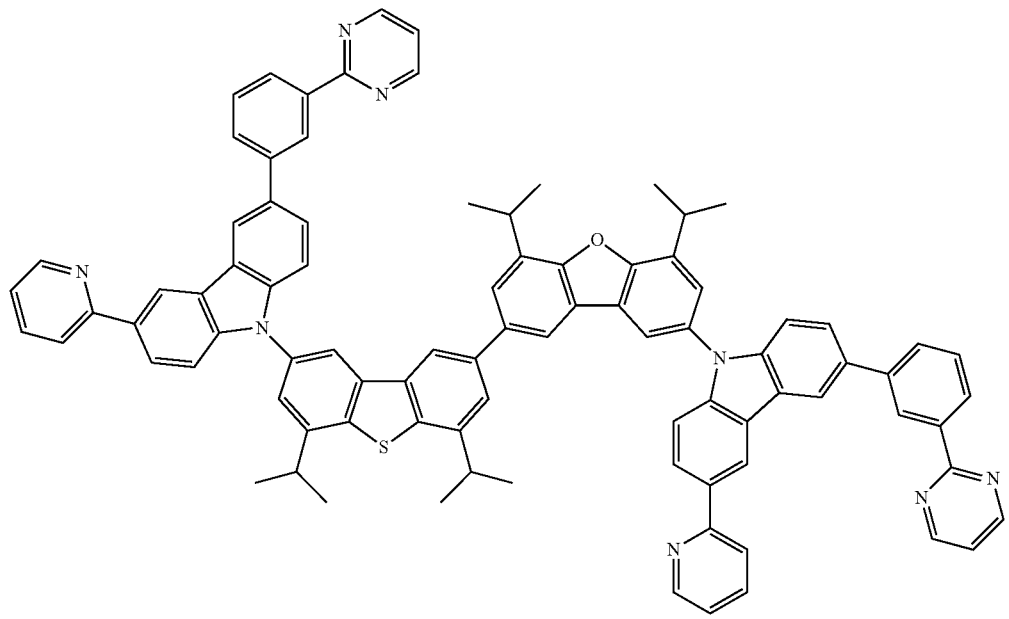
76
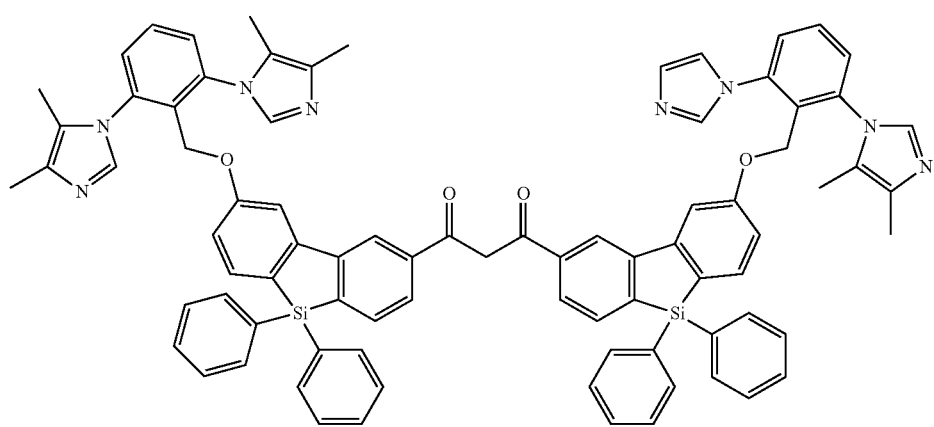
77

-continued
78
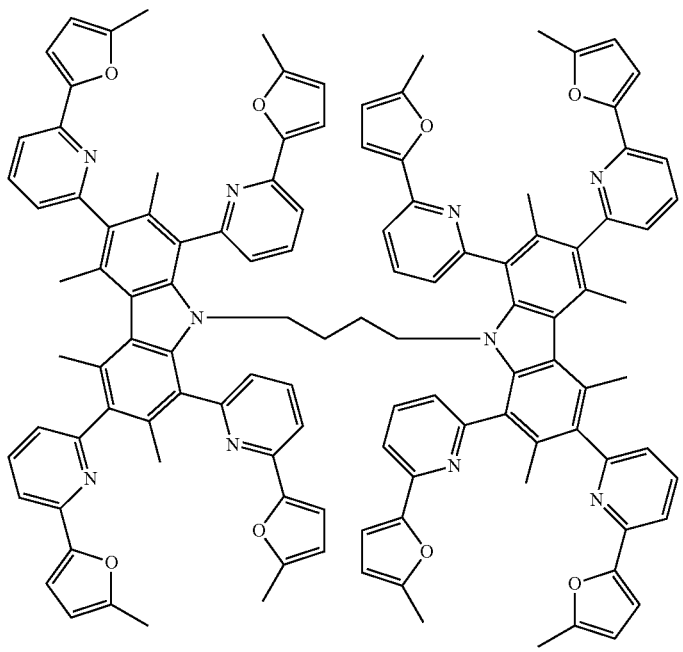
[Chem. 35]
79
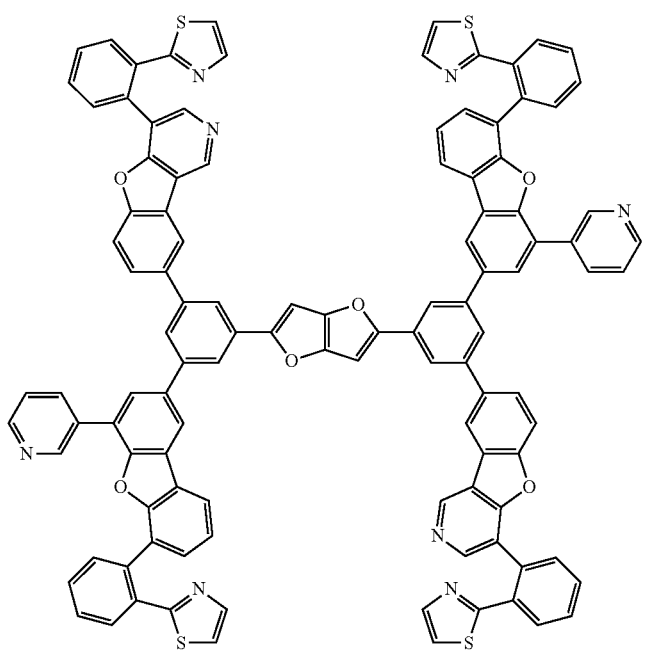

80
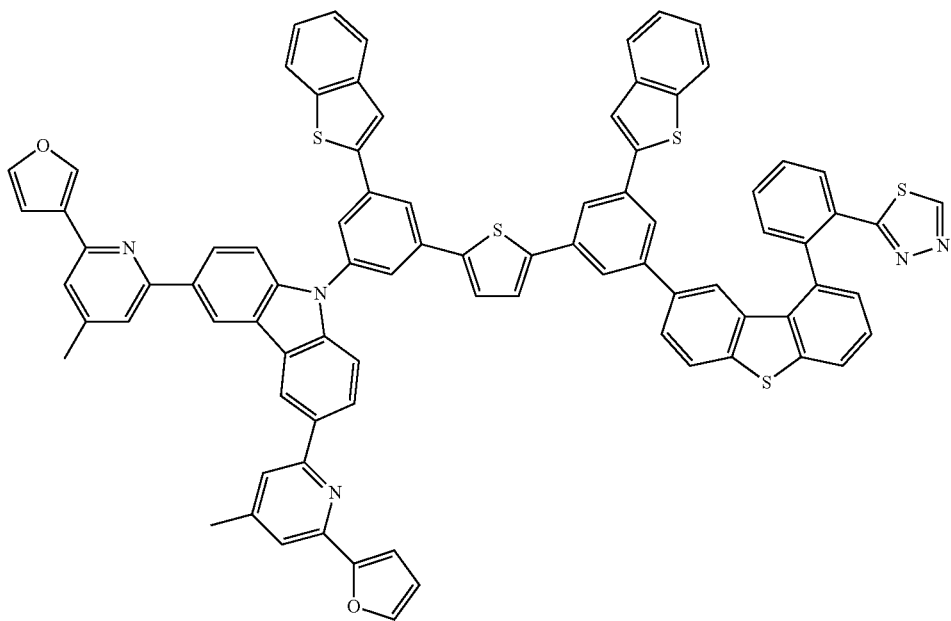
[Chem. 36]
81
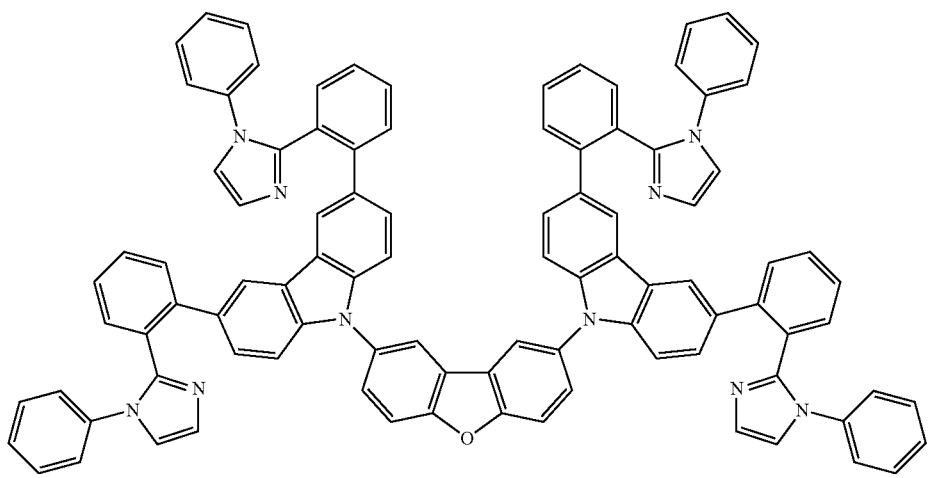
82
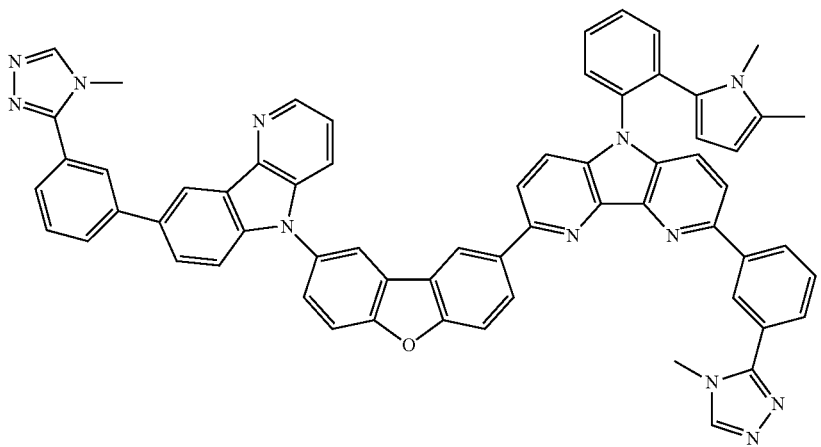

83
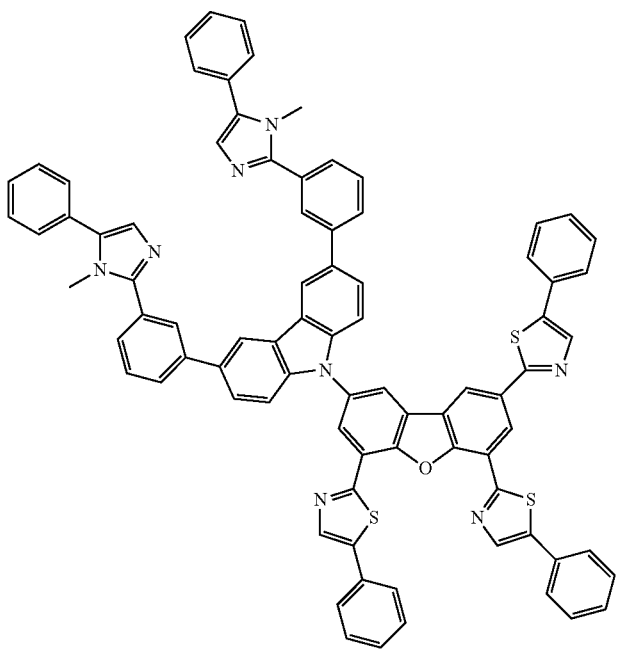
[Chem. 37]
84
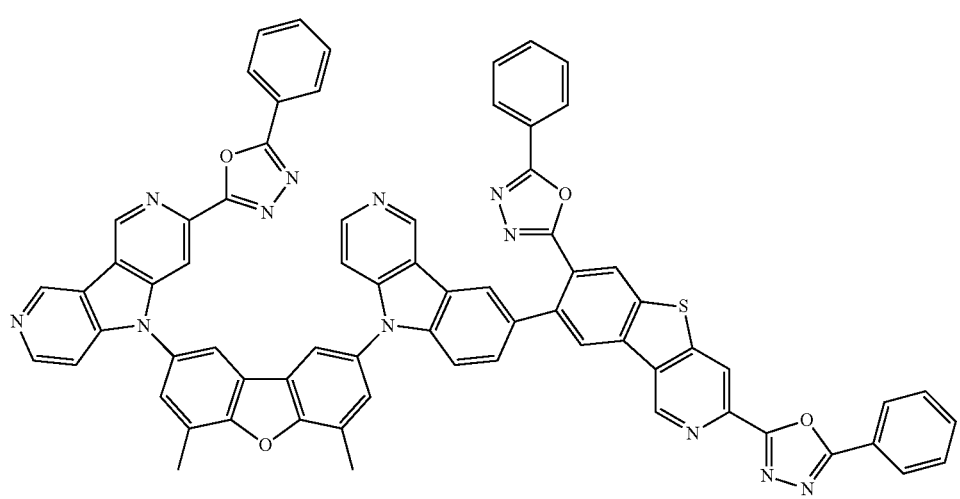

85
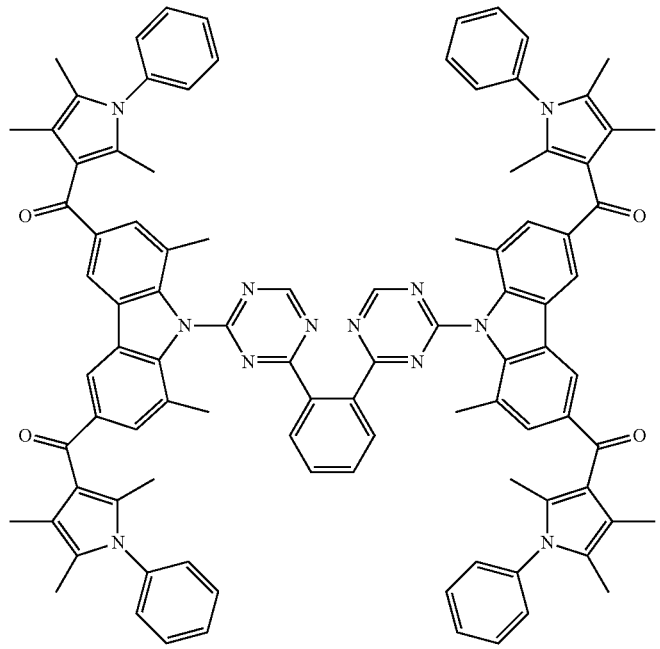
[Chem. 38]
86
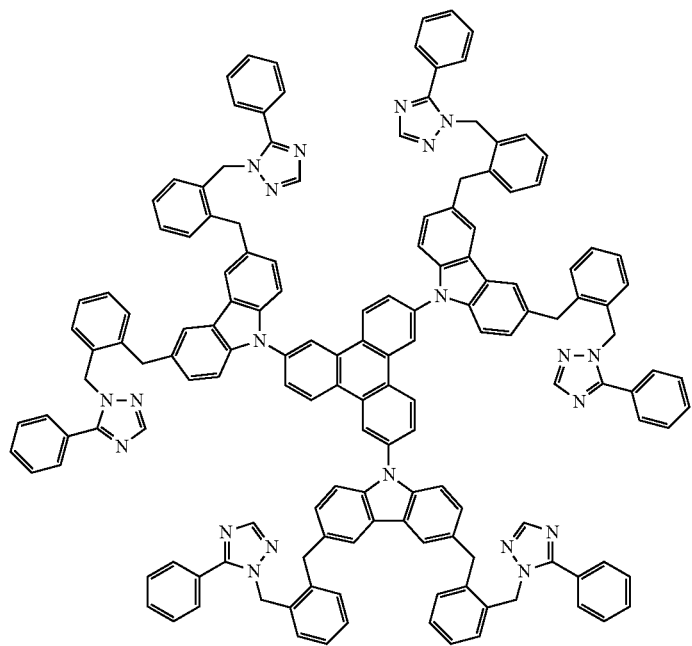

-continued
87
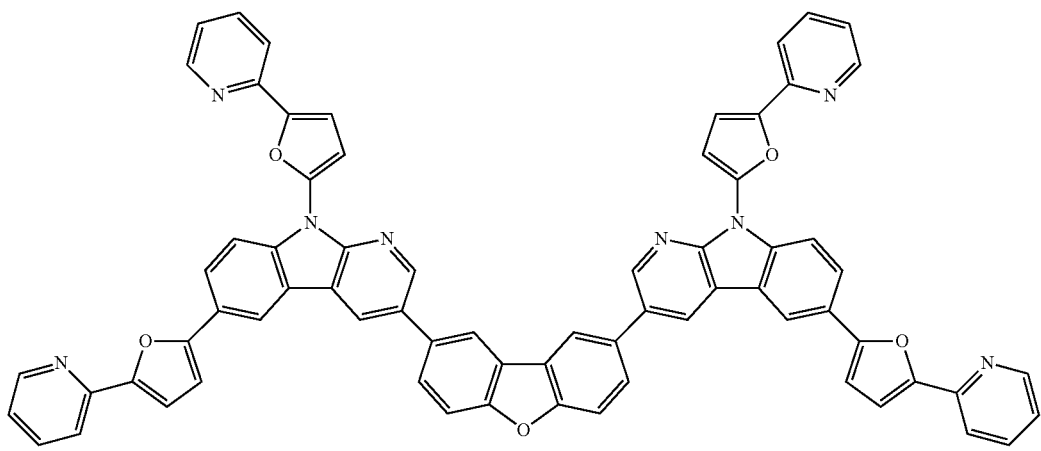
88
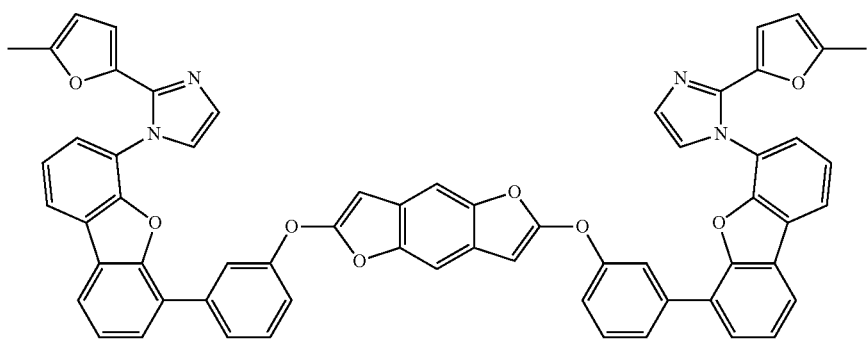
[Chem. 39]
89
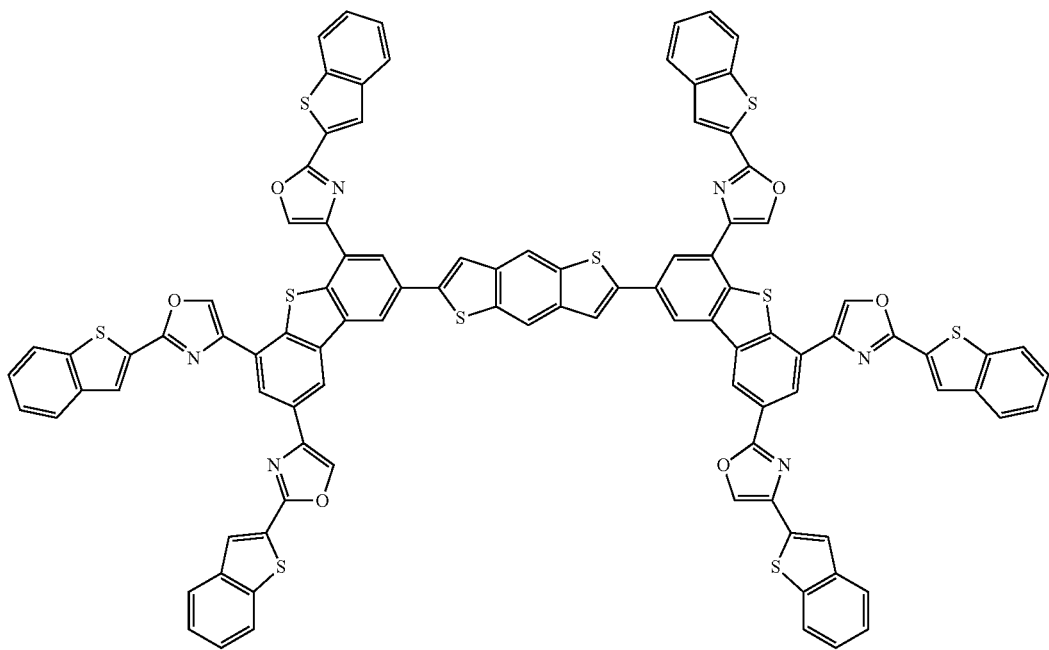

81
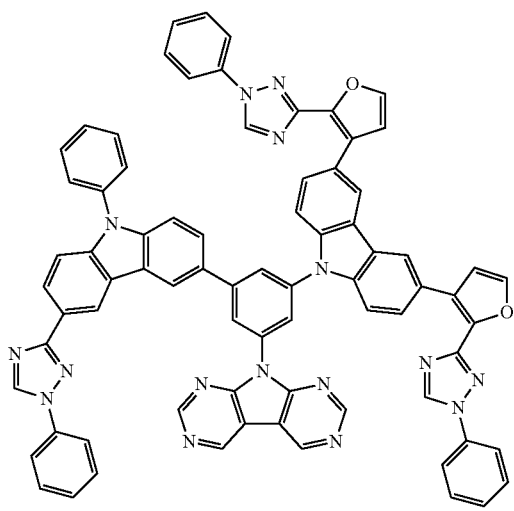
90
82
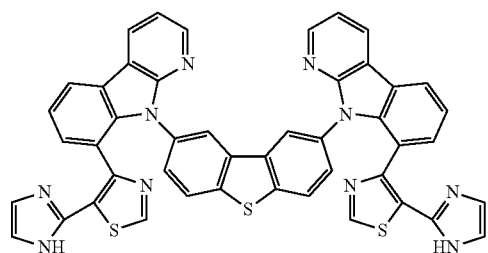
91
[Chem. 40]
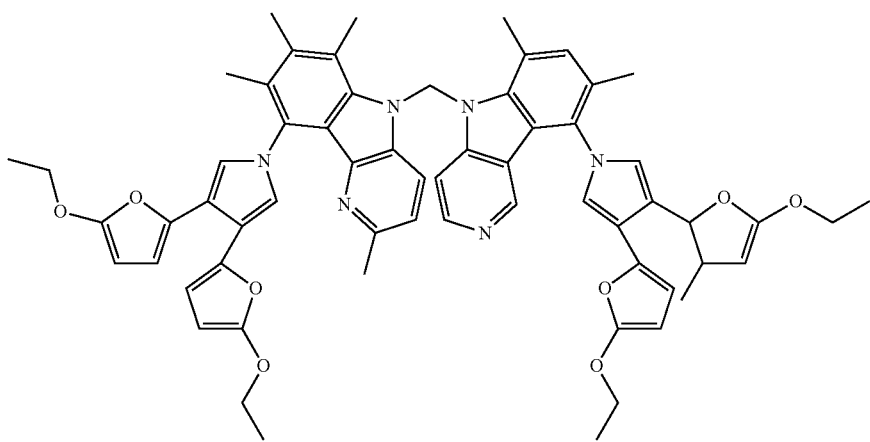
92
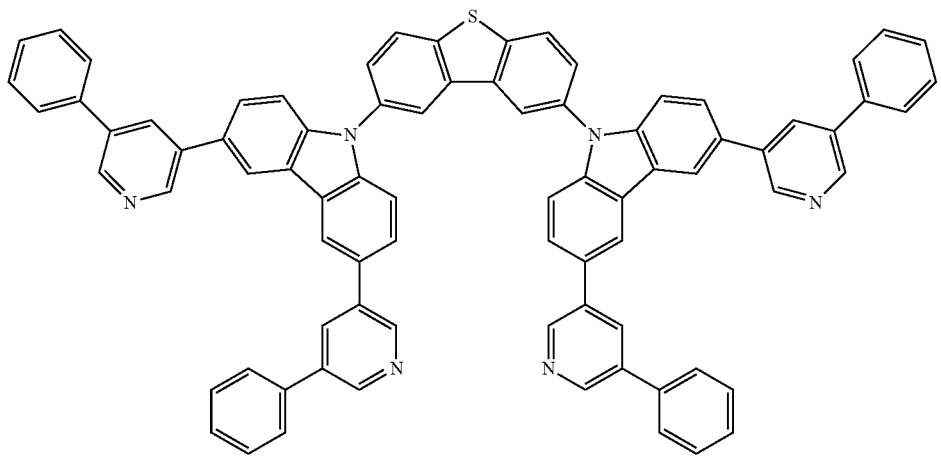
93

94
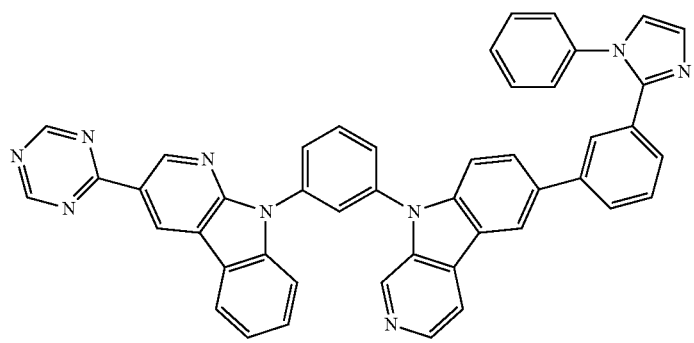
95
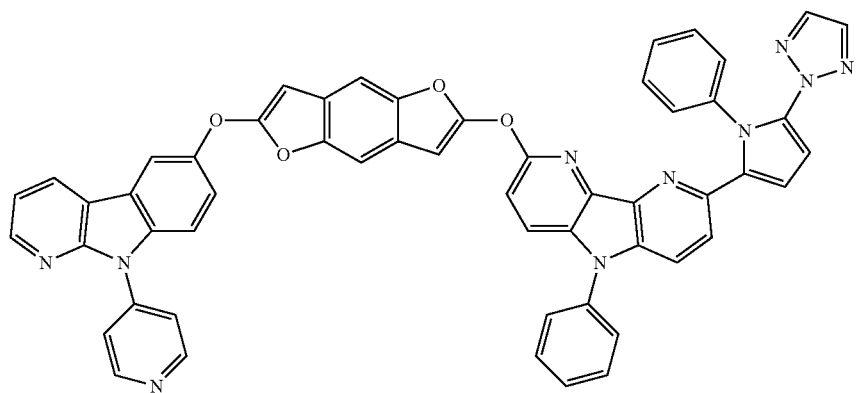
[Chem. 41]
96
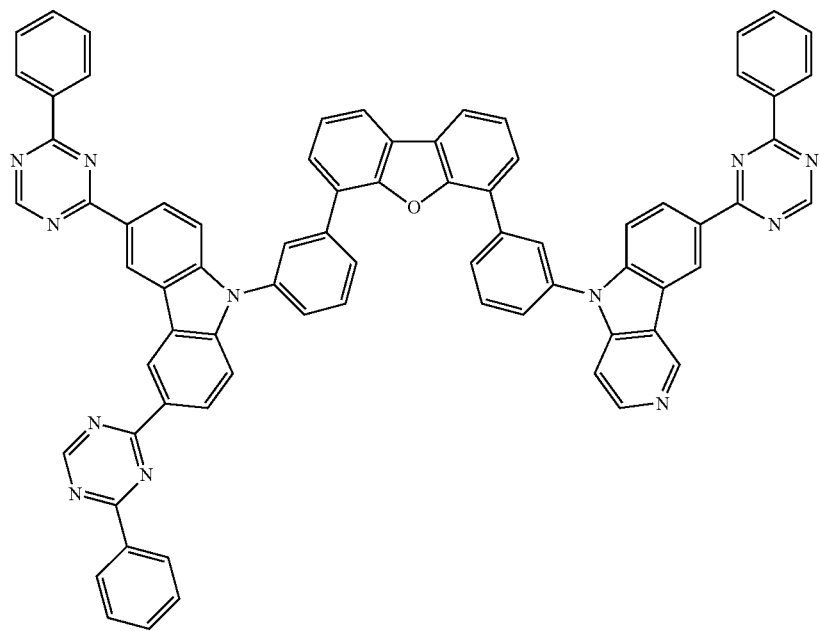

-continued
97
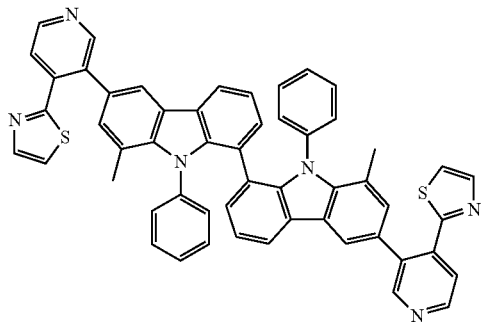
98
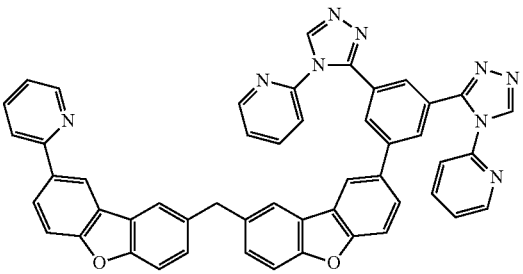
99
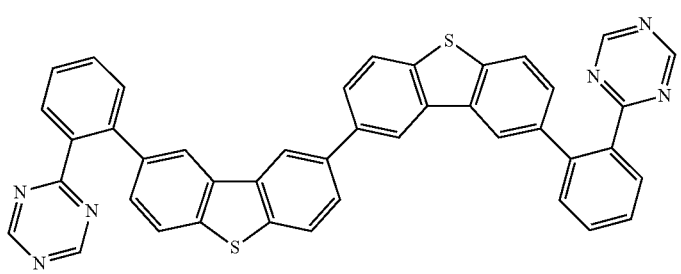
[Chem. 42]
100
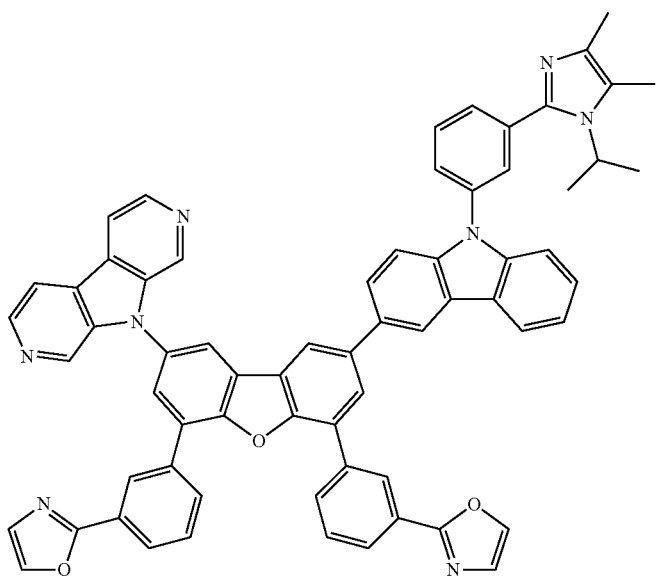

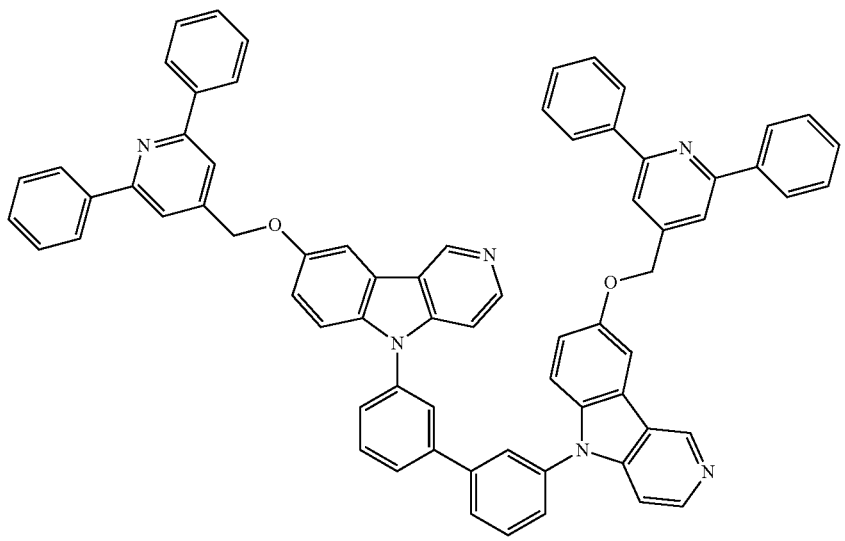
101
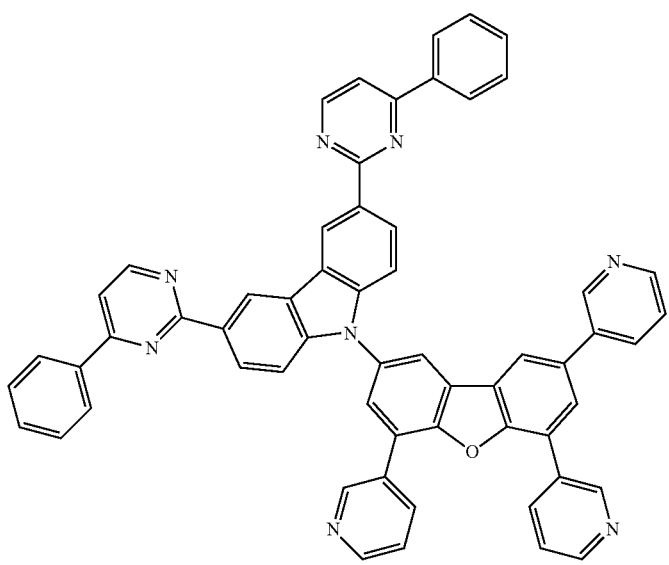
102
[Chem. 43]
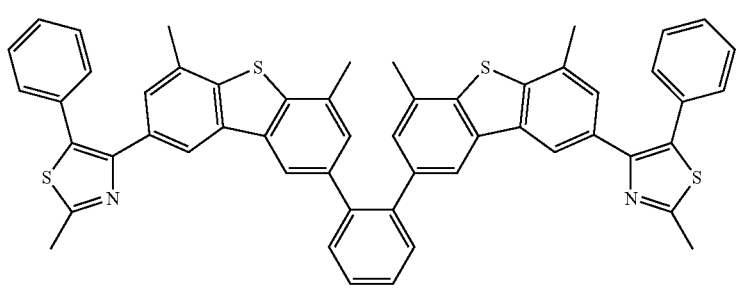
103

104
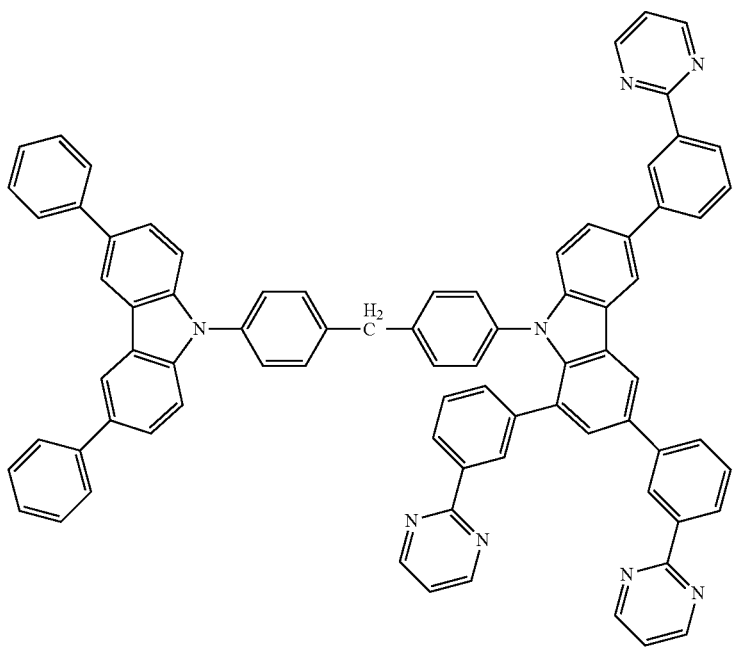
105
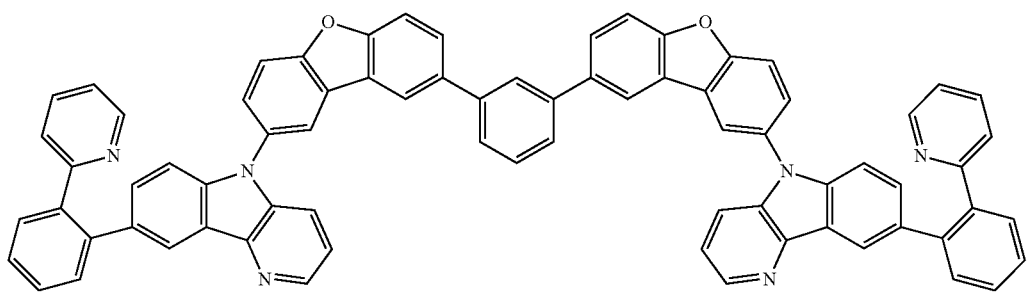
106
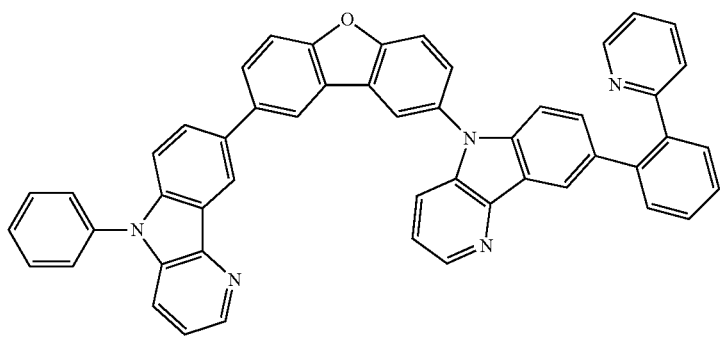

107
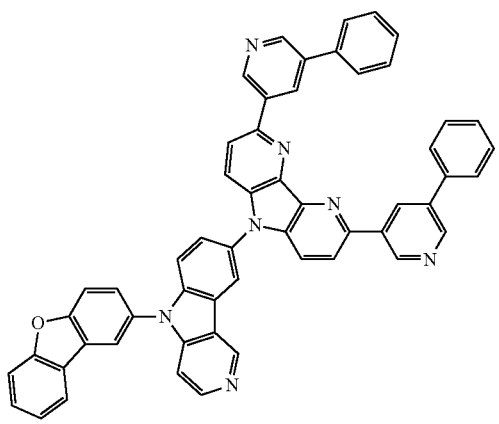
108
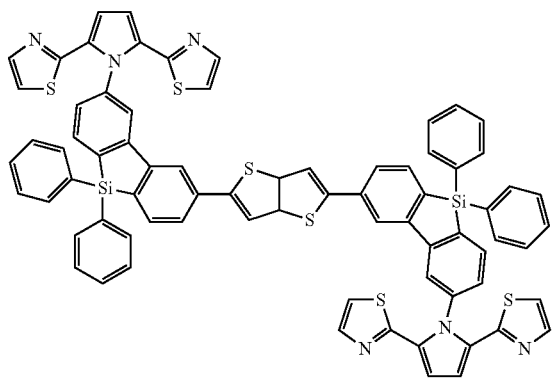
109
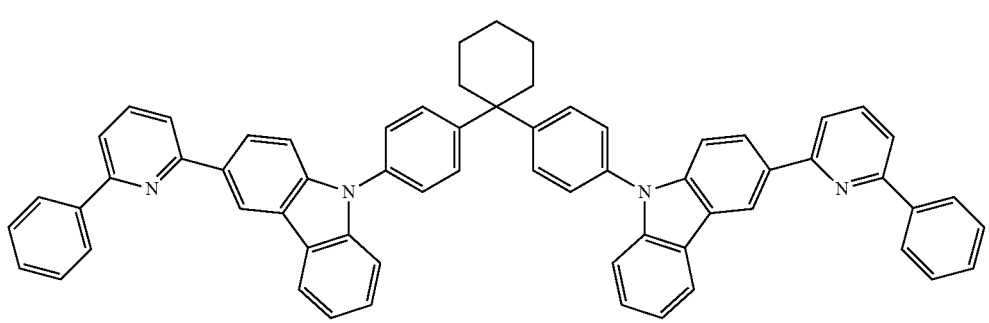
110 111
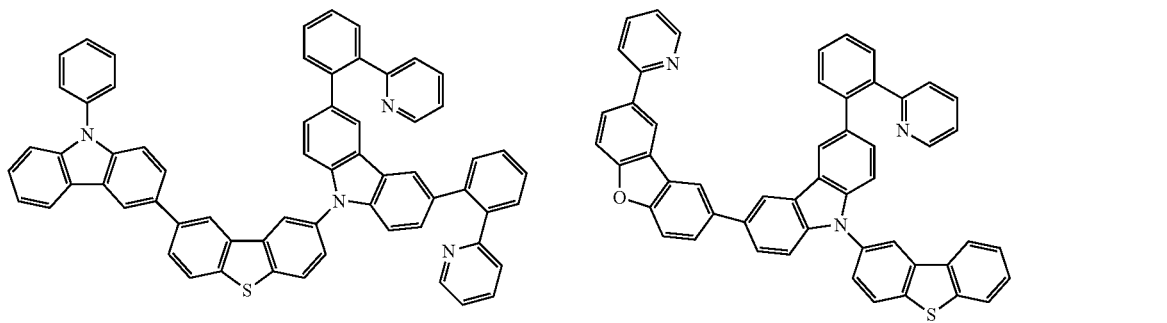
A typical example of synthesis of a compound is shown below.
<<Example of Synthesis of Compound 5>>
[Chem. 46]
Synthesis of Compound 5
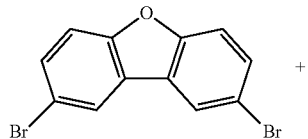
-continued
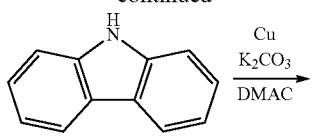
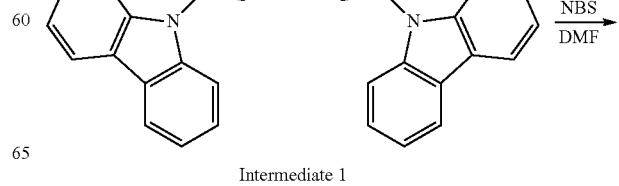
Intermediate 1

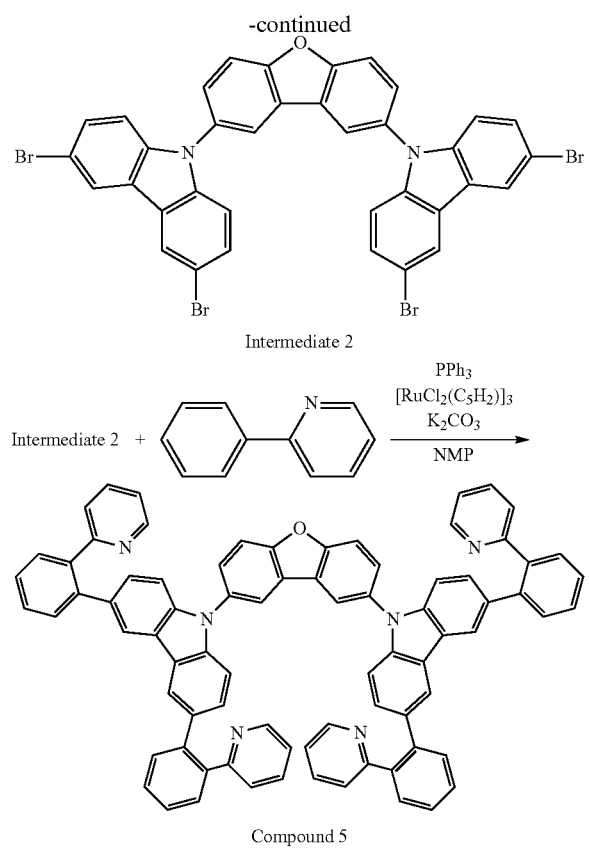

Intermediate 2

Compound 5

Process 1: (Synthesis of Intermediate 1)

Under nitrogen atmosphere, 1.0 mol of 3,6-dibromodibenzofuran, 2.0 mol of carbazole, 3.0 mol of copper powder and 1.5 mol of potassium carbonate were mixed in 300 ml of DMAc (dimethylacetamide) and then stirred for 24 hrs at 130° C. After the reaction liquid was cooled to room temperature, 1 L of toluene was added to the liquid, the obtained liquid was washed three times with distilled water, the organic layer distilled the solvent under reduced pressure, and the residue was purified with silica gel flash chromatography (n-heptane:toluene=4:1 to 3:1). Thus, Intermediate 1 was obtained at a yield of 85%.

Process 2: (Synthesis of Intermediate 2)

At room temperature under atmospheric pressure, 0.5 mol of Intermediate 1 was dissolved into 100 ml of DMF, 2.0 mol of NBS was added to the liquid and then stirred for one night at room temperature. The obtained precipitates were filtered and washed with methanol. Thus, Intermediate 2 was obtained at a yield of 92%.

Process 3: (Synthesis of Compound 5)

Under nitrogen atmosphere, 0.25 mol of Intermediate 2, 1.0 mol of 2-phenylpyridine, 0.05 mol of ruthenium complex [(η6-$C_6H_6$)$RuCl_2$]$_2$, 0.2 mol of triphenylphosphine and 12 mol of potassium carbonate were mixed in 3 L of NMP (N-methyl-2-pyrrolidone) and then stirred for one night at 140° C.

After the reaction liquid was cooled to room temperature, 5 L of dichloromethane was added to the liquid, and then the liquid was filtered. The filtrate distilled the solvent under reduced pressure (800 Pa, 80° C.), and the (N-methyl-2-pyrrolidone) residue was purified with silica gel flash chromatography ($CH_2Cl_2$:$Et_3N$=20:1 to 10:1).

After the fractions were collected and the solvent was distilled under reduced pressure, the residue was again dissolved into dichloromethane and washed three times with water. After the organic layer was dried with anhydrous magnesium sulfate, the solvent was distilled under reduced pressure. Thus, Compound 5 was obtained at a yield of 68%.

Other than the compound represented by General Formula (1), the material for the electron transport layer can be selected from well-known compounds to use. Examples of these compounds include a nitro-substituted fluorene derivative, a diphenylquinone derivative, a thiopyrandioxide derivative, carbodiimide, a fluorenylidenemethane derivative, anthraquinonedimethane, an anthrone derivative and an oxadiazole derivative. Further, a thiadiazole derivative formed in such a manner that an oxygen atom of an oxadiazole ring of the above-mentioned oxadiazole derivative is substituted by a sulfur atom and a quinoxaline derivative having a quinoxaline ring which is well-known as an electron withdrawing group can be used as the electron transport material. Further, polymer materials in each of which any of these materials is introduced into a polymer chain or constitutes a main chain of a polymer can also be used.

Further, metal complexes of an 8-quinolinol derivative such as: tris(8-quinolinol)aluminum ($Alq_3$), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum and bis(8-quinolinol)zinc (Znq); and metal complexes formed in such a manner that central metal of the these metal complexes is substituted by In, Mg, Cu, Ca, Sn, Ga or Pb can also be used as the electron transport material. Further, metal-free or metal phthalocyanine and those formed in such a manner that the terminal of metal-free or metal phthalocyanine is substituted by an alkyl group, a sulfonic acid group or the like can be used as the electron transport material by preference. Further, the distyrylpyrazine derivative mentioned as an example of the material for the light emitting layer can also be used as the electron transport material, and as with the cases of the positive hole injection layer and the positive hole transfer layer, inorganic semiconductors such as an n type-Si and an n type-SiC can also be used as the electron transport material.

The electron transport layer can be formed by making the above-mentioned electron transport material a thin film by a well-known method such as the vacuum evaporation method, the spin coating method, the casting method, the printing method including the ink-jet method or the LB method. The thickness of the electron transport layer is not particularly limited, but it is generally within a range about from 5 nm to 5 μm, preferably within a range from 5 nm to 200 nm. The electron transport layer may have a single layer structure composed of one type or two or more types of the above-mentioned materials.

Further, an electron transport layer having high n property doped with impurities can be employed as the electron transport layer. Examples thereof include those described in documents such as Japanese Patent Application Laid-Open Publication Nos. 4-297076, 10-270172, 2000-196140 and 2001-102175 and J. Appl. Phys., 95, 5773 (2004).

In the present invention, employing an electron transport layer having high n property is preferable in view of producing an element which consumes lower electric power.

[Counter Electrode: Anode or Cathode]

For the counter electrode, the material constituting the above-described transparent conductive layer may be used, or a material having metal, an alloy, a conductive compound or a mixture thereof as an electrode substance can also be used. Examples of the electrode substance include sodium, sodium-potassium alloy, magnesium, lithium, magnesium/copper mixture, magnesium/argentum mixture, magnesium/aluminum mixture, magnesium/indium mixture, aluminum/aluminum oxide ($Al_2O_3$) mixture, indium, lithium/aluminum mixture and rare earth metal. The counter electrode can be produced by making the above-mentioned electrode substance a thin film by a method such as evaporation or sputtering. The sheet resistance of the counter electrode is preferably several hundred Ω/□ or less. The thickness thereof is generally within a range from 10 nm to 5 μm, preferably within a range from 50 nm to 200 nm.

<<Application>>

The organic EL element of the present invention is applicable to a display device, a display or light emitting sources of various types. Examples of the light emitting sources include, but are not limited to, a home lighting fixture, a car lighting fixture, a backlight for a timepiece or a liquid crystal, a signboard for advertisement, a signal, alight source for an optical storage medium, a light source for an electrophotographic copier, a light source for an optical communication processor and a light source for an optical sensor. In particular, it can be effectively used as a backlight for a liquid crystal display device which is combined with a color filter and as a light source for a lighting fixture.

The present invention is detailed with examples below. However, the present invention is not limited thereto. In the following examples, "unit" or "%" is used. The "unit" or "%" indicates "parts mass" or "parts %", if not otherwise specified.

EXAMPLE 1

<<Production of Top-and-Bottom Emission Type Organic EL Element>>

Organic El elements 1-1 to 1-26 were each produced in such a way as to have a light emitting area of 5 cm×5 cm.

[Production of Organic EL Element 1-1]

(Formation of Anode)

ITO was deposited on a transparent substrate 1 by sputtering under a condition of making the thickness thereof be 100 nm and then subjected to patterning, so that an anode constituted of an ITO layer was formed. Next, the substrate provided with the ITO layer was subjected to ultrasonic cleaning with isopropyl alcohol, dried with dry nitrogen gas, and then subjected to UV ozone cleaning for five minutes.

(Formation of Positive Hole Injection Layer to Electron Transport Layer)

The substrate provided with the ITO layer was fixed onto a substrate holder of a commercial vacuum evaporation device. Then, the below-mentioned α-NPD, DPVBi, BAlq, $Alq_3$ and potassium fluoride were placed in tantalum resistive heating boats, respectively, and the tantalum resistive heating boats were mounted on a first vacuum tank of the vacuum evaporation device.

In addition, aluminum was placed in a tungsten resistive heating boat, and the tungsten resistive heating boat was mounted on a second vacuum tank of the vacuum evaporation device.

[Chem. 47]

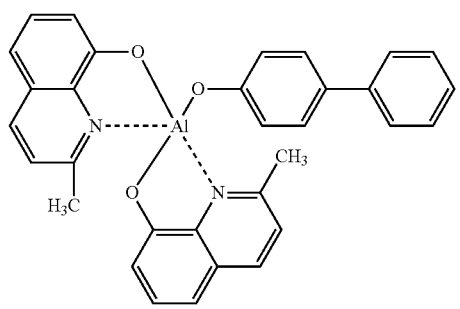

BAlq

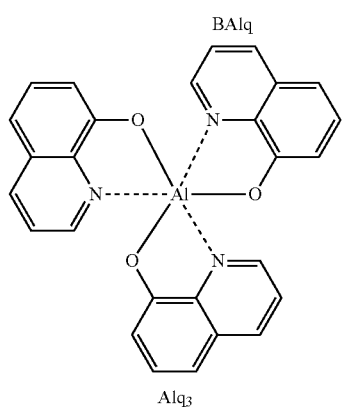

Alq₃

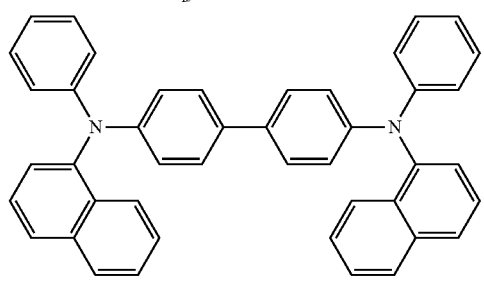

α-NPD

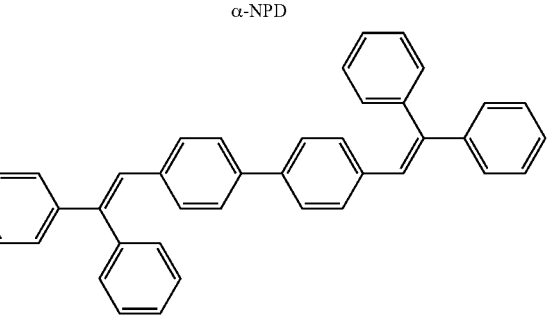

DPVBi

H4

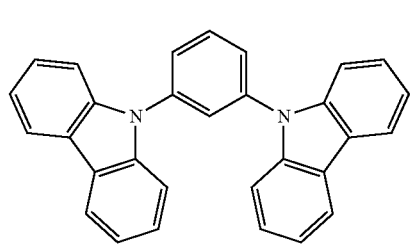

First, after the pressure of the first vacuum tank was reduced to $4 \times 10^{-4}$ Pa, the heating boat having α-NPD therein was electrically heated, and a positive hole injection/ positive hole transport layer having a thickness of 20 nm was provided on the ITO layer at a deposition rate of 0.1-0.2 nm/sec.

In addition, the heating boat having DPVBi therein was electrically heated, and a light emitting layer having a thickness of 30 nm was provided at a deposition rate of 0.1-0.2 nm/sec.

Subsequently, the heating boat having BAlq therein was electrically heated, and a positive hole block layer having a thickness of 10 nm was provided at a deposition rate of 0.1-0.2 nm/sec. In addition, the heating boat having $Alq_3$ therein was electrically heated, and an electron transport layer having a thickness of 20 nm was provided at a deposition rate of 0.1-0.2 nm/sec.

(Formation of Electron Injection Layer)

Next, the heating boat having potassium fluoride therein was electrically heated, and a potassium fluoride layer having a thickness of 1 nm was provided at a deposition rate of 0.01-0.02 nm/sec. The element in which the layers up to the potassium fluoride layer had been formed was transferred to the second vacuum tank while maintaining the vacuum state. After the pressure of the second vacuum tank was reduced to $4\times10^{-4}$ Pa, the heating boat having aluminum therein was electrified, and an aluminum layer having a thickness of 5 nm was formed at a deposition rate of 0.1-0.2 nm/sec. Thus, an electron injection layer was provided.

(Formation of Transparent Conductive Layer (Cathode))

Next, the element in which the layers up to the electron injection layer had been formed was transferred to a commercial parallel plate sputtering device to which an ITO target had been attached in advance. After the pressure inside a chamber of the sputtering device was reduced to $5\times10^{-3}$ Pa, electricity was discharged at DC power of 500 W while nitrogen gas and oxygen gas were discharged, so that a transparent conductive layer (cathode) constituted of an ITO conductive layer having a thickness of 100 nm was formed at a deposition rate of 10 nm/sec.

(Sealing of Element)

Lastly, the obtained element was covered with a glass case, a glass substrate having a thickness of 300 μm was used as a sealing substrate, and an epoxy-based light curable adhesive (LUXTRAK LC0629B produced by Toagosei Co., Ltd.) was applied to the periphery as a sealing material. The element was brought into close contact with the transparent supporting substrate and irradiated with UV light from the glass substrate side, whereby curing/sealing was carried out. Thus, the top-and-bottom emission type organic EL element 1-1 was produced.

[Production of Organic EL Element 1-2]

(Formation of Anode to Electron Injection Layer)

Formation of the anode to up the electron injection layer was carried out in the same manner as that of the organic EL element 1-1.

(Formation of Transparent Protective Layer)

Next, the element in which the layers up to the electron injection layer had been formed was returned to the first vacuum tank while maintaining the vacuum state. After the pressure of the first vacuum tank was reduced to $4\times10^{-4}$ Pa, without introduction of oxygen gas into the vacuum evaporation device, a heating boat having calcium oxide CaO therein was electrically heated, and a transparent protective layer having a thickness of 20 nm was provided at a deposition rate of 0.1-0.2 nm/sec. The transparent protective layer of an element separately produced in the same manner was analyzed by ESCA, and it was found that calcium oxide constituting the transparent protective layer was in the oxygen deficient state (non-stoichiometric composition).

(Formation of Cathode)

Formation of the cathode was carried out in the same manner as that of the organic EL element 1-1.

(Sealing of Element)

Curing/Sealing was carried out in the same manner as that of the organic EL element 1-1. Thus, the top-and-bottom emission type organic EL element 1-2 was produced.

[Production of Organic EL Element 1-3]

The top-and-bottom emission type organic EL element 1-3 was produced in the same manner as that of the organic EL element 1-2, except that the thickness of the transparent protective layer was changed from 20 nm to 70 nm.

[Production of Organic EL Element 1-4]

The top-and-bottom emission type organic EL element 1-4 was produced in the same manner as that of the organic EL element 1-2, except that the material of the transparent protective layer was changed from calcium oxide to lanthanum oxide.

The transparent protective layer was analyzed by ESCA, and it was confirmed that lanthanum oxide constituting the transparent protective layer was in the oxygen deficient state.

[Production of Organic EL Element 1-5]

The top-and-bottom emission type organic EL element 1-5 was produced in the same manner as that of the organic EL element 1-4, except that the thickness of the transparent protective layer was changed from 20 nm to 70 nm.

[Production of Organic EL Element 1-6]

(Formation of Anode)

Formation of the anode constituted of the ITO layer was carried out in the same manner as that of the organic EL element 1-1.

(Formation of Positive Hole Injection Layer to Electron Transport Layer)

The substrate provided with the ITO layer was fixed onto the substrate holder of the commercial vacuum evaporation device. Then, the above-mentioned α-NPD, H4, Ir-4, BAlq, $Alq_3$ and vanadium oxide were placed in tantalum resistive heating boats, respectively, and the tantalum resistive heating boats were mounted on the first vacuum tank of the vacuum evaporation device.

In addition, aluminum was placed in a tungsten resistive heating boat, and the tungsten resistive heating boat was mounted on the second vacuum tank of the vacuum evaporation device.

First, after the pressure of the first vacuum tank was reduced to $4\times10^{-4}$ Pa, the heating boat having α-NPD therein was electrically heated, and a positive hole injection/positive hole transport layer having a thickness of 20 nm was provided on the ITO layer at a deposition rate of 0.1-0.2 nm/sec.

In addition, the heating boats having H4 and Ir-4 therein, respectively, were independently electrified, and a deposition rate of H4 as a light emitting host and a deposition rate of Ir-4 as a light emitting dopant were regulated to be 100:6, so that a light emitting layer having a thickness of 30 nm was provided.

Next, the heating boat having BAlq therein was electrically heated, and a positive hole block layer having a thickness of 10 nm was provided at a deposition rate of 0.1-0.2 nm/sec. In addition, the heating boat having $Alq_3$ therein was electrically heated, and an electron transport layer having a thickness of 20 nm was provided at a deposition rate of 0.1-0.2 nm/sec.

(Formation of Electron Injection Layer)

Next, the heating boat having potassium fluoride therein was electrically heated, and a potassium fluoride layer having a thickness of 1 nm was provided at a deposition rate of 0.01-0.02 nm/sec. The element in which the layers up to the potassium fluoride layer had been formed was transferred to the second vacuum tank while maintaining the vacuum state. After the pressure of the second vacuum tank was reduced to $4\times10^{-4}$ Pa, the heating boat having aluminum therein was electrified, and an aluminum layer having a thickness of 5 nm was formed at a deposition rate of 0.1-0.2 nm/sec. Thus an electron injection layer was provided.

(Formation of Transparent Protective Layer)

Next, the element in which the layers up to the electron injection layer had been formed was returned to the first vacuum tank while maintaining the vacuum state. After the pressure of the first vacuum tank was reduced to $4\times10^{-4}$ Pa, the heating boat having vanadium oxide therein was electrically heated, and a transparent protective layer having a thickness of 20 nm was provided at a deposition rate of 0.1-0.2 nm/sec.

The transparent protective layer of an element separately produced in the same manner was analyzed by ESCA, and it was found that vanadium oxide constituting the transparent protective layer was in the oxygen deficient state (non-stoichiometric composition).

(Formation of Transparent Conductive Layer (Cathode))

Next, the element in which the layers up to the transparent protective layer had been formed was transferred to the commercial parallel plate sputtering device to which an ITO target had been attached in advance. After the pressure inside the chamber of the sputtering device was reduced to $5\times10^{-3}$ Pa, electricity was discharged at DC power of 500 W while nitrogen gas and oxygen gas were discharged, so that a transparent conductive layer (cathode) constituted of an ITO conductive layer having a thickness of 100 nm was formed at a deposition rate of 10 nm/sec.

(Sealing of Element)

Curing/Sealing was carried out in the same manner as that of the organic EL element 1-1. Thus, the top-and-bottom emission type organic EL element 1-6 was produced.

[Production of Organic EL Element 1-7]

(Formation of Anode to Electron Injection Layer)

Formation of the anode up to the electron injection layer was carried out in the same manner as that of the organic EL element 1-6.

(Formation of Transparent Protective Layer)

Next, the element in which the layers up to the electron injection layer had been formed was returned to the first vacuum tank while maintaining the vacuum state. After the pressure of the first vacuum tank was reduced to $4\times10^{-4}$ Pa, a heating boat having molybdenum (VI) oxide therein was electrically heated, and a transparent protective layer having a thickness of 20 nm was provided at a deposition rate of 0.1-0.2 nm/sec.

(Formation of Cathode)

Formation of the cathode was carried out in the same manner as that of the organic EL element 1-6.

(Sealing of Element)

Curing/Sealing was carried out in the same manner as that of the organic EL element 1-6. Thus, the top-and-bottom emission type organic EL element 1-7 was produced. The transparent protective layer of an element separately produced in the same manner was analyzed by ESCA, and it was confirmed that molybdenum (VI) oxide constituting the transparent protective layer was in the oxygen deficient state.

[Production of Organic EL Element 1-8 to 1-12]

The organic EL elements 1-8 to 1-12 were each produced in the same manner as that of the organic EL element 1-7, except that the thickness of the transparent protective layer was changed to a value shown in TABLE 1.

[Production of Organic EL Element 1-13 to 1-15]

The organic EL elements 1-13 to 1-15 were each produced in the same manner as that of the organic EL element 1-9, except that the compound of the electron transport layer was changed to a compound shown in TABLE 1.

[Production of Organic EL Element 1-16 to 1-18]

The organic EL elements 1-16 to 1-18 were each produced in the same manner as that of the organic EL element 1-15, except that the phosphorescence emitting compound was changed to a compound shown in TABLE 1.

[Production of Organic EL Element 1-19 to 1-20]

The organic EL elements 1-19 to 1-20 were each produced in the same manner as that of the organic EL element 1-18, except that the material of the transparent protective layer was changed to a material shown in TABLE 1. The molybdenum oxide, rhenium oxide and nickel oxide shown in TABLE 1 are molybdenum (VI) oxide, rhenium (VI) oxide and nickel (II) oxide, respectively.

[Production of Organic EL Element 1-21]

(Formation of Anode to Cathode)

Formation of the anode up to the cathode was carried out in the same manner as that of the organic EL element 1-18.

(Production of Auxiliary Electrode)

On the cathode, an auxiliary electrode in a line-shaped argent pattern having a line width of 50 μm, a thickness of 1 μm and a pitch distance of 1,000 μm was produced by sputtering using a shadow mask.

(Sealing of Element)

Curing/Sealing was carried out in the same manner as that of the organic EL element 1-18. Thus, the top-and-bottom emission type organic EL element 1-21 was produced.

[Production of Organic EL Element 1-22 to 1-23]

The organic EL elements 1-22 to 1-23 were each produced in the same manner as that of the organic EL element 1-21, except that the material of the transparent protective layer was changed to a material shown in TABLE 1.

[Production of Organic EL Element 1-24]

(Formation of Anode to Electron Injection Layer)

Formation of the anode up to the electron injection layer was carried out in the same manner as that of the organic EL element 1-18.

(Formation of Transparent Protective Layer)

Next, after the element in which the layers up to the electron injection layer had been formed was returned to the first vacuum tank while maintaining the vacuum state, a stainless steel mask was set on the electron injection layer by remote control from the outside of the device. The mask used here had line-shaped holes at 50 μm intervals, the line-shaped holes each having a width of 1,000 μm. Next, after the pressure of the second vacuum tank was reduced to $4\times10^{-4}$ Pa, a heating boat having molybdenum (VI) oxide therein was electrically heated, and deposition was carried out at a deposition rate of 0.1-0.2 nm/sec. via the mask, so that a patterned transparent protective layer having a thickness of 70 nm shown in the schematic diagram of FIG. 2 was provided. The transparent protective layer is shown in a top view and a cross-sectional view from a side.

(Production of Auxiliary Electrode)

Figure 2A:
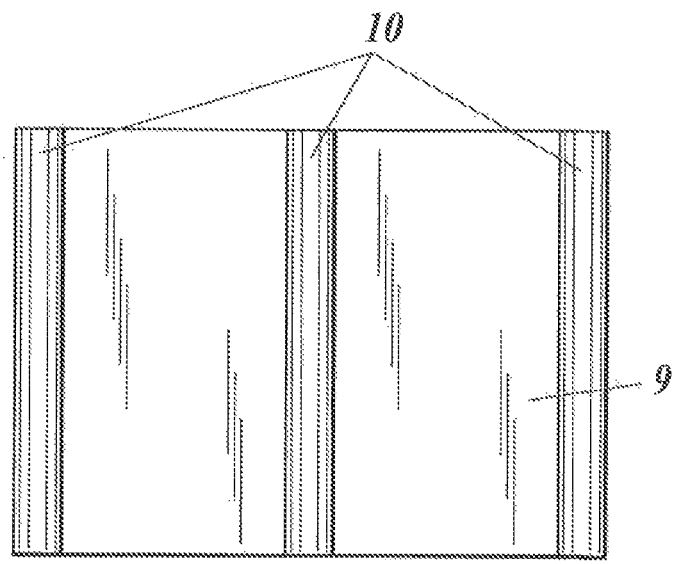
FIG. 2A is a top view showing an example of a top-and-bottom emission type organic EL element having an auxiliary electrode.
Figure 2B:
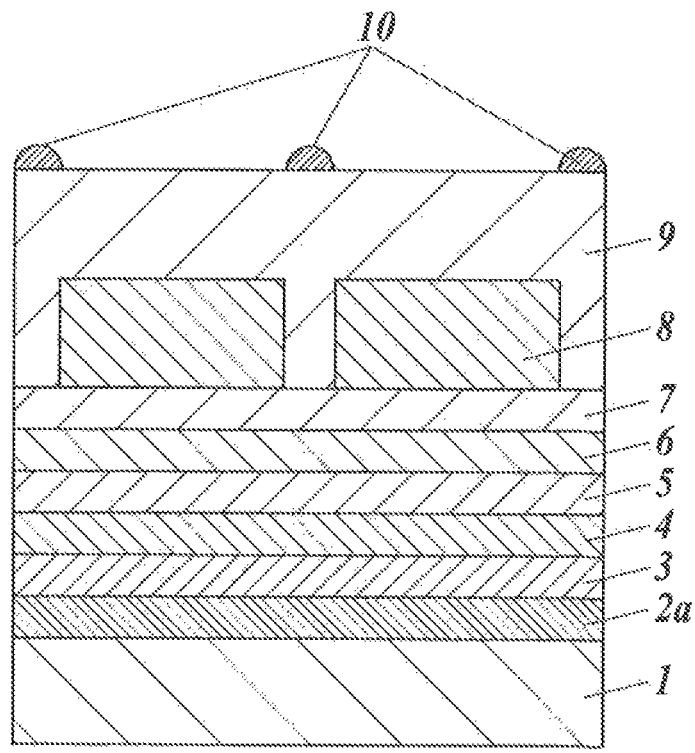
FIG. 2B is a cross-sectional view showing the example of the top-and-bottom emission type organic EL element having the auxiliary electrode.

On the cathode, an auxiliary electrode in a line-shaped argent pattern having a line width of 50 μm, a thickness of 1 μm and a pitch distance of 1,000 μm shown in FIG. 2 was produced by sputtering using a shadow mask above the non-patterned region of the transparent protective layer.

(Sealing of Element)

Curing/Sealing was carried out in the same manner as that of the organic EL element 1-18. Thus, the top-and-bottom emission type organic EL element 1-24 was produced.

[Production of Organic EL Element 1-25 to 1-26]

The organic EL elements 1-25 to 1-26 were each produced in the same manner as that of the organic EL element 1-24, except that the material of the transparent protective layer was changed to a material shown in TABLE 1.

With respect to each of the transparent protective layers of the samples 1-8 to 1-26 too, the oxygen deficient state was confirmed by ESCA.

<<Evaluation of Organic EL Element>>

With respect to each of the produced organic EL elements, a voltage was measured by the following method.

[Measurement of Voltage]

The voltage of the time when the sum of values of front brightness of both sides, i.e., the anode side and the cathode side, was 1000 cd/m$^2$ was taken as a voltage of each of the produced organic EL elements. The brightness was measured by using a spectroradiometer CS-1000 (produced by Konica Minolta Sensing Inc.). The smaller the obtained value of the voltage is, the more favorable result it means.

The obtained results are shown in TABLE 1.

(External Extraction Quantum Efficiency)

The external extraction quantum efficiency (%) of the time when a constant current was applied to each of the produced organic EL elements at 2.5 mA/cm$^2$ was measured. The external extraction quantum efficiency is calculated by the following equation.

External extraction quantum efficiency (%)=the number of photons emitted to the outside of an organic EL element/the number of electrons discharged to the organic EL element×100

The measurement was carried out by using a spectroradiometer CS-1000 (produced by Konica Minolta Sensing Inc.). The external extraction quantum efficiency of each of the organic EL elements 1-1 to 1-26 was expressed by a relative value with a measured value of the organic EL element 1-1 (comparative example) as 1.0. The relative values of the external extraction quantum efficiency are shown in TABLE 1.

TABLE 1

| | STRUCTURE OF EXAMPLE | | | | | | | EVALUATION RESULT | | | |
|---|---|---|---|---|---|---|---|---|---|---|---|
| | TRANSPARENT PROTECTIVE LAYER | | | | | | | | | | |
| *1 | MATERIAL | *2 | PATTERN-ING | *3 (nm) | *4 MATERIAL | *6 | *5 *7 | AUXILIARY ELECTRODE | VOLTAGE (V) | EFFICIENCY (RELATIVE VALUE) | REMARK |
| 1-1 | — | — | NO | — | Alq3 | — | DPVBi | NO | 26.1 | 1.0 | *8 |
| 1-2 | CALCIUM OXIDE | YES | NO | 20 | Alq3 | — | DPVBi | NO | 20.2 | 1.2 | *8 |
| 1-3 | CALCIUM OXIDE | YES | NO | 70 | Alq3 | — | DPVBi | NO | 26.2 | 1.1 | *8 |
| 1-4 | LANTHANUM OXIDE | YES | NO | 20 | Alq3 | — | DPVBi | NO | 21.4 | 1.2 | *8 |
| 1-5 | LANTHANUM OXIDE | YES | NO | 70 | Alq3 | — | DPVBi | NO | 24.8 | 1.1 | *8 |
| 1-6 | VANADIUM OXIDE | YES | NO | 20 | Alq3 | Ir-4 | — | NO | 24.2 | 1.6 | *8 |
| 1-7 | MOLYBDENUM OXIDE | YES | NO | 20 | Alq3 | Ir-4 | — | NO | 12.7 | 3.1 | *9 |
| 1-8 | MOLYBDENUM OXIDE | YES | NO | 30 | Alq3 | Ir-4 | — | NO | 10.6 | 3.6 | *9 |
| 1-9 | MOLYBDENUM OXIDE | YES | NO | 70 | Alq3 | Ir-4 | — | NO | 8.7 | 4.4 | *9 |
| 1-10 | MOLYBDENUM OXIDE | YES | NO | 100 | Alq3 | Ir-4 | — | NO | 8.9 | 4.5 | *9 |
| 1-11 | MOLYBDENUM OXIDE | YES | NO | 150 | Alq3 | Ir-4 | — | NO | 9.2 | 4.3 | *9 |
| 1-12 | MOLYBDENUM OXIDE | YES | NO | 180 | Alq3 | Ir-4 | — | NO | 10.2 | 3.8 | *9 |
| 1-13 | MOLYBDENUM OXIDE | YES | NO | 70 | COMPOUND(99) | Ir-4 | — | NO | 8.0 | 4.8 | *9 |
| 1-14 | MOLYBDENUM OXIDE | YES | NO | 70 | COMPOUND(94) | Ir-4 | — | NO | 7.5 | 5.1 | *9 |
| 1-15 | MOLYBDENUM OXIDE | YES | NO | 70 | COMPOUND(10) | Ir-4 | — | NO | 6.6 | 5.9 | *9 |
| 1-16 | MOLYBDENUM OXIDE | YES | NO | 70 | COMPOUND(10) | Ir-12 | — | NO | 6.1 | 6.3 | *9 |
| 1-17 | MOLYBDENUM OXIDE | YES | NO | 70 | COMPOUND(10) | Ir-24 | — | NO | 5.1 | 7.6 | *9 |
| 1-18 | MOLYBDENUM OXIDE | YES | NO | 70 | COMPOUND(10) | Ir-26 | — | NO | 5.1 | 7.7 | *9 |
| 1-19 | RHENIUM OXIDE | YES | NO | 70 | COMPOUND(10) | Ir-26 | — | NO | 5.0 | 7.8 | *9 |
| 1-20 | NICKEL OXIDE | YES | NO | 70 | COMPOUND(10) | Ir-26 | — | NO | 5.2 | 7.5 | *9 |
| 1-21 | MOLYBDENUM OXIDE | YES | NO | 70 | COMPOUND(10) | Ir-26 | — | YES | 4.6 | 8.4 | *9 |
| 1-22 | RHENIUM OXIDE | YES | NO | 70 | COMPOUND(10) | Ir-26 | — | YES | 4.5 | 8.6 | *9 |
| 1-23 | NICKEL OXIDE | YES | NO | 70 | COMPOUND(10) | Ir-26 | — | YES | 4.7 | 8.4 | *9 |

TABLE 1-continued

| | | STRUCTURE OF EXAMPLE | | | | | | EVALUATION RESULT | | | |
|---|---|---|---|---|---|---|---|---|---|---|---|
| | TRANSPARENT PROTECTIVE LAYER | | | | | | | | | | |
| *1 | MATERIAL | *2 | PAT-TERN-ING | *3 (nm) | *4 MATERIAL | *6 | *7 | AUXILIARY ELECTRODE | VOLTAGE (V) | EFFICIENCY (RELATIVE VALUE) | REMARK |
| 1-24 | MOLYBDENUM OXIDE | YES | YES | 70 | COMPOUND(10) | Ir-26 | — | YES | 4.1 | 9.0 | *9 |
| 1-25 | RHENIUM OXIDE | YES | YES | 70 | COMPOUND(10) | Ir-26 | — | YES | 4.0 | 9.1 | *9 |
| 1-26 | NICKEL OXIDE | YES | YES | 70 | COMPOUND(10) | Ir-26 | — | YES | 4.2 | 8.9 | *9 |

*1: ORGANIC EL ELEMENT
*2: OXYGEN DEFICIENT STATE
*3: THICKNESS
*4: ELECTRON TRANSPORT LAYER
*5: LIGHT EMITTING LAYER DOPANT
*6: PHOSPHORESCENT MATERIAL
*7: FLUORESCENT MATERIAL
*8: COMPARATIVE EXAMPLE
*9: PRESENT INVENTION EXAMPLE

As it is obvious from the results shown in TABLE 1, the organic EL elements of the examples of the present invention are excellent in the light emission efficiency and the driving voltage as compared with the comparative examples.

EXAMPLE 2

<<Production of Top Emission Type Organic EL Element>>

Organic El elements 2-1 to 2-23 were each produced in such a way as to have a light emitting area of 5 cm×5 cm.

[Production of Organic EL Element 2-1]

(Formation of Cathode)

Aluminum was deposited on a transparent substrate 1 by sputtering under a condition of making the thickness thereof be 100 nm and then subjected to patterning, so that a cathode constituted of an aluminum layer was formed. Next, the substrate provided with the aluminum layer was subjected to ultrasonic cleaning with isopropyl alcohol, dried with dry nitrogen gas, and then subjected to UV ozone cleaning for five minutes.

(Formation of Electron Injection Layer to Positive Hole Injection/Positive Hole Transport Layer)

The substrate provided with the aluminum layer was fixed onto the substrate holder of the commercial vacuum evaporation device. Then, potassium fluoride, $Alq_3$, BAlq, DPVBi and α-NPD were placed in tantalum resistive heating boats, respectively, and the tantalum resistive heating boats were mounted on the first vacuum tank of the vacuum evaporation device.

First, after the pressure of the first vacuum tank was reduced to $4 \times 10^{-4}$ Pa, the heating boat having potassium fluoride therein was electrically heated, and an electron injection layer having a thickness of 1 nm was provided on the aluminum layer at a deposition rate of 0.01-0.02 nm/sec.

Next, the heating boat having $Alq_3$ therein was electrically heated, and an electron transport layer having a thickness of 20 nm was provided at a deposition rate of 0.1-0.2 nm/sec.

In addition, the heating boat having DPVBi therein was electrically heated, and a light emitting layer having a thickness of 30 nm was provided at a deposition rate of 0.1-0.2 nm/sec.

Next, the heating boat having BAlq therein was electrically heated, and an electron block layer having a thickness of 10 nm was provided at a deposition rate of 0.1-0.2 nm/sec.

In addition, the heating boat having α-NPD therein was electrically heated, and a positive hole injection/positive hole transport layer having a thickness of 20 nm was provided at a deposition rate of 0.1-0.2 nm/sec.

(Formation of Transparent Conductive Layer (Anode))

Next, the element in which the layers up to the positive hole injection/positive hole transport layer had been formed was transferred to the commercial parallel plate sputtering device to which an ITO target had been attached in advance. After the pressure inside the chamber of the sputtering device was reduced to $5 \times 10^{-3}$ Pa, electricity was discharged at DC power of 500 W while nitrogen gas and oxygen gas were discharged, so that a transparent conductive layer (anode) constituted of an ITO conductive layer having a thickness of 100 nm was formed at a deposition rate of 10 nm/sec.

(Sealing of Element)

Lastly, the obtained element was covered with a glass case, a glass substrate having a thickness of 300 μm was used as a sealing substrate, and an epoxy-based light curable adhesive (LUXTRAK LC0629B produced by Toagosei Co., Ltd.) was applied to the periphery as a sealing material. The element was brought into close contact with the transparent supporting substrate and irradiated with UV light from the glass substrate side, whereby curing/sealing was carried out. Thus, the top emission type organic EL element 2-1 was produced.

[Production of Organic EL Element 2-2]

(Formation of Cathode to Positive Hole Injection/Positive Hole Transport Layer)

Formation of the cathode up to the positive hole injection/positive hole transport layer was carried out in the same manner as that of the organic EL element 2-1.

(Formation of Transparent Protective Layer)

Next, the element in which the layers up to the positive hole injection/positive hole transport layer had been formed was returned to the first vacuum tank while maintaining the vacuum state. After the pressure of the first vacuum tank was reduced to $4 \times 10^{-4}$ Pa, a heating boat having calcium oxide therein was electrically heated, and a transparent protective layer having a thickness of 20 nm was provided at a deposition rate of 0.1-0.2 nm/sec without introduction of oxygen gas.

(Formation of Anode)

Formation of the anode was carried out in the same manner as that of the organic EL element 2-1.

(Sealing of Element)

Curing/Sealing was carried out in the same manner as that of the organic EL element 2-1. Thus, the top emission type organic EL element 2-2 was produced.

[Production of Organic EL Element 2-3]

The top emission type organic EL element 2-3 was produced in the same manner as that of the organic EL element 2-2, except that the thickness of the transparent protective layer was changed from 20 nm to 70 nm.

[Production of Organic EL Element 2-4]

The top emission type organic EL element 2-4 was produced in the same manner as that of the organic EL element 2-2, except that the material of the transparent protective layer was changed from calcium oxide to lanthanum oxide.

[Production of Organic EL Element 2-5]

The top emission type organic EL element 2-5 was produced in the same manner as that of the organic EL element 2-4, except that the thickness of the transparent protective layer was changed from 20 nm to 70 nm.

[Production of Organic EL Element 2-6]

(Formation of Cathode)

Formation of the cathode constituted of the aluminum layer was carried out in the same manner as that of the organic EL element 2-1.

(Formation of Electron Injection Layer to Positive Hole Injection/Positive Hole Transport Layer)

The substrate provided with the aluminum layer was fixed onto the substrate holder of the commercial vacuum evaporation device. Then, potassium fluoride, $Alg_3$, BAlq, H4, Ir-4 and α-NPD were placed in tantalum resistive heating boats, respectively, and the tantalum resistive heating boats were mounted on the first vacuum tank of the vacuum evaporation device.

First, after the pressure of the first vacuum tank was reduced to $4 \times 10^{-4}$ Pa, the heating boat having potassium fluoride therein was electrically heated, and an electron injection layer having a thickness of 1 nm was provided on the aluminum layer at a deposition rate of 0.01-0.02 nm/sec.

Next, the heating boat having $Alg_3$ therein was electrically heated, and an electron transport layer having a thickness of 20 nm was provided at a deposition rate of 0.1-0.2 nm/sec.

In addition, the heating boats having H4 and Ir-4 therein, respectively, were independently electrified, and a deposition rate of H4 as a light emitting host and a deposition rate of Ir-4 as a light emitting dopant were regulated to be 100:6, so that a light emitting layer having a thickness of 30 nm was provided.

Subsequently, the heating boat having BAlq therein was electrically heated, and a positive hole block layer having a thickness of 10 nm was provided at a deposition rate of 0.1-0.2 nm/sec. In addition, the heating boat having α-NPD therein was electrically heated, and a positive hole injection/positive hole transport layer having a thickness of 20 nm was provided at a deposition rate of 0.1-0.2 nm/sec.

(Formation of Transparent Protective Layer)

Next, the element in which the layers up to the positive hole injection/positive hole transport layer had been formed was returned to the first vacuum tank while maintaining the vacuum state. After the pressure of the first vacuum tank was reduced to $4 \times 10^{-4}$ Pa, a heating boat having vanadium oxide therein was electrically heated, and a transparent protective layer having a thickness of 20 nm was provided at a deposition rate of 0.1-0.2 nm/sec.

(Formation of Transparent Conductive Layer (Anode))

Next, the element in which the layers up to the transparent protective layer had been formed was transferred to the commercial parallel plate sputtering device to which an ITO target had been attached in advance. After the pressure inside the chamber of the sputtering device was reduced to $5 \times 10^{-3}$ Pa, electricity was discharged at DC power of 500 W while nitrogen gas and oxygen gas were discharged, so that a transparent conductive layer (anode) constituted of an ITO conductive layer having a thickness of 100 nm was formed at a deposition rate of 10 nm/sec.

(Sealing of Element)

Curing/Sealing was carried out in the same manner as that of the organic EL element 2-1. Thus, the top emission type organic EL element 2-6 was produced.

[Production of Organic EL Element 2-7]

(Formation of Cathode to Positive Hole Injection/Positive Hole Transport Layer)

Formation of the cathode up to the positive hole injection/positive hole transport layer was carried out in the same manner as that of the organic EL element 2-6.

(Formation of Transparent Protective Layer)

Next, the element in which the layers up to the positive hole injection/positive hole transport layer had been formed was returned to the first vacuum tank while maintaining the vacuum state. After the pressure of the first vacuum tank was reduced to $4 \times 10^{-4}$ Pa, a heating boat having molybdenum (VI) oxide therein was electrically heated, and a transparent protective layer having a thickness of 20 nm was provided at a deposition rate of 0.1-0.2 nm/sec.

(Formation of Anode)

Formation of the anode was carried out in the same manner as that of the organic EL element 2-6.

(Sealing of Element)

Curing/Sealing was carried out in the same manner as that of the organic EL element 2-6. Thus, the top emission type organic EL element 2-7 was produced. The transparent protective layer of an element separately produced in the same manner was analyzed by ESCA, and it was confirmed that molybdenum (VI) oxide constituting the transparent protective layer was in the oxygen deficient state.

[Production of Organic EL Element 2-8 to 2-12]

The organic EL elements 2-8 to 2-12 were each produced in the same manner as that of the organic EL element 2-7, except that the thickness of the transparent protective layer was changed to a value shown in TABLE 2.

[Production of Organic EL Element 2-13 to 2-15]

The organic EL elements 2-13 to 2-15 were each produced in the same manner as that of the organic EL element 2-9, except that the phosphorescence emitting compound was changed to a compound shown in TABLE 2.

[Production of Organic EL Element 2-16 to 2-17]

The organic EL elements 2-16 to 2-17 were each produced in the same manner as that of the organic EL element 2-15, except that the material of the transparent protective layer was changed to a material shown in TABLE 2. The molybdenum oxide, rhenium oxide and nickel oxide shown in TABLE 2 are molybdenum (VI) oxide, rhenium (VI) oxide and nickel (II) oxide, respectively.

[Production of Organic EL Element 2-18]

(Formation of Cathode to Anode)

Formation of the cathode up to the anode was carried out in the same manner as that of the organic EL element 2-15.

(Production of Auxiliary Electrode)

On the anode, an auxiliary electrode in a line-shaped argent pattern having a line width of 50 μm, a thickness of 1 μm and a pitch distance of 1,000 μm was produced by sputtering using a shadow mask.

(Sealing of Element)

Curing/Sealing was carried out in the same manner as that of the organic EL element 2-15. Thus, the top emission type organic EL element 2-18 was produced.

[Production of Organic EL Element 2-19 to 2-20]

The organic EL elements 2-19 to 2-20 were each produced in the same manner as that of the organic EL element 2-15, except that the material of the transparent protective layer was changed to a material shown in TABLE 2.

[Production of Organic EL Element 2-21]

(Formation of Cathode to Positive Hole Injection/Positive Hole Transport Layer)

Formation of the cathode up to the positive hole injection/positive hole transport layer was carried out in the same manner as that of the organic EL element 2-18.

(Formation of Transparent Protective Layer)

Figure 3A:
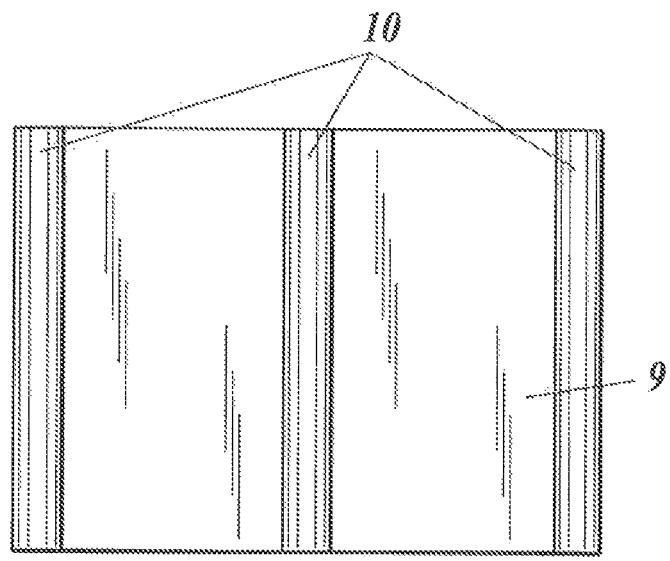
FIG. 3A is a top view showing an example of a top emission type organic EL element having an auxiliary electrode.
Figure 3B:
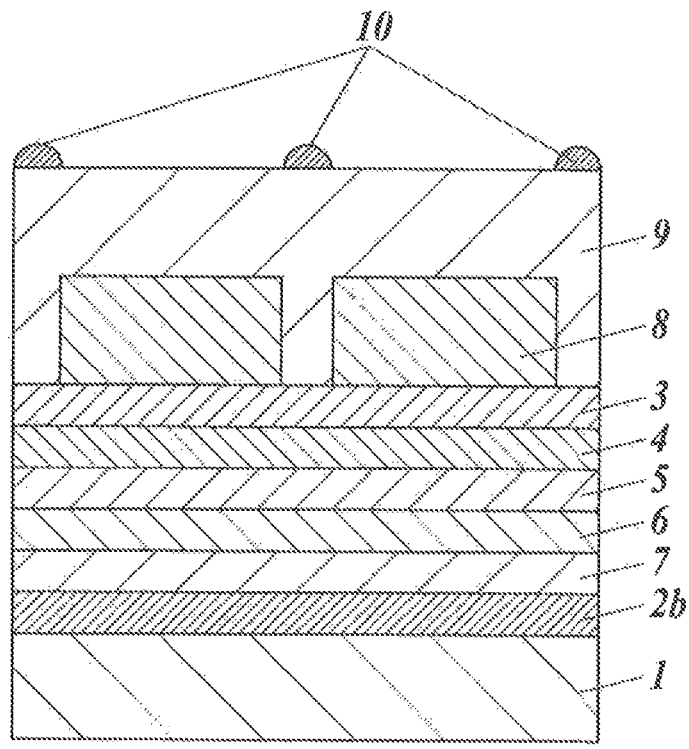
FIG. 3B is a cross-sectional view showing the example of the top emission type organic EL element having the auxiliary electrode.

Next, after the element in which the layers up to the positive hole injection/positive hole transport layer had been formed was returned to the first vacuum tank while maintaining the vacuum state, a stainless steel mask was placed on the positive hole injection/positive hole transport layer by remote control from the outside of the device. The mask used here had line-shaped holes at 50 μm intervals, the line-shaped holes each having a width of 1,000 μm. Next, after the pressure of the second vacuum tank was reduced to $4 \times 10^{-4}$ Pa, a heating boat having molybdenum (VI) oxide therein was electrically heated, and deposition was carried out at a deposition rate of 0.1-0.2 nm/sec. via the mask, so that a patterned transparent protective layer having a thickness of 70 nm shown in FIG. 3 was provided. FIG. 3 includes a top view and a cross-sectional view from a side.

(Production of Auxiliary Electrode)

On the cathode, an auxiliary electrode in a line-shaped argent pattern having a line width of 50 μm, a thickness of 1 μm and a pitch distance of 1,000 μm shown in FIG. 3 was produced by sputtering using a shadow mask above the non-patterned region of the transparent protective layer.

(Sealing of Element)

Curing/Sealing was carried out in the same manner as that of the organic EL element 2-15. Thus, the top emission type organic EL element 2-21 was produced.

[Production of Organic EL Element 2-22 to 2-23]

The organic EL elements 2-22 to 2-23 were each produced in the same manner as that of the organic EL element 2-21, except that the material of the transparent protective layer was changed to a material shown in TABLE 2.

With respect to each of the transparent protective layers of the samples 2-8 to 2-23 too, the oxygen deficient state was confirmed by ESCA.

<<Evaluation of Organic EL Element>>

With respect to each of the produced organic EL elements, a voltage was measured by the following method.

[Measurement of Voltage]

The voltage of the time when a value of front brightness of the anode side was 1000 cd/m² was taken as a voltage of each of the produced organic EL elements. The brightness was measured by using a spectroradiometer CS-1000 (produced by Konica Minolta Sensing Inc.). The smaller the obtained value of the voltage is, the more favorable result it means.

(External Extraction Quantum Efficiency)

The external extraction quantum efficiency (%) of the time when a constant current was applied to each of the produced organic EL elements at 2.5 mA/cm² was measured. The external extraction quantum efficiency is calculated by the following equation.

External extraction quantum efficiency (%)=the number of photons emitted to the outside of an organic EL element/the number of electrons discharged to the organic EL element×100

The measurement was carried out by using a spectroradiometer CS-1000 (produced by Konica Minolta Sensing Inc.). The external extraction quantum efficiency of each of the organic EL elements 2-1 to 2-23 was expressed by a relative value with a measured value of the organic EL element 2-1 (comparative example) as 1.0. The relative values of the external extraction quantum efficiency are shown in TABLE 2.

The obtained results are shown in TABLE 2.

TABLE 2

| | STRUCTURE OF EXAMPLE | | | | | | | EVALUATION RESULT | | |
| | TRANSPARENT PROTECTIVE LAYER | | | *4 | | *5 | AUXILIARY | | EFFICIENCY | |
| *1 | MATERIAL | *2 | PATTERNING | *3 (nm) | MATERIAL | *6 | *7 | ELECTRODE | VOLTAGE (V) | (RELATIVE VALUE) | REMARK |
|---|---|---|---|---|---|---|---|---|---|---|---|
| 2-1 | — | — | NO | — | α-NPD | — | DPVBi | NO | 29.2 | 1.0 | *8 |
| 2-2 | CALCIUM OXIDE | YES | NO | 20 | α-NPD | — | DPVBi | NO | 28.2 | 1.0 | *8 |
| 2-3 | CALCIUM OXIDE | YES | NO | 70 | α-NPD | — | DPVBi | NO | 30.2 | 1.0 | *8 |
| 2-4 | LANTHANUM OXIDE | YES | NO | 20 | α-NPD | — | DPVBi | NO | 28.4 | 1.0 | *8 |
| 2-5 | LANTHANUM OXIDE | YES | NO | 70 | α-NPD | — | DPVBi | NO | 29.8 | 1.0 | *8 |
| 2-6 | VANADIUM OXIDE | YES | NO | 20 | α-NPD | Ir-4 | — | NO | 28.7 | 1.5 | *8 |
| 2-7 | MOLYBDENUM OXIDE | YES | NO | 20 | α-NPD | Ir-4 | — | NO | 11.3 | 3.8 | *9 |
| 2-8 | MOLYBDENUM OXIDE | YES | NO | 30 | α-NPD | Ir-4 | — | NO | 9.3 | 4.7 | *9 |
| 2-9 | MOLYBDENUM OXIDE | YES | NO | 70 | α-NPD | Ir-4 | — | NO | 7.8 | 5.7 | *9 |
| 2-10 | MOLYBDENUM OXIDE | YES | NO | 100 | α-NPD | Ir-4 | — | NO | 8.0 | 5.5 | *9 |
| 2-11 | MOLYBDENUM OXIDE | YES | NO | 150 | α-NPD | Ir-4 | — | NO | 8.2 | 5.4 | *9 |

TABLE 2-continued

| *1 | \_\_\_\_\_STRUCTURE OF EXAMPLE\_\_\_\_\_ ||||| *5 | AUXILIARY ELECTRODE | EVALUATION RESULT |||
| | TRANSPARENT PROTECTIVE LAYER |||| *4 | | | EFFICIENCY |||
| | MATERIAL | *2 | PATTERNING | *3 (nm) | MATERIAL | *6 | *7 | | VOLTAGE (V) | (RELATIVE VALUE) | RE-MARK |
|---|---|---|---|---|---|---|---|---|---|---|---|
| 2-12 | MOLYBDENUM OXIDE | YES | NO | 180 | α-NPD | Ir-4 | — | NO | 9.2 | 4.9 | *9 |
| 2-13 | MOLYBDENUM OXIDE | YES | NO | 70 | α-NPD | Ir-12 | — | NO | 6.5 | 6.6 | *9 |
| 2-14 | MOLYBDENUM OXIDE | YES | NO | 70 | α-NPD | Ir-24 | — | NO | 5.0 | 8.7 | *9 |
| 2-15 | MOLYBDENUM OXIDE | YES | NO | 70 | α-NPD | Ir-26 | — | NO | 4.9 | 8.9 | *9 |
| 2-16 | RHENIUM OXIDE | YES | NO | 70 | α-NPD | Ir-26 | — | NO | 4.8 | 9.0 | *9 |
| 2-17 | NICKEL OXIDE | YES | NO | 70 | α-NPD | Ir-26 | — | NO | 5.1 | 8.5 | *9 |
| 2-18 | MOLYBDENUM OXIDE | YES | NO | 70 | α-NPD | Ir-26 | — | YES | 4.3 | 10.1 | *9 |
| 2-19 | RHENIUM OXIDE | YES | NO | 70 | α-NPD | Ir-26 | — | YES | 4.2 | 10.2 | *9 |
| 2-20 | NICKEL OXIDE | YES | NO | 70 | α-NPD | Ir-26 | — | YES | 4.4 | 9.8 | *9 |
| 2-21 | MOLYBDENUM OXIDE | YES | YES | 70 | α-NPD | Ir-26 | — | YES | 3.6 | 11.1 | *9 |
| 2-22 | RHENIUM OXIDE | YES | YES | 70 | α-NPD | Ir-26 | — | YES | 3.5 | 11.4 | *9 |
| 2-23 | NICKEL OXIDE | YES | YES | 70 | α-NPD | Ir-26 | — | YES | 3.7 | 10.9 | *9 |

*1: ORGANIC EL ELEMENT
*2: OXYGEN DEFICIENT STATE
*3: THICKNESS
*4: POSITIVE HOLE TRANSPORT LAYER
*5: LIGHT EMITTING LAYER DOPANT
*6: PHOSPHORESCENT MATERIAL
*7: FLUORESCENT MATERIAL
*8: COMPARATIVE EXAMPLE
*9: PRESENT INVENTION EXAMPLE

As it is obvious from the results shown in TABLE 2, the organic EL elements of the examples of the present invention are excellent in the light emission efficiency and the driving voltage as compared with the comparative examples.

INDUSTRIAL APPLICABILITY

The organic electroluminescence element of the present invention is applicable to a display device having a bright screen such as a television or a personal computer and an illumination device each of which emits light at a low voltage.

DESCRIPTION OF REFERENCE NUMERALS

1 Substrate
2a Anode
2b Cathode
3 Positive Hole Injection Layer
4 Positive Hole Transport Layer
5 Light Emitting Layer
6 Electron Transport Layer
7 Electron Injection Layer
8 Transparent Protective Layer
9 Transparent Conductive Layer
10 Auxiliary Electrode

The invention claimed is:

1. A top emission type organic electroluminescence element comprising:
    at least a light emitting layer;
    a transparent conductive layer as an electrode;
    a counter electrode which is non-transparent; and
    a transparent protective layer disposed between the light emitting layer and the transparent conductive layer, wherein
    the light emitting layer contains a phosphorescence emitting compound,
    the transparent protective layer contains a metal oxide,
    the metal oxide is a molybdenum (VI) oxide, a rhenium (VI) oxide or a nickel (II) oxide, and
    the molybdenum (VI) oxide, the rhenium (VI) oxide and the nickel (II) oxide are in an oxygen deficient state.

2. The organic electroluminescence element according to claim 1, wherein the transparent protective layer has a thickness of 60 nm to 150 nm.

3. The organic electroluminescence element according to claim 1 further comprising an electron transport layer between the light emitting layer and the transparent protective layer.

4. The organic electroluminescence element according to claim 1 further comprising a positive hole transport layer between the light emitting layer and the transparent protective layer.

5. The organic electroluminescence element according to claim 3, wherein the electron transport layer contains a compound represented by the following general formula (1):

$$(Ar1)_{n1}-Y1 \qquad \text{General Formula (1)}$$

wherein, provided that the compound represented by the general formula (1) has in a molecule at least two condensed aromatic heterocycles each formed in such a manner that three or more rings are condensed, n1 represents an integer of one or more; Y1 represents a substituent when n1 is one and represents a bond or an n1-valent linking group when n1 is two or more; and Ar1 represents a group represented by the following general formula (A), and a plurality of Ar1 are identical or different when n1 is two or more:

General Formula (A)

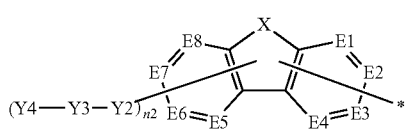

wherein X represents N(R), O, S or Si(R) (R'), E1 to E8 each represent C(R1) or N, and R, R' and R1 each represent a hydrogen atom, a substituent or a linking site with Y1; * represents a linking site with Y1; Y2 represents a bond or a divalent linking group; Y3 and Y4 each represent a group derived from a five-membered or six-membered aromatic ring, and at least one of Y3 and Y4 represents a group derived from an aromatic heterocycle containing a nitrogen atom as a ring constituent atom; and n2 represents an integer of one to four.

6. The organic eletroluninescence element according to claim 5, wherein the compound represented by the general formula (1) is a compound represented by general formula (2):

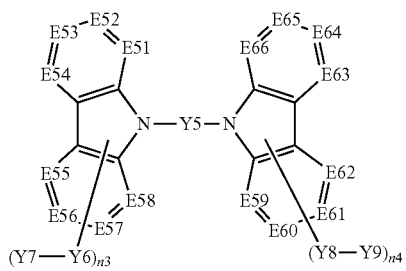

wherein Y5 represents a divalent linking group which is an arylene group, a heteroarylene group or a combination of the arylene group and the heteroarylene group; E51 to E66 each represent C(R3) or N, and R3 represents a hydrogen atom or a substituent; Y6 to Y9 each represent a group derived from an aromatic hydrocarbon ring or a group derived from an aromatic heterocycle, and at least one of Y6 and Y7 and at least one of Y8 and Y9 each represent a group derived from an aromatic heterocycle containing an N atom; and n3 and n4 each represent an integer of zero to four, provided that the sum of n3 and n4 is two or more.

7. The organic electroluminescence element according to claim 6, wherein the compound represented by the general formula (2) is a compound represented by general formula (3):

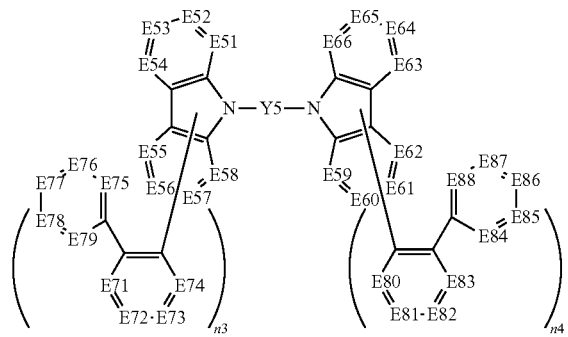

wherein Y5 represents a divalent linking group which is an arylene group, a heteroarylene group or a combination of the arylene group and the heteroarylene group; E51 to E66 and E71 to E88 each represent C(R3) or N, and R3 represents a hydrogen atom or a substituent, provided that at least one of E71 to E79 and at least one of E80 to E88 each represent N; and n3 and n4 each represent an integer of zero to four, provided that the sum of n3 and n4 is two or more.

8. The organic electroluminescence element accordlng to claim 1, wherein the phosphorescence emdtting compound is represented by general formula (4):

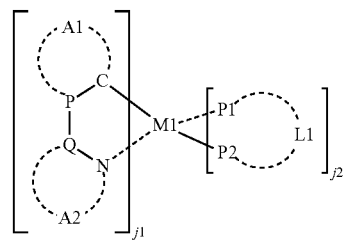

wherein P and Q each represent a carbon atom or a nitrogen atom; A1 represents an atom group which forms an aromatic hydrocarbon ring or an aromatic heterocycle with P-C; A2 represents an atom group which forms an aromatic heterocycle with Q-N; P1-L1-P2 represents a bidentate ligand, P1 and P2 each independently represent a carbon atom, a nitrogen atom or an oxygen atom, and L1 represents an atom group which forms the bidentate ligand with P1 and P2; j1 represents an integer of one to three, and j2 represents an integer of zero to two, provided that the sum of j1 and j2 is two or three; and M1 represents a transition metal element of groups 8 to 10 in the element periodic table.

9. The organic electroluminescence element according to claim 8, wherein the compound represented by the general formula (4) is a compound represented by general formula (5):

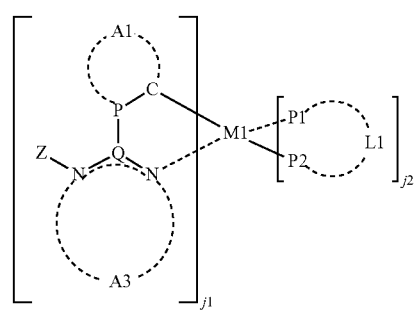

wherein Z represents a hydrocarbon ring group or a heterocyclic group; P and Q each represent a carbon atom or a nitrogen atom; A1 represents an atom group which forms an aromatic hydrocarbon ring or an aromatic heterocycle with P-C; A3 represents $C(R01)=C(R02)$, $N=C(R02)$, $C(R01)=N$ or $N=N$, and R01 and R02 each represent a hydrogen atom or a substituent; P1-L1-P2 represents a bidentate ligand, P1 and P2 each independently represent a carbon atom, a nitrogen atom or an oxygen atom, and L1 represents an atom group which forms the bidentate ligand with P1 and P2; j1 represents an integer of one to three, and j2 represents an integer of zero to two, provided that the sum of j1 and j2 is two or three; M1 represents a transition metal element of groups 8 to 10 in the element periodic table; and a broken line represents a single bond or a double bond.

10. The organic electroluminescence element according to claim 8, wherein the M1 represents iridium.

11. The organic electroluminescence element according to claim 1, further comprising an auxiliary electrode on the transparent conductive layer.

12. The organic electroluminescence element according to claim 11, wherein
the transparent protective layer is subjected to patterning, and
the auxiliary electrode is formed above a non-patterned region of the transparent protective layer.

13. An illumination device comprising the organic electroluminescence element according to claim 1.

14. The organic electroluminescence element according to claim 1, wherein the counter electrode is formed from aluminum, sodium, sodium-potassium alloy, magnesium, lithium, magnesium/copper mixture, magnesium/argentum mixture, magnesium/aluminum mixture, magnesium/indium mixture, aluminum/aluminum oxide ($Al_2O_3$) mixture, indium, lithiumialuminum mixture, or rare earth metal.

* * * * *